(12) United States Patent
Burke et al.

(10) Patent No.: US 7,357,942 B2
(45) Date of Patent: Apr. 15, 2008

(54) COMPOSITIONS, SYSTEMS, AND KITS FOR ADMINISTERING ZOTAROLIMUS AND PACLITAXEL TO BLOOD VESSEL LUMENS

(75) Inventors: Sandra E. Burke, Libertyville, IL (US); Keith R. Cromack, Gurnee, IL (US); Matthew Mack, Chicago, IL (US); John L. Toner, Libertyville, IL (US)

(73) Assignee: Abbott Laboratories, Abott Park, IL (US)

( * ) Notice: Subject to any disclaimer, the term of this patent is extended or adjusted under 35 U.S.C. 154(b) by 0 days.

(21) Appl. No.: 11/464,676

(22) Filed: Aug. 15, 2006

(65) Prior Publication Data

US 2007/0026035 A1     Feb. 1, 2007

Related U.S. Application Data

(60) Continuation-in-part of application No. 10/977,288, filed on Oct. 29, 2004, which is a continuation-in-part of application No. 10/796,243, filed on Mar. 9, 2004, which is a continuation-in-part of application No. 10/235,572, filed on Sep. 6, 2002, which is a continuation-in-part of application No. 09/950,307, filed on Sep. 10, 2001, now Pat. No. 6,890,546, which is a continuation-in-part of application No. 09/433,001, filed on Nov. 2, 1999, now Pat. No. 6,329,386, which is a division of application No. 09/159,945, filed on Sep. 24, 1998, now Pat. No. 6,015,815.

(60) Provisional application No. 60/732,577, filed on Oct. 17, 2005, provisional application No. 60/726,878, filed on Oct. 14, 2005, provisional application No. 60/727,196, filed on Oct. 14, 2005, provisional application No. 60/727,080, filed on Oct. 14, 2005, provisional application No. 60/664,328, filed on Mar. 23, 2005, provisional application No. 60/554,730, filed on Mar. 19, 2004, provisional application No. 60/453,555, filed on Mar. 10, 2003, provisional application No. 60/060,105, filed on Sep. 26, 1997.

(51) Int. Cl.
*A61F 2/02* (2006.01)
*A61K 31/44* (2006.01)
*A61K 31/335* (2006.01)

(52) U.S. Cl. ................ 424/423; 514/291; 514/449

(58) Field of Classification Search ................ 424/423; 514/291, 449
See application file for complete search history.

(56) References Cited

U.S. PATENT DOCUMENTS

| | | |
|---|---|---|
| 3,929,992 A | 12/1975 | Sehgal |
| 3,993,749 A | 11/1976 | Sehgal |
| 4,316,885 A | 2/1982 | Rakhit |
| 4,401,653 A | 8/1983 | Eng |
| 4,650,803 A | 3/1987 | Stella |
| 4,885,171 A | 12/1989 | Surendra |
| 4,916,193 A | 4/1990 | Tang |
| 4,994,071 A | 2/1991 | MacGregor |
| 5,023,262 A | 6/1991 | Caufield |
| 5,092,877 A | 3/1992 | Pinchuk |
| 5,120,725 A | 6/1992 | Kao |
| 5,120,727 A | 6/1992 | Kao |
| 5,120,842 A | 6/1992 | Failli |
| 5,163,952 A | 11/1992 | Froix |
| 5,177,203 A | 1/1993 | Failli |
| 5,304,121 A | 4/1994 | Sahatjian |
| 5,447,724 A | 9/1995 | Helmus |
| 5,457,111 A | 10/1995 | Luly |
| 5,464,650 A | 11/1995 | Berg |
| 5,516,781 A | 5/1996 | Morris |
| 5,527,337 A | 6/1996 | Stack |
| 5,563,146 A | 10/1996 | Morris |
| 5,605,696 A | 2/1997 | Eury |
| 5,624,411 A | 4/1997 | Tuch |
| 5,646,160 A | 7/1997 | Morris |
| 5,665,728 A | 9/1997 | Morris |
| 5,705,583 A | 1/1998 | Bowers |
| 6,015,815 A | 1/2000 | Mollison |
| 6,090,901 A | 7/2000 | Bowers |
| 6,273,913 B1 | 8/2001 | Wright |
| 6,284,305 B1 | 9/2001 | Ding |

The BiodivYsio PC-coated Stent

| 6,358,556 B1 | 3/2002 | Ding |
| --- | --- | --- |
| 6,413,272 B1 | 7/2002 | Igaki |
| 6,419,692 B1 | 7/2002 | Yang |
| 6,585,764 B2 | 7/2003 | Wright |
| 2003/0129215 A1 | 7/2003 | Mollison |
| 2005/0004661 A1 | 1/2005 | Lewis |
| 2005/0019404 A1 | 1/2005 | Sung Hsing-Wen et al. |
| 2005/0175660 A1 | 8/2005 | Mollison et al. |
| 2005/0288481 A1 | 12/2005 | Desnoter et al. |

FOREIGN PATENT DOCUMENTS

| EP | 0184162 A2 | 6/1986 |
| --- | --- | --- |
| EP | 0 467 606 | 1/1992 |
| WO | WO 92/05179 | 4/1992 |
| WO | 01/87372 A1 | 11/2001 |
| WO | 02/055122 A1 | 7/2002 |
| WO | WO 2005/110508 | 11/2005 |
| WO | WO 2007/032777 | 3/2007 |
| WO | WO 2007/046935 | 4/2007 |
| WO | WO 2007/047416 | 4/2007 |

OTHER PUBLICATIONS

Aggarwal, A., D.J. Schneider, B.E. Sobel, and H.L. Dauerman. 2003 Comparison of inflammatory markers in patients with diabetes mellitus versus those without before and after coronary arterial stenting. Am J Cardiol. 92:924-9.

Baker, H., A. Sidorowicz, S.N. Sehgal, and C. Vezina. 1978. Rapamycin (AY-22,989), a new antifungal antibiotic. III. In vitro and in vivo evaluation. J Antibiot (Tokyo). 31:539-45.

Bierer, B.D., S.L. Schreiber, and S.J. Burakoff. 1991. The effect of the immunosuppressant FK-506 on alternate pathways of T cell activation. Eur J Immunol. 21:439-45.

Biondi-Zoccai, G.G., A. Abbate, G. Liuzzo, and L.M. Biasucci. 2003. Atherothrombosis, inflammation, and diabetes. J Am Coll Cardiol. 41:1071-7.

Brown, E.J., M.W. Albers, T.B. Shin, K. Ichikawa, C.T. Keith, W.S. Lane, and S.L. Schreiber. 1994. A mammalian protein targeted by G1-arresting rapamycin-receptor complex. Nature. 369:756-8.

Bunchman, T.E., and C.A. Brookshire. 1991. Smooth muscle cell proliferation by conditioned media from cyclosporine-treated endothelial cells: a role of endothelin. Transplant Proc. 23:967-8.

Carter, A.J., M. Aggarwal, G.A. Kopia, F. Tio, P.S. Tsao, R. Kolata, A.C. Yeung, G. Llanos, J. Dooley, and R. Falotico. 2004. Long-term effects of polymer-based, slow-release, sirolimus-eluting stents in a porcine coronary model. Cardiovasc Res. 63:617-24.

Dandona, P., and A. Aljada. 2002. A rational approach to pathogenesis and treatment of type 2 diabetes mellitus, insulin resistance, inflammation, and atherosclerosis. Am J Cardiol. 90:27G-33G.

Dumont, F.J., M.R. Melino, M.J. Staruch, S.L. Koprak, P.A. Fischer, and N.H. Sigal. 1990 The immunosuppressive macrolides FK-506 and rapamycin act as reciprocal antagonists in murine T cells. J Immunol. 144:1418-24.

Fretz, H., M. Albers, A. Gala, R. Standaert, W. Lane, S. Burakoff, B. Bierer, and S. Schreiber. 1991. Rapamycin and FK506 binding proteins (immunophilins). J. Am. Chem. Soc. 113:1409-1411.

Grech, E.D., and D.R. Ramsdale. 2003 Acute coronary syndrome: unstable angina and non-ST segment elevation myocardial infarction. British Med. J. 326:1259-61.

Harding, M.W., A. Galat, D.E. Uehling, and S.L. Schreiber. 1989. A receptor for the immunosuppressant FK506 is a cis-trans peptidyl-prolyl isomerase. Nature. 341:758-60.

Hayward, C., D. Yohannes, and S. Danishefsky. 1993. Total synthesis of rapamycin via a novel titanium-mediated aldol macrocyclization reaction. J. Am. Chem. Soc. 115:9345-9346.

Helmus, M. 1990. Medical Device Design—A Systems Approach: Central Venous Catheters. In 22nd International Society for the Advancement of Material and Process Engineering Technical Conference.

Ji, Q., M. Reimer, and T. El-Shourbagy. 2004. 96-well liquid—liquid extraction liquid chromatography-tandem mass spectrometry method for the quantitative determination of ABT-578 in human blood samples. Journal of Chromatography B. 805:67-75.

Kino, T., N. Inamura, F. Sakai, K. Nakahara, T. Goto, M. Okuhara, M. Kohsaka, H. Aoki, and T. Ochiai. 1987. Effect of FK-506 on human mixed lymphocyte reaction in vitro. Transplant Proc. 19:36-9.

Kornowski, R., M.K. Hong, F.O. Tio, O. Bramwell, H. Wu, and M.B. Leon. 1998. In-stent restenosis: contributions of inflammatory responses and arterial injury to neointimal hyperplasia. J Am Coll Cardiol. 31:224-30.

Martel, R.R., J. Klicius, and S. Galet. 1977. Inhibition of the immune response by rapamycin, a new antifungal antibiotic. Can J Physiol Pharmacol. 55:48-51.

Morris, R. 1992. Rapamycins: antifungal, antitumor, antiproliferative, and immunosuppressive macrolides. Transplant. Rev. 6:39-87.

Morris, R., and B. Meiser. 1989. Identification of a new pharmacologic action for an old compound. Med. Sci. Res. 17:609.

Nicolaou, K., T. Chakraborty, A Piscopio, N. Minowa, and P. Bertinato. 1993. Total synthesis of rapamycin. J. Am. Chem. Soc. 115:4419-4420.

Paiva, N.L., A.L. Demain, and M.F. Roberts. 1991, Incorporation of acetate, propionate, and methionine into rapamycin by *Streptomyces hygroscopicus*. J Nat Prod. 54:167-77.

Roffi, M., and E.J. Topol. 2004. Percutaneous coronary intervention in diabetic patients with non-ST-segment elevation acute coronary syndromes. Eur. Heart J. 25:190-8.

Romo, D., S. Meyer, D. Johsnon, and S. Schrieber. 1993. Total synthesis of (-)-rapamycin using an Evans-Tishchenko fragment coupling. J. Am. Chem. Soc. 115:7906-7907.

Sabatini, D.M., H. Erdjument-Bromage, M. Lui, P. Tempst, and S.H. Snyder. 1994. RAFT1: a mammalian protein that binds to FKBP12 in a rapamycin-dependent fashion and is homologous to yeast TORs. Cell. 78:35-43.

Schwartz, R. 1992. Restenosis and the proportional neointimal response to coronary artery injury: results in a porcine model. J Am Coll Cardiol. 19:267-274.

Sehgal, S.N., H. Baker, C.P. Eng, K. Singh, and C. Vezina. 1983. Demethoxyrapamycin (AY-24,668), a new antifungal antibiotic. J Antibiot (Tokyo). 36:351-4.

Sehgal, S.N., H. Baker, and C. Vezina. 1975. Rapamycin (AY-22,989), a new antifungal antibiotic. II. Fermentation, isolation and characterization. J Antibiot (Tokyo). 28:727-32.

Shichiri, M., Y. Hirata, T. Nakajima, K. Ando, T. Imai, M. Yanagisawa, T. Masaki, and F. Marumo. 1991. Endothelin-1 is an autocrine/paracrine growth factor for human cancer cell lines. J Clin Invest. 87:1867-71.

Siekierka, J.J., S.H. Hung, M. Poe, C.S. Lin, and N.H. Sigal. 1989. A cytosolic binding protein for the immunosuppressant FK506 has peptidyl-prolyl isomerase activity but is distinct from cyclophilin. Nature. 341:755-7.

Suzuki, T., G. Kopia, S. Hayashi, L.R. Bailey, G. Llanos, R. Wilensky, B.D. Klugherz, G. Papandreou, P. Narayan, M.B. Leon, A.C. Yeung, F. Tio, P.S. Tsao, R. Falotico, and A.J. Carter. 2001. Stent-based delivery of sirolimus reduces neointimal formation in a porcine coronary model. Circulation. 104:1188-93.

Vezina, C., A. Kudelski, and S.N. Sehgal. 1975. Rapamycin (AY-22,989), a new antifungal antibiotic. I. Taxonomy of the producing streptomycete and isolation of the active principle. J Antibiot (Tokyo). 28:721-6.

Yamagishi, S., C.C. Hsu, K. Kobayashi, and H. Yamamoto. 1993. Endothelin 1 mediates endothelial cell-dependent proliferation of vascular pericytes. Biochem Biophys Res Commun. 191:840-6.

Yudkin, J.S., M. Kumari, S.E. Humphries, and V. Mohamed-Ali. 2000. Inflammation, obesity, stress and coronary heart disease: is interleukin-6 the link? Atherosclerosis. 148:209-14.

International Search Report for PCT/US2007/017619 filed Aug. 7, 2007, mailed Feb. 4, 2008, 13 pgs.

Leon et al., "Drug-eluting stents and glycoprotein llb/llla inhibitors: Combination therapy for the future", Am. Heart J. vol. 146, No. 4, pp. S13-S17 (2003).

Primary Examiner—Sharon E. Kennedy
(74) Attorney, Agent, or Firm—Squire, Sanders & Dempsey LLP

(57) ABSTRACT

A system and compositions including zotarolimus and paclitaxel are disclosed, as well as methods of delivery, wherein the drugs have effects that complement each other. Medical devices are disclosed which include supporting structures that include at least one pharmaceutically acceptable carrier or excipient, which carrier or excipient can include one or more therapeutic agents or substances, with the carrier including at least one coating on the surface thereof, and the coating associated with the therapeutic substances, such as, for example, drugs. Supporting structures for the medical devices that are suitable for use in this invention include, but are not limited to, coronary stents, peripheral stents, catheters, arterio-venous grafts, by-pass grafts, and drug delivery balloons used in the vasculature. These compositions and systems can be used in combination with other drugs, including anti-proliferative agents, anti-platelet agents, anti-inflammatory agents, anti-thrombotic agents, cytotoxic drugs, agents that inhibit cytokine or chemokine binding, cell de-differentiation inhibitors, anti-lipaedemic agents, matrix metalloproteinase inhibitors, cytostatic drugs, or combinations of these and other drugs.

18 Claims, 21 Drawing Sheets

Mean ABT-578 Blood Concentration-Time Profiles, Log-Linear Scale

Mean ABT-578 Blood Concentration-Time Profiles for the 200, 400 and 800 μg OD Dose Groups on Day 1, Day 14 and Days 1 through 14.

Mean Observed and Predicted Blood Concentration *versus* Time Plots Upon Fitting the 800 μg QD Dose Group Data

Figures 10B-C
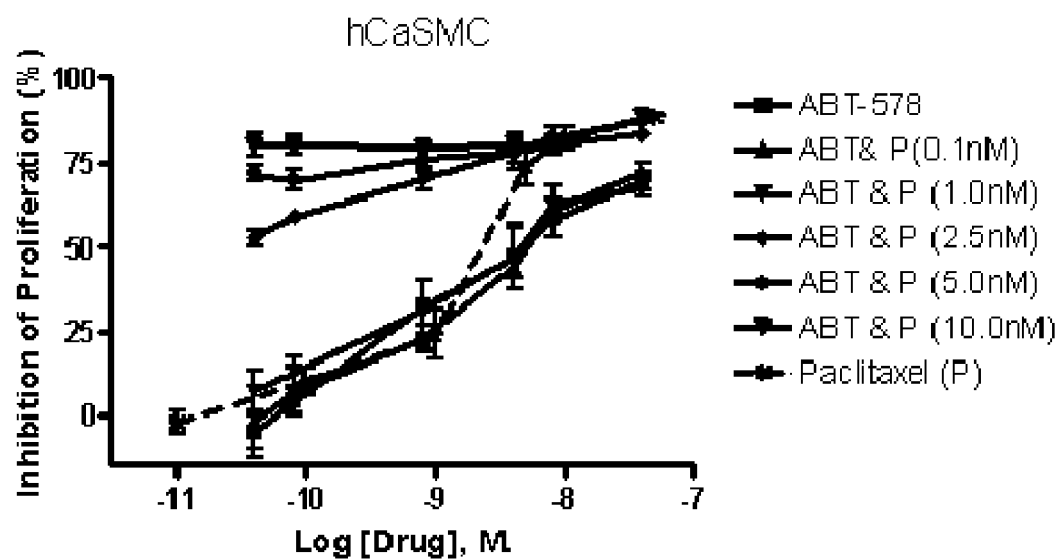
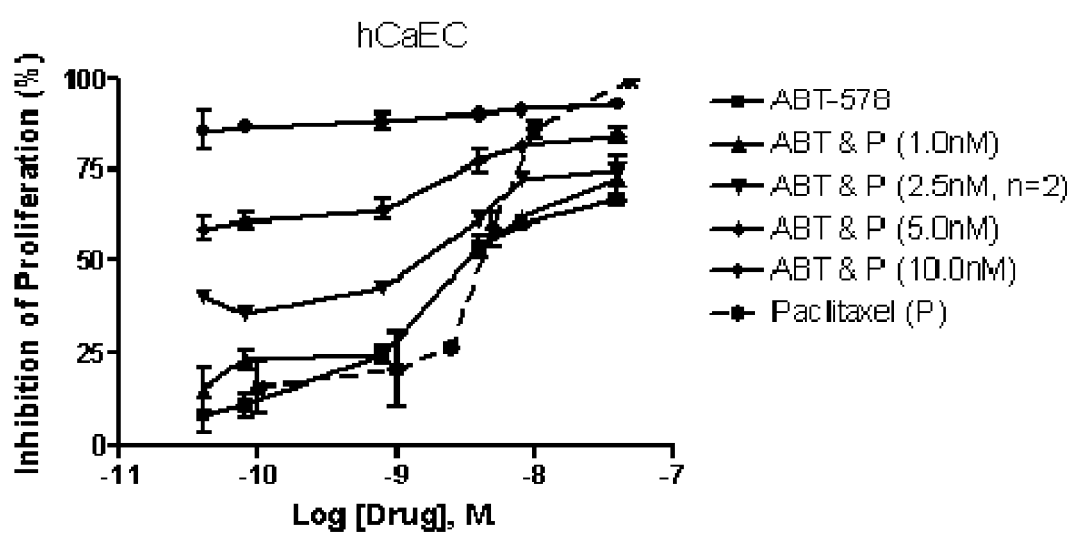

Figures 10D-G
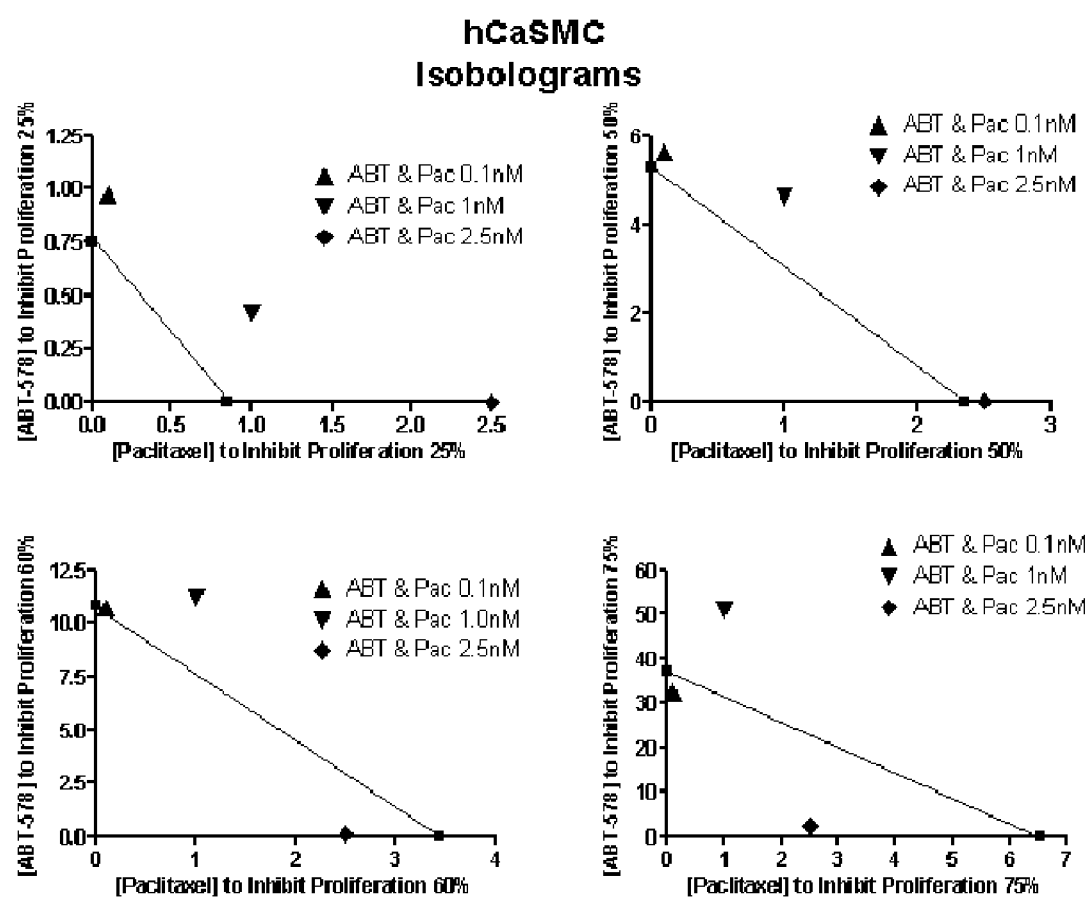

Figures 10H-K
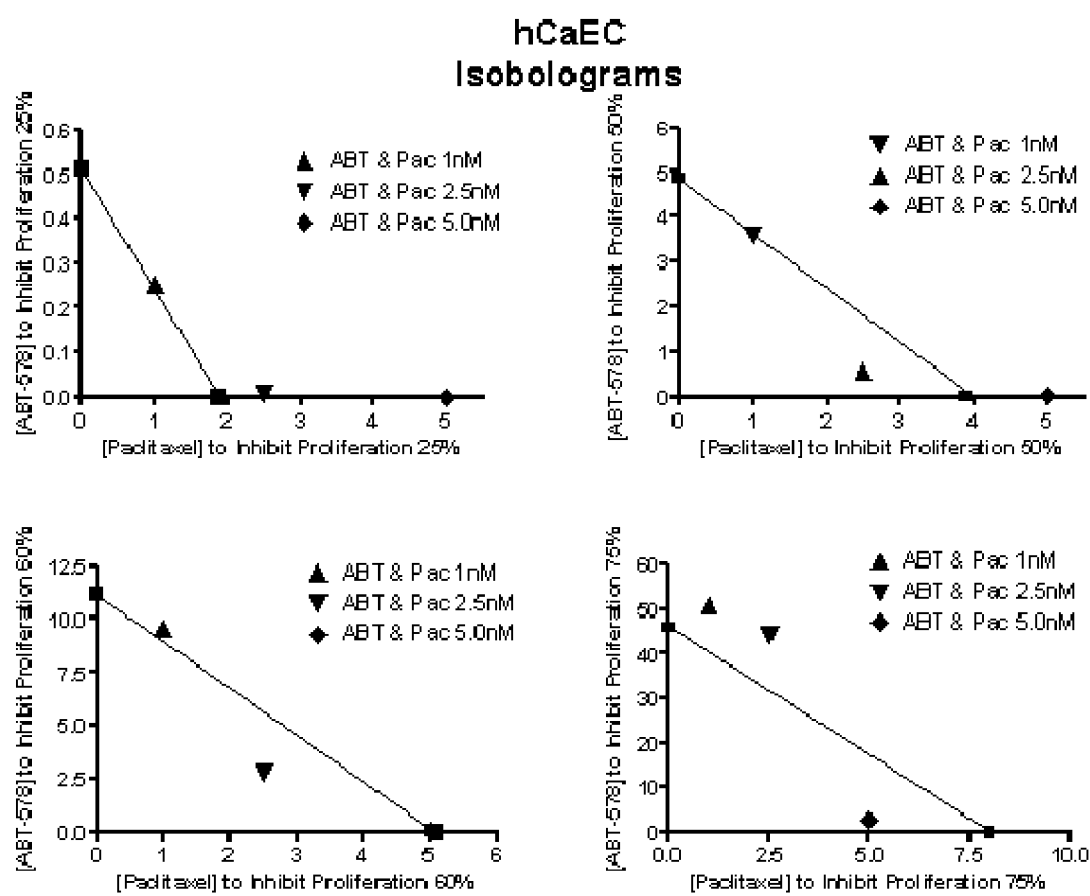

Figures 10L-M
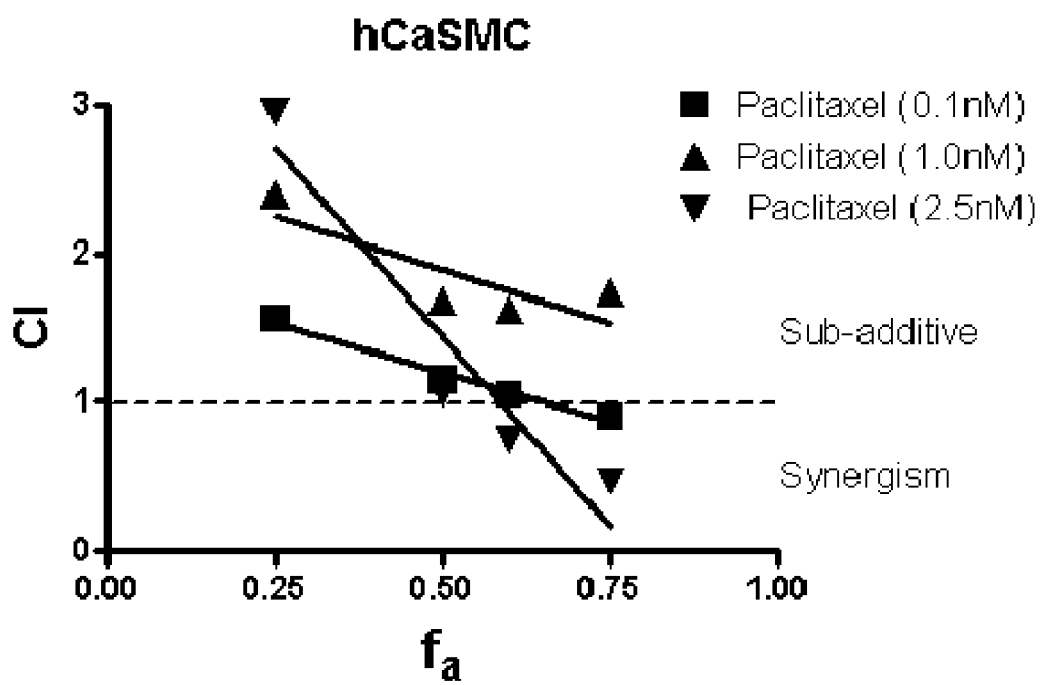
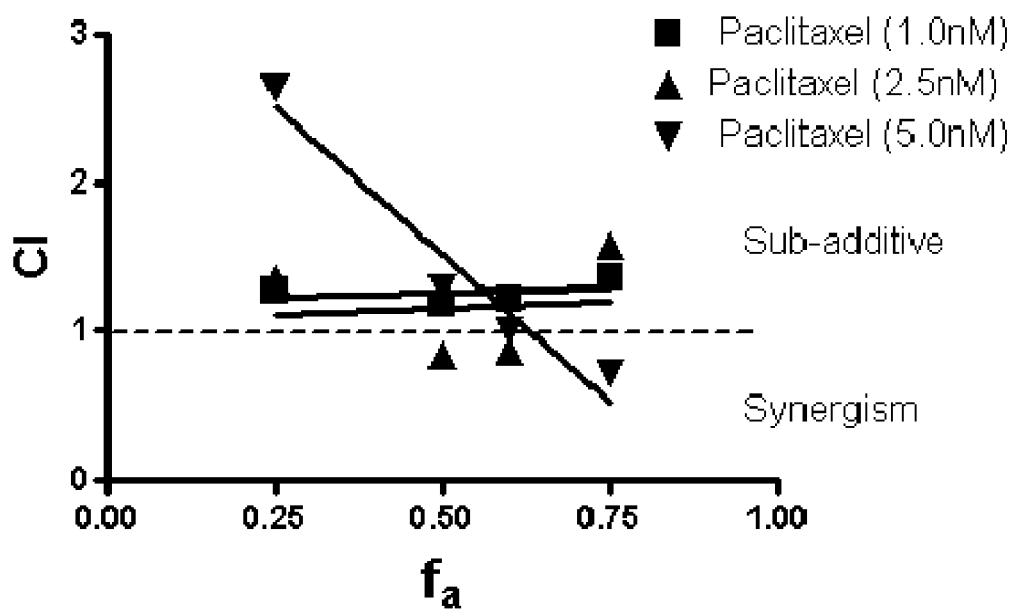

COMPOSITIONS, SYSTEMS, AND KITS FOR ADMINISTERING ZOTAROLIMUS AND PACLITAXEL TO BLOOD VESSEL LUMENS

CROSS-REFERENCE TO RELATED APPLICATIONS

This application is a continuation-in-part of U.S. Ser. No. 10/796,243 filed Mar. 9, 2004, which claims priority to U.S. Ser. No. 60/453,555 filed Mar. 10, 2003 and this application is a continuation-in-part of U.S. Ser. No. 10/977,288 filed Oct. 29, 2004, which is a continuation-in-part of U.S. Ser. No. 10/235,572, filed Sep. 6, 2002, which is a continuation in part of U.S. Ser. No. 09/950,307, filed Sep. 10, 2001, now U.S. Pat. No. 6,890,546, which is a continuation-in-part of U.S. Ser. No. 09/433,001, filed Nov. 2, 1999, now U.S. Pat. No. 6,329,386, which is a divisional of U.S. Ser. No. 09/159,945, filed Sep. 24, 1998, now U.S. Pat. No. 6,015,815 and claims priority to U.S. Ser. No. 60/060,105, filed Sep. 26, 1997; this application also claims priority to U.S. Ser. No. 60/664,328 filed on Mar. 23, 2005, U.S. Ser. No. 60/727,080 filed Oct. 14, 2005, U.S. Ser. No. 60/726,878 filed Oct. 14, 2005, U.S. Ser. No. 60/732,577 filed Oct. 17, 2005, U.S. Ser. No. 60/554,730 filed Mar. 19, 2004 which is a provisional application of U.S. Ser. No. 11/084,172 filed Mar. 18, 2005, and U.S. Ser. No. 60/727,196 filed Oct. 14, 2005; the entirety of all the above of which is incorporated herein by reference.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable.

TECHNICAL FIELD

Embodiments of the invention relate to novel chemical compounds having immunomodulatory activity and/or anti-restenotic activity and synthetic intermediates useful for the preparation of the novel compounds, and in particular to macrolide immunomodulators. More particularly, the invention relates to semisynthetic analogs of rapamycin, means for their preparation, pharmaceutical compositions including such compounds, and methods of treatment employing the same.

BACKGROUND OF THE INVENTION

Introduction

The compound cyclosporine (cyclosporin A) has found wide use since its introduction in the fields of organ transplantation and immunomodulation, and has brought about a significant increase in the success rate for transplantation procedures. Recently, several classes of macrocyclic compounds having potent immunomodulatory activity have been discovered. Okuhara et al. disclose a number of macrocyclic compounds isolated from the genus Streptomyces, including the immunosuppressant FK-506, a 23-membered macrocyclic lactone, which was isolated from a strain of S. tsukubaensis (Okuhara et al., 1986).

Other related natural products, including FR-900520 and FR-900523, which differ from FK-506 in their alkyl substituent at C-21, have been isolated from S. hygroscopicus yakushimnaensis. Another analog, FR-900525, produced by S. tsukubaensis, differs from FK-506 in the replacement of a pipecolic acid moiety with a proline group. Unsatisfactory side-effects associated with cyclosporine and FK-506 including nephrotoxicity, have led to a continued search for immunosuppressant compounds having improved efficacy and safety, including an immunosuppressive agent which is effective topically, but ineffective systemically (Luly, 1995).

Rapamycin

Rapamycin is a macrocyclic triene antibiotic produced by Streptomyces hygroscopicus, which was found to have anti-fungal activity, particularly against Candida albicans, both in vitro and in vivo (Baker et al., 1978; Sehgal, 1975; Sehgal, 1976; Sehgal et al., 1975; Vezina et al., 1975).

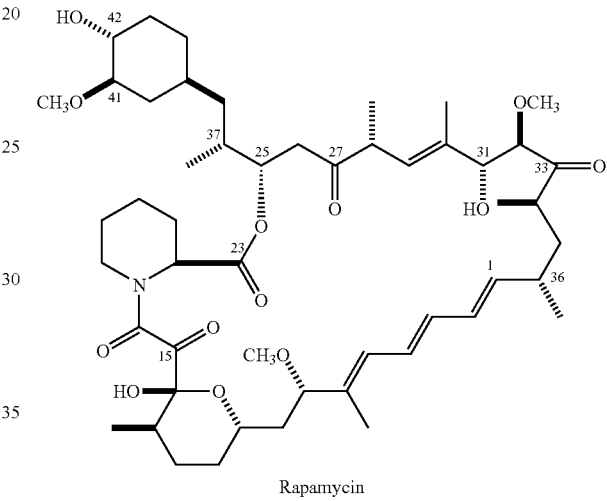

Rapamycin

Rapamycin alone (Surendra, 1989) or in combination with picibanil (Eng, 1983) has been shown to have anti-tumor activity. In 1977, rapamycin was also shown to be effective as an immunosuppressant in the experimental allergic encephalomyelitis model, a model for multiple sclerosis; in the adjuvant arthritis model, a model for rheumatoid arthritis; and was shown to effectively inhibit the formation of IgE-like antibodies (Martel et al., 1977).

The immunosuppressive effects of rapamycin have also been disclosed in FASEB, 1989, 3, 3411 as has its ability to prolong survival time of organ grafts in histo-incompatible rodents (Morris and Meiser, 1989). The ability of rapamycin to inhibit T-cell activation was disclosed by M. Strauch (FASEB, 1989, 3, 3411). These and other biological effects of rapamycin have been previously reviewed (Morris, 1992).

Rapamycin has been shown to reduce neointimal proliferation in animal models, and to reduce the rate of restenosis in humans. Evidence has been published showing that rapamycin also exhibits an anti-inflammatory effect, a characteristic which supported its selection as an agent for the treatment of rheumatoid arthritis. Because both cell proliferation and inflammation are thought to be causative factors in the formation of restenotic lesions after balloon angioplasty and stent placement, rapamycin and analogs thereof have been proposed for the prevention of restenosis.

Mono-ester and di-ester derivatives of rapamycin (esterification at positions 31 and 42) have been shown to be useful as antifungal agents (Rakhit, 1982) and as water soluble prodrugs of rapamycin (Stella, 1987).

Fermentation and purification of rapamycin and 30-demethoxy rapamycin have been described in the literature (Paiva et al., 1991; Sehgal et al., 1983; Sehgal et al., 1975; Vezina et al., 1975).

Numerous chemical modifications of rapamycin have been attempted. These include the preparation of mono- and di-ester derivatives of rapamycin (Caufield, 1992), 27-oximes of rapamycin (Failli, 1992a); 42-oxo analog of rapamycin (Caufield, 1991); bicyclic rapamycins (Kao, 1992a); rapamycin dimers (Kao, 1992b); silyl ethers of rapamycin (Failli, 1992b); and arytsulfonates and sulfamates (Failli, 1993). Rapamycin was recently synthesized in its naturally occurring enantiomeric form (Hayward et al., 1993; Nicolaou et al., 1993; Romo et al., 1993).

It has been known that rapamycin, like FK-506, binds to FKBP-12 (Bierer et al., 1991; Dumont et al., 1990; Fretz et al., 1991; Harding et al., 1989; Siekierka et al., 1989). Recently it has been discovered that the rapamycin/FKBP-12 complex binds to yet another protein, which is distinct from calcineurin, the protein that the FK-506/FKBP-12 complex inhibits (Brown et al., 1994; Sabatini et al., 1994).

Other drugs have been used to counter unwanted cell proliferation. Exemplary of these is paclitaxel. A complex alkaloid extracted from the Pacific Yew, *Taxus brevifolia*, paclitaxel stabilizes components of the cell skeleton (tubulin, the building blocks of microtubules) that are critical in cell division, thus preventing cell proliferation (Miller and Ojima, 2001).

Stents

Percutaneous transluminal coronary angioplasty (PTCA) was developed by Andreas Gruentzig in the 1970's. The first canine coronary dilation was performed on Sep. 24, 1975; studies showing the use of PTCA were presented at the annual meetings of the American Heart Association the following year. Shortly thereafter, the first human patient was studied in Zurich, Switzerland, followed by the first American human patients in San Francisco and New York. While this procedure changed the practice of interventional cardiology with respect to treatment of patients with obstructive coronary artery disease, the procedure did not provide long-term solutions. Patients received only temporary abatement of the chest pain associated with vascular occlusion; repeat procedures were often necessary. It was determined that the existence of restenotic lesions severely limited the usefulness of the new procedure. In the late 1980's, stents were introduced to maintain vessel patency after angioplasty. Stenting is involved in 90% of angioplasty performed today. Before the introduction of stents, the rate of restenosis ranged from 30% to 50% of the patients who were treated with balloon angioplasty. The recurrence rate after dilatation of in-stent restenosis may be as high as 70% in selected patient subsets, while the angiographic restenosis rate in de novo stent placement is about 20%. Placement of the stent reduced the restenosis rate to 15% to 20%. This percentage likely represents the best results obtainable with purely mechanical stenting. The restenosis lesion is caused primarily by neointimal hyperplasia, which is distinctly different from atherosclerotic disease both in time-course and in histopathologic appearance. Restenosis is a healing process of damaged coronary arterial walls, with neointimal tissue impinging significantly on the vessel lumen. Vascular brachytherapy appears to be efficacious against in-stent restenosis lesions. Radiation, however, has limitations of practicality and expense, and lingering questions about safety and durability.

Stents and Combination Therapies

The major effort undertaken by the interventional device community to fabricate and evaluate drug eluting stents has met the original goal by reducing restenosis by at least 50%. However, there still remains a need for improved local drug delivery devices, e.g., drug-impregnated polymer-coated stents, that provide safe and efficacious tools for preventing and treating restenosis. For example, the two commercially available single-drug elution stents reduce restenosis and improve patient outcomes, but do not eliminate restenosis or are free of adverse safety issues. Patients, and especially at-risk patients, including diabetics, those with small vessels and those with acute coronary syndromes, could benefit from local drug delivery devices, including stents with improved capabilities. Drug delivery devices including combinations of drugs are known. However, the art does not appear to teach particularly effective drug combinations administered locally, e.g., eluted from a stent. For example, and as discussed more below, Falotico teaches an EVA-PBMA polymer-coated stent including a rapamycin/dexamethasone combination that was "far less effective" in reducing neointimal area, percent-area stenosis, and inflammation scores than stents delivering either rapamycin alone or dexamethasone alone (Falotico, 2003).

BRIEF DESCRIPTION OF THE DRAWINGS

FIGS. 10A-I shows that tacrolimus blocks the anti-proliferative activity of zotarolimus in smooth muscle cells in vitro (FIG. 10A). The anti-proliferative activity of zotarolimus, paclitaxel (P) and combinations in smooth muscle cells (FIG. 10B) and endothelial cells (FIG. 10C) in vitro are also shown. Proliferation was determined by measuring the incorporation of $^3$H-thymidine into newly synthesized DNA of cells stimulated by serum and growth factors. Data are the mean±SEM of 3 experiments, except as noted. FIGS. 10D-G show isobologram analyses of combination anti-proliferative activity in smooth muscle cells. The concentrations producing the specified level of anti-proliferative activity were determined from the dose-response curves generated by non-linear curve fitting of the data means. FIGS. 10H-K show isobologram analyses of the anti-proliferative activity of the combination of zotarolimus and paclitaxel in endothelial cells. The concentrations of compounds producing the specified levels of activity were determined from the mean data. FIGS. 10L-M shows a combination index (CI) analysis of the anti-proliferative activity of combinations of ABT-578 and paclitaxel in hCaSMC and hCaEC. CI levels were determined from the mean data using the method of Chou and Talalay (Chou and Talalay, 1984).

FIG. 19*a*, TriMaxx™, stent; 19*b*, ZoMaxx™, stent; 19*c*, Cypher® stent; 19*d*, Taxus® stent; 19*e*, zotarolimus:paclitaxel, 10 μg/mm:1 μg/mm stent.

SUMMARY OF THE INVENTION

Figure 1:
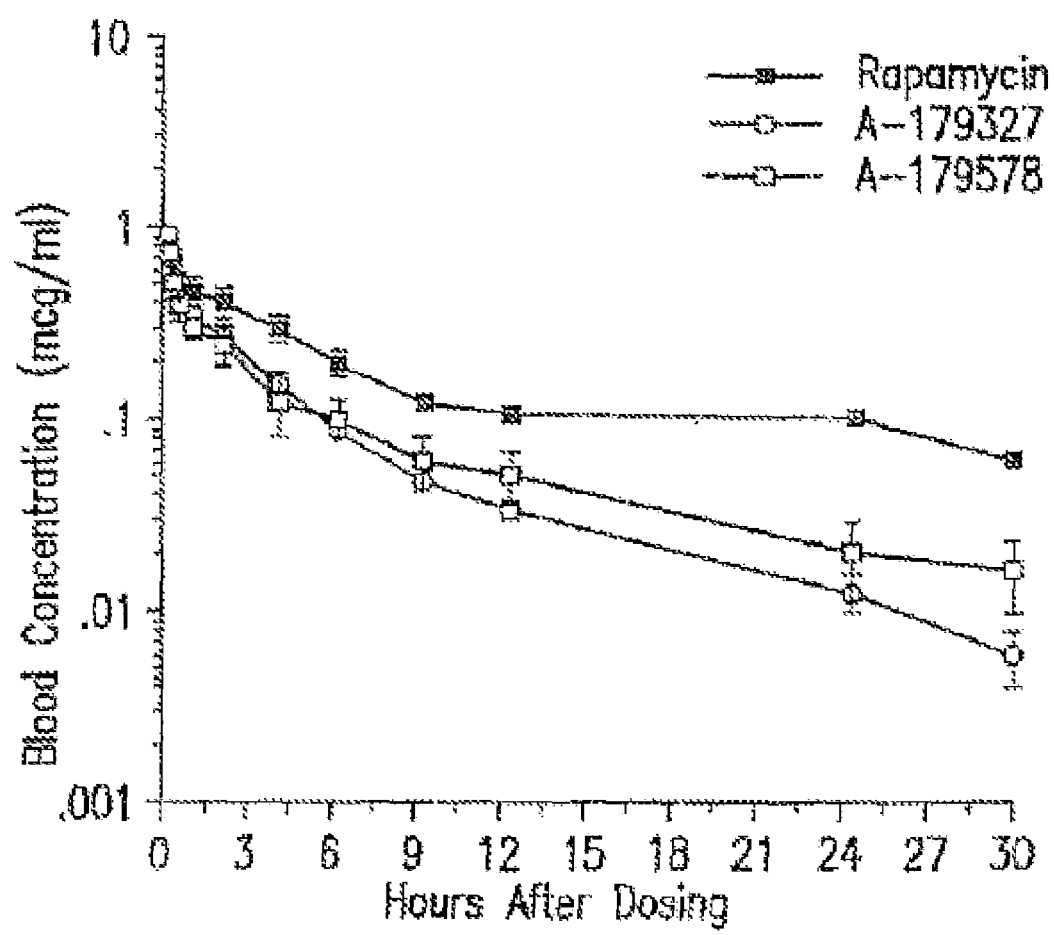
FIG. 1 shows blood concentrations±SEM (n=3) of tetrazole-including rapamycin analogs dosed in monkey.

In an aspect, the invention is directed to a drug delivery system that has a supporting structure including at least one pharmaceutically acceptable carrier or excipient, and a therapeutic composition having zotarolimus and paclitaxel or derivatives, prodrugs, or salts thereof, wherein the formation of neointimal hyperplasia is reduced when the system is implanted in a lumen of a blood vessel of a subject when compared to a control system. The subject includes a mammalian including, but not limited to, humans or swine. The ratio of zotarolimus:paclitaxel, r, is by weight $10:7 \leq r \leq 10:0.01$, and in some cases, r=10:1. For example, the concentration of zotarolimus includes about 10 μg/mm of stent, and the concentration of paclitaxel includes about 1μg/mm. The drug delivery system can include a stent, and can include a third—or more—drugs or other therapeutic substances, including biologicals. Other therapeutic substances include, but not limited to, anti-proliferative agents, anti-platelet agents, steroidal and non-steroidal anti-inflammatory agents, anti-thrombotic agents, and thrombolytic agents.

In another aspect, the invention is directed to a system for providing controlled release delivery of drugs for inhibiting neointimal hyperplasia in a blood vessel. The system includes a plurality of therapeutic substances/agents including zotarolimus or salts, prodrugs or derivatives thereof; and paclitaxel or salts, prodrugs, or derivatives thereof, and the activities of the therapeutic substance(s)/agent(s) are complementary. The ratio of zotarolimus:paclitaxel, r, is by weight $10:7 \leq r \leq 10:0.01$, and in some cases, r=10:1. For example, the concentration of zotarolimus includes about 10 μg/mm of stent, and the concentration of paclitaxel includes about 1μg/mm. The drug delivery system can include a stent, a coated stent, and can include a third—or more—drugs or other therapeutic substances, including biologicals. Other therapeutic substances include, but not limited to, anti-proliferative agents, anti-platelet agents, steroidal and non-steroidal anti-inflammatory agents, anti-thrombotic agents, and thrombolytic agents.

In yet another aspect, the invention is directed to pharmaceutical compositions that include paclitaxel or salts, prodrugs or derivatives thereof; and zotarolimus or salts, prodrugs, or derivatives thereof, wherein the ratio of zotarolimus:paclitaxel, r, is by weight $10:7 \leq r \leq 10:0.01$; wherein if the composition is administered to a subject in a blood vessel on a medical device, the formation of neointimal hyperplasia is reduced; and wherein the composition is formulated for local delivery to a subject. The ratio can be r=10:1, and the formulation can further be associated with a medical device, including a stent, or a coated stent. The concentration of zotarolimus includes about 10 μg/mm of stent, and the concentration of paclitaxel includes about 1 μg/mm of stent. The subject can be a mammalian including, but not limited to, humans or swine.

In yet still another aspect, the invention is directed to compositions that include zotarolimus or salts, prodrugs, or derivatives thereof; and paclitaxel or salts, prodrugs, or derivatives thereof; wherein the ratio of zotarolimus:paclitaxel, r, is by weight $10:7 \leq r \leq 10:0.01$, and wherein an effect of the zotarolimus complements activity of paclitaxel, and paclitaxel complements activity of zotarolimus when locally administered. The ratio can be r=10:1, and the formulation include a medical device, including a stent. The concentration of zotarolimus includes about 10 μg/mm of stent, and the concentration of paclitaxel includes about 1 μg/mm of stent. The subject can be mammalians including, but not limited to, humans and swine.

In a further aspect, the invention is directed to methods of treatment, by placing or administering to a subject any of the described systems or compositions that include zotarolimus or salts, prodrugs, or derivatives thereof; and paclitaxel or salts, prodrugs, or derivatives thereof; wherein the ratio of zotarolimus:paclitaxel, r, is by weight $10:7 \leq r \leq 10:0.01$.

In yet a further aspect, the invention is directed to kits including any of the described systems or compositions that include zotarolimus or salts, prodrugs, or derivatives thereof; and paclitaxel or salts, prodrugs, or derivatives thereof, wherein the ratio of zotarolimus:paclitaxel, r, is by weight $10:7 \leq r \leq 10:0.01$ In still yet a further aspect, the invention is directed to a drug delivery system, that includes a stent associated with at least one coating on a surface, the coating associated with at least one therapeutic composition that includes zotarolimus and paclitaxel or derivatives, prodrugs, or salts thereof, wherein neointimal hyperplasia is reduced when the system is implanted in a lumen of a blood vessel of a subject when compared to a control system, wherein neointimal hyperplasia is reduced by ≧10% when compared to the control system, wherein the ratio, r, of zotarolimus:paclitaxel by weight is 10:7≦r≦10:0.01. The ratio, r, can be r=10:1, and the concentration of zotarolimus includes about 10 μg/mm of stent, and the concentration of paclitaxel includes about 1μg/mm.

In another aspect, the invention provides systems for the controlled release delivery of drugs for treating or inhibiting neointimal hyperplasia in a blood vessel, the system including a stent, the stent is associated with at least one coating that includes zotarolimus or salts, prodrugs, or derivatives thereof and paclitaxel or salts, prodrugs, or derivatives thereof; wherein the ratio of zotarolimus:paclitaxel by weight is 10:7≦r≦10:0.1; and wherein zotarolimus complements paclitaxel activity, and paclitaxel complements zotarolimus activity. The ratio, r, can be r=10:1, and the concentration of zotarolimus includes about 10 μg/mm of stent, and the concentration of paclitaxel includes about 1 μg/mm of stent.

DETAILED DESCRIPTION OF THE INVENTION

Definitions

The term "prodrug," as used herein, refers to compounds which are rapidly transformed in Vito to the parent compound of the above formula, for example, by hydrolysis in blood. A thorough discussion is provided by Higuchi and V. Stella (Higuchi and Stella, 1987) and by Roche (Roche, 1987), both of which are incorporated herein by reference.

The term "pharmaceutically acceptable prodrugs", as used herein, refers to those prodrugs of the compounds in embodiments of the invention which are, within the scope of sound medical judgment, suitable for use in contact with the tissues of humans and lower mammals without undue toxicity, irritation, and allergic response, are commensurate with a reasonable benefit/risk ratio, and are effective for their intended use, as well as the zwitterionic forms, where possible, of the compounds of the invention. Other pharmaceutically acceptable prodrugs of this invention are prodrug esters of the C-31 hydroxyl group of compounds of this invention. In yet other embodiments, zotarolimus prodrugs include:

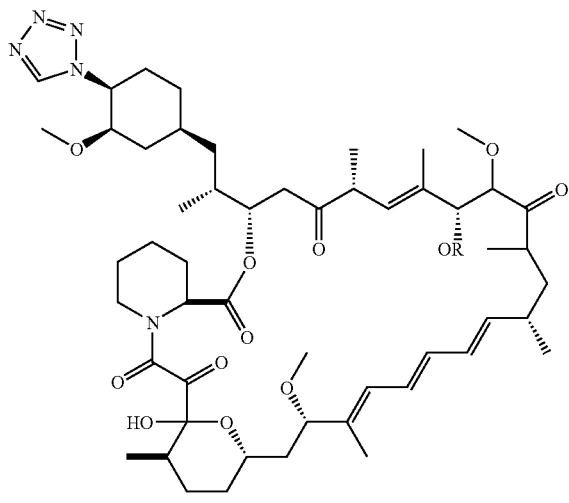

R=R¹C(O)R²R³; R¹C(S)R²R³

Where $R^1$=O,S $R^2$=nothing, 0, N, S, various alkyl, alkenyl, alkynyl, heterocycles, aryl $R^3$=nothing, various alkyl, alkenyl, alkynyl, heterocycles, aryl Alkyl, alkenyl, alkynyl, heterocycles, aryl groups can be substituted or unsubstituted The term "prodrug esters," as used herein, refers to any of several ester-forming groups that are hydrolyzed under physiological conditions. Examples of prodrug ester groups include acetyl, proprionyl, pivaloyl, pivaloyloxymethyl, acetoxymethyl, phthalidyl, methoxymethyl, indanyl, and the like, as well as ester groups derived from the coupling of naturally or unnaturally-occurring amino acids to the C-31 hydroxyl group of compounds of this invention.

The term "supporting structure" means a framework that is capable of including or supporting a pharmaceutically acceptable carrier or excipient, which carrier or excipient may include one or more therapeutic agents or substances, e.g., one or more drugs and/or other compounds. The supporting structure is typically formed of metal or a polymeric material. Suitable supporting structures formed of polymeric materials, including biodegradable polymers, capable of including the therapeutic agents or substances include, without limitation, those disclosed in U.S. Pat. Nos. 6,413,272 and 5,527,337, which are incorporated herein by reference (Igaki, 2002; Stack et al., 1996).

"Complementary" refers to the behavior exhibited by at least two drugs in combination where the overall pharmaceutical activities benefit from the combination. In some instances, such combinations have additive activity, while in others, they have separate, but beneficial activities, adding in the overall desired pharmacological effect in a subject, including a mammal and where the combination does not actively reduce either drugs biological activity.

"Subject" means a vertebrate including, but not limited to mammals, including a monkey, dog, cat, rabbit, cow, pig, goat, sheep, horse, rat, mouse, guinea pig, and human.

"Therapeutic substance" means any substance that when administered to a subject appropriately at an appropriate doses, has a beneficial effect on the subject.

Embodiments

In an embodiment of the invention is a compound of formula

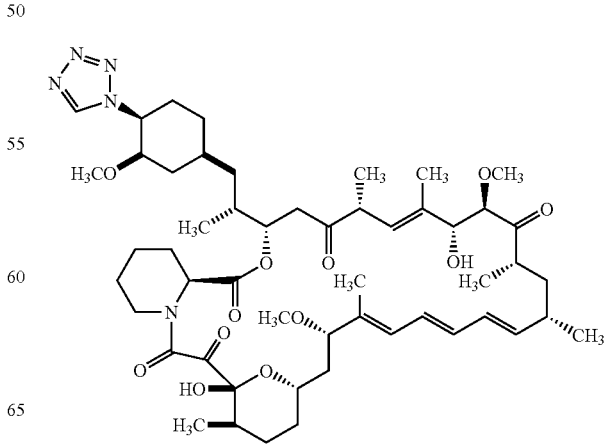

In another embodiment of the invention is a compound of formula

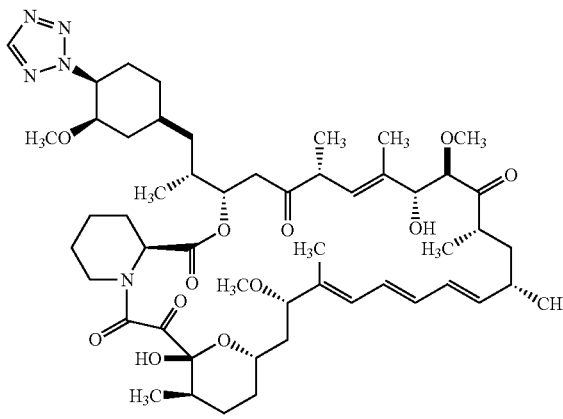

Preparation of Compounds of this Invention

The compounds and processes of embodiments of the invention will be better understood in connection with the following synthetic schemes which illustrate the methods by which the compounds of the invention may be prepared.

The compounds of this invention may be prepared by a variety of synthetic routes. A representative procedure is shown in Scheme 1.

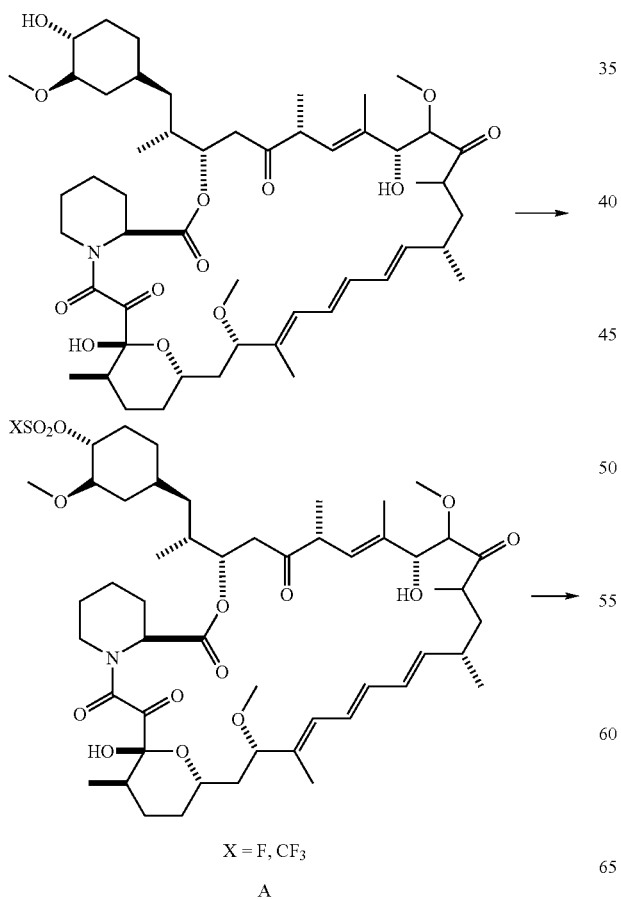

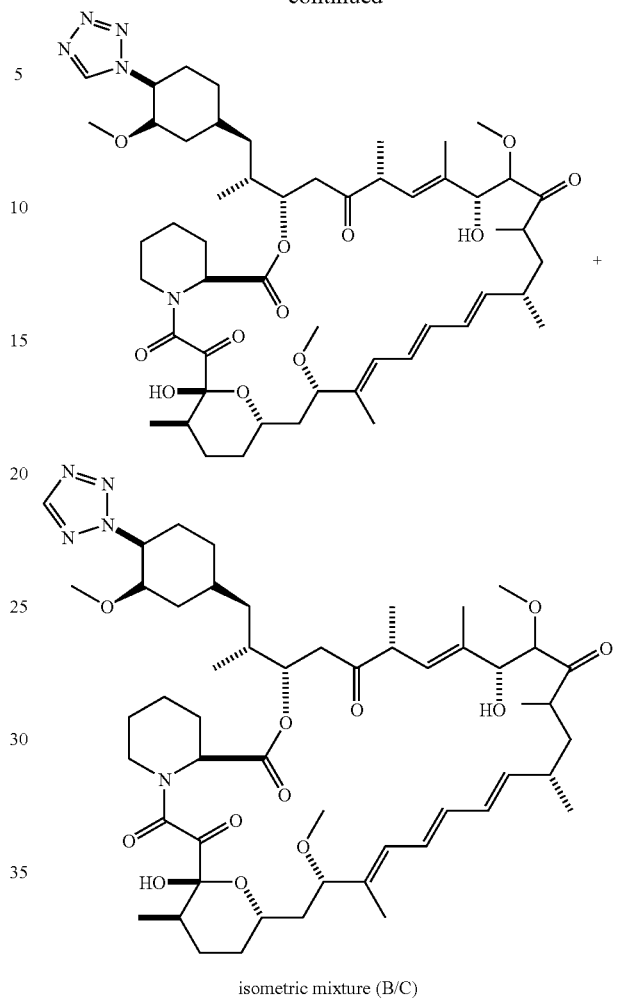

isometric mixture (B/C)

As shown in Scheme 1, conversion of the C-42 hydroxyl of rapamycin to a trifluoromethanesulfonate or fluorosulfonate leaving group provided A. Displacement of the leaving group with tetrazole in the presence of a hindered, non-nucleophilic base, including 2,6-lutidine, diisopropylethyl amine provided isomers B and C, which were separated and purified by flash column chromatography.

Synthetic Methods

The foregoing may be better understood by reference to the following examples which illustrate the methods by which the compounds of the invention may be prepared and are not intended to limit the scope of the invention as defined in the appended claims.

EXAMPLE 1

42-(2-tetrazolyl)-rapamycin (Less Polar Isomer)

Example 1A

A solution of rapamycin (100 mg, 0.11 mmol) in dichloromethane (0.6 mL) at −78° C. under a nitrogen atmosphere was treated sequentially with 2,6-lutidine (53 uL, 0.46 mmol, 4.3 eq.) and trifluoromethanesulfonic anhydride (37 uL, 0.22 mmol), and stirred thereafter for 15 minutes, warmed to room temperature and eluted through a pad of silica gel (6 mL) with diethyl ether. Fractions including the triflate were pooled and concentrated to provide the designated compound as an amber foam.

Example 1B 42-(2-tetrazolyl)-rapamycin (Less Polar Isomer)

A solution of Example 1A in isopropyl acetate (0.3 mL) was treated sequentially with diisopropylethylamine (87 mL, 0.5 mmol) and 1H-tetrazole (35 mg, 0.5 mmol), and thereafter stirred for 18 hours. This mixture was partitioned between water (10 mL) and ether (10 mL). The organics were washed with brine (10 mL) and dried ($Na_2SO_4$). Concentration of the organics provided a sticky yellow solid which was purified by chromatography on silica gel (3.5 g, 70-230 mesh) eluting with hexane (10 mL), hexane:ether (4:1(10 mL), 3:1(10 mL), 2:1(10 mL), 1:1(10 mL)), ether (30 mL), hexane:acetone (1:1(30 mL)). One of the isomers was collected in the ether fractions.

MS (ESI) m/e 966 (M)$^-$

EXAMPLE 2

42-(1-tetrazolyl)-rapamycin (More Polar Isomer)

Collection of the slower moving band from the chromatography column using the hexane:acetone (1:1) mobile phase in Example 1B provided the designated compound.

MS (ESI) m/e 966 (M)$^-$.

In vitro Assay of Biological Activity

The immunosuppressant activity of the compounds of embodiments of the invention were compared to rapamycin and two rapamycin analogs: 40-epi-N-[2'-pyridone]-rapamycin and 40-epi-N-[4'-pyridone]-rapamycin, both disclosed in (Or et al., 1996). The activity was determined using the human mixed lymphocyte reaction (MLR) assay described (Kino et al, 1987). The results of the assay demonstrate that the compounds of the invention are effective immunomodulators at nanomolar concentrations, as shown in Table 1.

TABLE 1

| Example | Human MLR $IC_{50}$ ± S.E.M.(nM) |
|---|---|
| Rapamycin | 0.91 ± 0.36 |
| 2-pyridone | 12.39 ± 5.3 |
| 4-pyridone | 0.43 ± 0.20 |
| Example 1 | 1.70 ± 0.48 |
| Example 2 | 0.66 ± 0.19 |

The pharmacokinetic behaviors of Example 1 and Example 2 were characterized following a single 2.5 mg/kg intravenous dose in cynomolgus monkey (n=3 per group). Each compound was prepared as 2.5 mg/mL solution in a 20% ethanol:30% propylene glycol:2% cremophor EL:48% dextrose 5% in water vehicle. The 1 mL/kg intravenous dose was administered as a slow bolus (~1-2 minutes) in a saphenous vein of the monkeys. Blood samples were obtained from a femoral artery or vein of each animal prior to dosing and 0.1 (IV only), 0.25, 0.5, 1, 1.5, 2, 4, 6, 9, 12, 24, and 30 hours after dosing. The EDTA preserved samples were thoroughly mixed and extracted for subsequent analysis.

An aliquot of blood (1.0 mL) was hemolyzed with 20% methanol in water (0.5 ml) including an internal standard.

The hemolyzed samples were extracted with a mixture of ethyl acetate and hexane (1:1 (v/v), 6.0 mL). The organic layer was evaporated to dryness with a stream of nitrogen at room temperature. Samples were reconstituted in methanol: water (1:1, 150 µL). The title compounds (50 µL injection) were separated from contaminants using reverse phase HPLC with UV detection. Samples were kept cool (4° C.) through the run. All samples from each study were analyzed as a single batch on the HPLC.

Area under the curve (AUC) measurements of Example 1, Example 2 and the internal standard were determined using the Sciex MacQuan™ software. Calibration curves were derived from peak area ratio (parent dr µg/internal standard) of the spiked blood standards using least squares linear regression of the ratio versus the theoretical concentration. The methods were linear for both compounds over the range of the standard curve (correlation>0.99) with an estimated quantitation limit of 0.1 ng/mL. The maximum blood concentration ($C_{max}$) and the time to reach the maximum blood concentration ($T_{max}$) were read directly from the observed blood concentration-time data. The blood concentration data were submitted to multi-exponential curve fitting using CSTRIP to obtain estimates of pharmacokinetic parameters. The estimated parameters were further defined using NONLIN84. The area under the blood concentration-time curve from 0 to t hours (last measurable blood concentration time point) after dosing ($AUC_{0-t}$) was calculated using the linear trapeziodal rule for the blood-time profiles. The residual area extrapolated to infinity, determined as the final measured blood concentration ($C_t$) divided by the terminal elimination rate constant (β), and added to $AUC_{0-t}$ to produce the total area under the curve ($AUC_{0-t}$)

As shown in FIG. 1 and Table 2, both Example 1 and Example 2 had a surprisingly substantially shorter terminal elimination half-life ($t_{1/2}$) when compared to rapamycin. Thus, only the compounds of the invention provide both sufficient efficacy (Table 1) and a shorter terminal half-life (Table 2).

TABLE 2

| Compound | AUC (ng · hr/mL) | $t_{1/2}$ (hours) |
|---|---|---|
| Rapamycin | 6.87 | 16.7 |
| 2-pyridone | 2.55 | 2.8 |
| 4-pyridone | 5.59 | 13.3 |
| Example 1 | 2.35 | 5.0 |
| Example 2 | 2.38 | 6.9 |

Methods of Treatment

The compounds of the invention, including but not limited to those specified in the examples, possess immunomodulatory activity in mammals (including humans). As immunosuppressants, the compounds of embodiments of the invention are useful for the treatment and prevention of immune-mediated diseases including the resistance by transplantation of organs or tissue including heart, kidney, liver, medulla ossium, skin, cornea, lung, pancreas, intestinum tenue, limb, muscle, nerves, duodenum, small-bowel, pancreatic-islet-cell, and the like; graft-versus-host diseases brought about by medulla ossium transplantation; autoimmune diseases including rheumatoid arthritis, systemic lupus erythematosus, Hashimoto's thyroiditis, multiple sclerosis, myasthenia gravis, Type I diabetes, uveitis, allergic encephalomyelitis, glomerulonephritis, and the like. Further uses include the treatment and prophylaxis of inflammatory and hyperproliferative skin diseases and cutaneous manifestations of immunologically-mediated illnesses, including psoriasis, atopic dermatitis, contact dermatitis and further eczematous dermatitises, seborrhoeis dermatitis, lichen planus, pemphigus, bullous pemphigoid, epidermolysis bullosa, urticaria, angioedemas, vasculitides, erythemas, cutaneous eosinophilias, lupus erythematosus, acne and alopecia areata; various eye diseases (autoimmune and otherwise) including keratoconjunctivitis, vernal conjunctivitis, uveitis associated with Behcet's disease, keratitis, herpetic keratitis, conical cornea, dystrophia epithelialis corneae, corneal leukoma, and ocular pemphigus. In addition reversible obstructive airway disease, which includes conditions including asthma (for example, bronchial asthma, allergic asthma, intrinsic asthma, extrinsic asthma and dust asthma), particularly chronic or inveterate asthma (for example, late asthma and airway hyper-responsiveness), bronchitis, allergic rhinitis, and the like are targeted by compounds of this invention. Inflammation of mucosa and blood vessels including gastric ulcers, vascular damage caused by ischemic diseases and thrombosis. Moreover, hyperproliferative vascular diseases including intimal smooth muscle cell hyperplasia, restenosis and vascular occlusion, particularly following biologically- or mechanically-mediated vascular injury, could be treated or prevented by the compounds of the invention.

The compounds or drugs described herein can be applied to stents that have been coated with a polymeric compound. Incorporation of the compound or drug into the polymeric coating of the stent can be carried out by dipping the polymer-coated stent into a solution including the compound or drug for a sufficient period of time (such as, for example, five minutes) and then drying the coated stent, such as, for example, by means of air drying for a sufficient period of time (such as, for example, 30 minutes). Other methods of applying therapeutic substances, including spraying, can be used. The polymer-coated stent including the compound or drug can then be delivered to the vessel lumen by deployment from a balloon catheter. In addition to stents, other devices that can be used to introduce the drugs of this invention to the vasculature include, but are not limited to grafts, catheters, and balloons. In addition, other compounds or drugs that can be used in lieu of the drugs of this invention include, but are not limited to, A-94507 and SDZ RAD (a.k.a. Everolimus).

Drug Combinations

The compounds described herein for use in polymer-coated stents can be used in combination with other pharmacological agents. The pharmacological agents that would, in combination with the compounds in embodiments of this invention, be effective in preventing restenosis can be classified into the categories of anti-proliferative agents, anti-platelet agents, anti-inflammatory agents, anti-thrombotic agents, and thrombolytic agents. These classes can be further sub-divided. For example, anti-proliferative agents can be anti-mitotic. Anti-mitotic agents inhibit or affect cell division, whereby processes normally involved in cell division do not take place. One sub-class of anti-mitotic agents includes vinca alkaloids. Representative examples of vinca alkaloids include, but are not limited to, vincristine, paclitaxel, etoposide, nocodazole, indirubin, and anthracycline derivatives, such as, for example, daunorubicin, daunomycin, and plicamycin. Other sub-classes of anti-mitotic agents include anti-mitotic alkylating agents, such as, for example, tauromustine, bofumustine, and fotemustine, and anti-mitotic metabolites, such as, for example, methotrexate, fluorouracil, 5-bromodeoxyuridine, 6-azacytidine, and cytarabine. Anti-mitotic alkylating agents affect cell division by covalently modifying DNA, RNA, or proteins, thereby inhibiting DNA replication, RNA transcription, RNA translation, protein synthesis, or combinations of the foregoing.

An example of an anti-mitotic agent includes, but is not limited to, paclitaxel. As used herein, paclitaxel includes the alkaloid itself and naturally occurring forms and derivatives thereof, as well as synthetic and semi-synthetic forms thereof.

Anti-platelet agents are therapeutic entities that act by (1) inhibiting adhesion of platelets to a surface, typically a thrombogenic surface, (2) inhibiting aggregation of platelets, (3) inhibiting activation of platelets, or (4) combinations of the foregoing. Activation of platelets is a process whereby platelets are converted from a quiescent, resting state to one in which platelets undergo a number of morphologic changes induced by contact with a thrombogenic surface. These changes include changes in the shape of the platelets, accompanied by the formation of pseudopods, binding to membrane receptors, and secretion of small molecules and proteins, such as, for example, ADP and platelet factor 4. Anti-platelet agents that act as inhibitors of adhesion of platelets include, but are not limited to, eptifibatide, tirofiban, RGD (Arg-Gly-Asp)-based peptides that inhibit binding to gpIIbIIIa or $\alpha v\beta 3$, antibodies that block binding to gpIIaIIIb or $\alpha v\beta 3$, anti-P-selectin antibodies, anti-E-selectin antibodies, compounds that block P-selectin or E-selectin binding to their respective ligands, saratin, and anti-von Willebrand factor antibodies. Agents that inhibit ADP-mediated platelet aggregation include, but are not limited to, disagregin and cilostazol.

Anti-inflammatory agents can also be used. Examples of these include, but are not limited to, prednisone, dexamethasone, hydrocortisone, estradiol, triamcinolone, mometasone, fluticasone, clobetasol, and non-steroidal anti-inflammatories, such as, for example, acetaminophen, ibuprofen, naproxen, adalimumab and sulindac. The arachidonate metabolite prostacyclin or prostacyclin analogs is an example of a vasoactive antiproliferative. Other examples of these agents include those that block cytokine activity or inhibit binding of cytokines or chemokines to the cognate receptors to inhibit pro-inflammatory signals transduced by the cytokines or the chemokines. Representative examples of these agents include, but are not limited to, anti-IL1, anti-IL2, anti-IL3, anti-IL4, anti-IL8, anti-IL15, anti-IL18, anti-MCP1, anti-CCR2, anti-GM-CSF, and anti-TNF antibodies.

Anti-thrombotic agents include chemical and biological entities that can intervene at any stage in the coagulation pathway. Examples of specific entities include, but are not limited to, small molecules that inhibit the activity of factor Xa. In addition, heparinoid-type agents that can inhibit both FXa and thrombin, either directly or indirectly, such as, for example, heparin, heparin sulfate, low molecular weight heparins, such as, for example, the compound having the trademark Clivarin®, and synthetic oligosaccharides, such as, for example, the compound having the trademark Arixtra®. Also included are direct thrombin inhibitors, such as, for example, melagatran, ximelagatran, argatroban, inogatran, and peptidomimetics of binding site of the Phe-Pro-Arg fibrinogen substrate for thrombin. Another class of anti-thrombotic agents that can be delivered are factor VII/VIIa inhibitors, such as, for example, anti-factor VII/VIIa antibodies, rNAPc2, and tissue factor pathway inhibitor (TFPI).

Thrombolytic agents, which may be defined as agents that help degrade thrombi (clots), can also be used as adjunctive agents, because the action of lysing a clot helps to disperse platelets trapped within the fibrin matrix of a thrombus. Representative examples of thrombolytic agents include, but are not limited to, urokinase or recombinant urokinase, pro-urokinase or recombinant pro-urokinase, tissue plasminogen activator or its recombinant form, and streptokinase.

Other drugs that can be used in combination with the compounds of this invention are cytotoxic drugs, such as, for example, apoptosis inducers, including TGF, and topoisomerase inhibitors, including, 10-hydroxycamptothecin, irinotecan, and doxorubicin. Other classes of drugs that can be used in combination with the compounds of this invention are drugs that inhibit cell de-differentiation and cytostatic drugs.

Other agents that can be used in combination with the compounds of this invention include anti-lipaedemic agents, including fenofibrate, matrix metalloproteinase inhibitors, such as, for example, batimistat, antagonists of the endothelin-A receptor, such as, for example, darusentan, and antagonists of the αvβ3 integrin receptor.

Other treatable conditions include but are not limited to ischemic bowel diseases, inflammatory bowel diseases, necrotizing enterocolitis, intestinal inflammations/allergies including Coeliac diseases, proctitis, eosinophilic gastroenteritis, mastocytosis, Crohn's disease and ulcerative colitis; nervous diseases including multiple myositis, Guillain-Barre syndrome, Meniere's disease, polyneuritis, multiple neuritis, mononeuritis and radiculopathy; endocrine diseases including hyperthyroidism and Basedow's disease; hematic diseases including pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases including osteoporosis; respiratory diseases including sarcoidosis, fibroid lung and idiopathic interstitial pneumonia; skin disease including dermatomyositis, leukoderma vulgaris, ichthyosis vulgaris, photoallergic sensitivity and cutaneous T cell lymphoma; circulatory diseases including arteriosclerosis, atherosclerosis, aortitis syndrome, polyarteritis nodosa and myocardosis; collagen diseases including scleroderma, Wegener's granuloma and Sjogren's syndrome; adiposis; eosinophilic fasciitis; periodontal disease including lesions of gingiva, periodontium, alveolar bone and substantia ossea dentis; nephrotic syndrome including glomerulonephritis; male pattern alopecia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury including ischemia-reperfusion injury of organs (including heart, liver, kidney and digestive tract) which occurs upon preservation, transplantation or ischemic disease (for example, thrombosis and cardiac infarction); intestinal diseases including endotoxin-shock, pseudomembranous colitis and colitis caused by drug or radiation; renal diseases including ischemic acute renal insufficiency and chronic renal insufficiency; pulmonary diseases including toxinosis caused by lung-oxygen or drug (for example, paracort and bleomycins), lung cancer and pulmonary emphysema; ocular diseases including cataracts, siderosis, retinitis, pigmentosa, senile macular degeneration, vitreal scarring and corneal alkali burn; dermatitis including erythema multiforme, linear IgA ballous dermatitis and cement dermatitis; and others including gingivitis, periodontitis, sepsis, pancreatitis, diseases caused by environmental pollution (for example, air pollution), aging, carcinogenesis, metastasis of carcinoma and hypobaropathy; diseases caused by histamine or leukotriene-$C_4$ release; Behcet's disease including intestinal-, vasculo- or neuro-Behcet's disease, and also Behcet's which affects the oral cavity, skin, eye, vulva, articulation, epididymis, lung, kidney and so on. Furthermore, the compounds of the invention are useful for the treatment and prevention of hepatic disease including immunogenic diseases (for example, chronic autoimmune liver diseases including autoimmune hepatitis, primary biliary cirrhosis and sclerosing cholangitis), partial liver resection, acute liver necrosis (e.g., necrosis caused by toxin, viral hepatitis, shock or anoxia), B-virus hepatitis, non-A/non-B hepatitis, cirrhosis (including alcoholic cirrhosis) and hepatic failure including fulminant hepatic failure, late-onset hepatic failure and "acute-on-chronic" liver failure (acute liver failure on chronic liver diseases), and moreover are useful for various diseases because of their potentially useful activity in augmention of the primary chemotherapeutic, antiviral, antiinflammatory, and cardiotonic effects of drugs the patient may already be taking.

Additionally, compounds of the invention possess FK-506 antagonistic properties. Embodiments of the compounds of the invention may thus be used in the treatment of immunodepression or a disorder involving immunodepression. Examples of disorders involving immunodepression include AIDS, cancer, fungal infections, senile dementia, trauma (including wound healing, surgery and shock) chronic bacterial infection, and certain central nervous system disorders. The immunodepression to be treated may be caused by an overdose of an immunosuppressive macrocyclic compound, for example derivatives of 12-(2-cyclohexyl-1-methylvinyl)-13,19,21,27-tetramethyl-11,28-dioxa-4-azatricyclo [22.3.1.0] octacos-18-ene including FK-506 or rapamycin. The overdosing of such medicaments by patients is quite common upon their realizing that they have forgotten to take their medication at the prescribed time and can lead to serious side effects.

The ability of the compounds of the invention to treat proliferative diseases can be demonstrated according to previously described methods (Bunchman and Brookshire, 1991; Shichiri et al., 1991; Yamagishi et al., 1993). Proliferative diseases include smooth muscle proliferation, systemic sclerosis, cirrhosis of the liver, adult respiratory distress syndrome, idiopathic cardiomyopathy, lupus erythematosus, diabetic retinopathy or other retinopathies, psoriasis, scleroderma, prostatic hyperplasia, cardiac hyperplasia, restenosis following arterial injury or other pathologic stenosis of blood vessels. In addition, these compounds antagonize cellular responses to several growth factors, and therefore possess antiangiogenic properties, making them useful agents to control or reverse the growth of certain tumors, as well as fibrotic diseases of the lung, liver, and kidney.

Aqueous liquid compositions of embodiments of the invention are particularly useful for the treatment and prevention of various diseases of the eye including autoimmune diseases (including, for example, conical cornea, keratitis, dysophia epithelialis corneae, leukoma, Mooren's ulcer, sclevitis and Graves' ophthalmopathy) and rejection of corneal transplantation.

When used in the above or other treatments, a therapeutically effective amount of one of the compounds in embodiments of the invention may be employed in pure form or, where such forms exist, in pharmaceutically acceptable salt, ester or prodrug form. Alternatively, the compound may be administered as a pharmaceutical composition including the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of embodiments of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds in embodiments of this invention administered to a human or lower animal may range from about 0.01 to about 10 mg/kg/day. For purposes of oral administration, doses may be in the range of from about 0.001 to about 3 mg/kg/day. For the purposes of local delivery from a stent, the daily dose that a patient will receive depends on the length of the stent. For example, a 15 mm coronary stent may include a drug in an amount ranging from about 1 to about 120 micrograms and may deliver that drug over a time period ranging from several hours to several weeks. If desired, the effective daily dose may be divided into multiple doses for purposes of administration; consequently, single dose compositions may include such amounts or submultiples thereof to make up the daily dose. Topical administration may involve doses ranging from 0.001 to 3 mg/kg/day, depending on the site of application.

Polymers

When used in embodiments of the invention, the coating can comprise any polymeric material in which the therapeutic agent, i.e., the drug, is substantially soluble. The purpose of the coating is to serve as a controlled release vehicle for the therapeutic agent or as a reservoir for a therapeutic agent to be delivered at the site of a lesion. The coating can be polymeric and can further be hydrophilic, hydrophobic, biodegradable, or non-biodegradable. The material for the polymeric coating can be selected from the group consisting of polyacrylates, polymethacrylates, polycarboxylic acids, cellulosic polymers, gelatin, polyvinylpyrrolidone, maleic anhydride polymers, polyamides, polyvinyl alcohols, polyethylene oxides, glycosaminoglycans, polysaccharides, polyesters, polyurethanes, silicones, polyorthoesters, polyanhydrides, polycarbonates, polypropylenes, polylactic acids, polyglycolic acids, polycaprolactones, polyhydroxybutyrate valerates, polyacrylamides, polyethers, and mixtures and copolymers of the foregoing. Coatings prepared from polymeric dispersions including polyurethane dispersions (BAYHYDROL, etc.) and acrylic acid latex dispersions can also be used with the therapeutic agents of embodiments of the invention.

Biodegradable polymers that can be used in this invention include polymers including poly(L-lactic acid), poly(DL-lactic acid), polycaprolactone, poly(hydroxy butyrate), polyglycolide, poly(diaxanone), poly(hydroxy valerate), polyorthoester; copolymers including poly (lactide-co-glycolide), polyhydroxy (butyrate-co-valerate), polyglycolide-co-trimethylene carbonate; polyanhydrides; polyphosphoester; polyphosphoester-urethane; polyamino acids; polycyanoacrylates; biomolecules including fibrin, fibrinogen, cellulose, starch, collagen and hyaluronic acid; and mixtures of the foregoing. Biostable materials that are suitable for use in this invention include polymers including polyurethane, silicones, polyesters, polyolefins, polyamides, polycaprolactam, polyimide, polyvinyl chloride, polyvinyl methyl ether, polyvinyl alcohol, acrylic polymers and copolymers, polyacrylonitrile, polystyrene copolymers of vinyl monomers with olefins (including styrene acrylonitrile copolymers, ethylene methyl methacrylate copolymers, ethylene vinyl acetate), polyethers, rayons, cellulosics (including cellulose acetate, cellulose nitrate, cellulose propionate, etc.), parylene and derivatives thereof; and mixtures and copolymers of the foregoing.

Other polymers that can be used in embodiments of this invention include, but are not limited to, those having the MPC subunit including poly($MPC_w$:$LAM_x$:$HPMA_y$:$TSMA_z$) where w, x, y, and z represent the molar ratios of monomers used in the feed for preparing the polymer and MPC represents the unit 2-methacryoyloxyethylphosphorylcholine, LMA represents the unit lauryl methacrylate, HPMA represents the unit 2-hydroxypropyl methacrylate, and TSMA represents the unit 3-trimethoxysilylpropyl methacrylate. The drug-impregnated stent can be used to maintain patency of a coronary artery previously occluded by thrombus and/or atherosclerotic plaque. The delivery of an anti-proliferative agent reduces the rate of in-stent restenosis.

Pharmaceutical Compositions

The pharmaceutical compositions of embodiments of the invention comprise a compound of the invention and a pharmaceutically acceptable carrier or excipient, which may be administered orally, rectally, parenterally, intracisternally, intravaginally, intraperitoneally, topically (as by powders, ointments, drops or transdermal patch), bucally, as an oral or nasal spray, or locally, as in a stent placed within the vasculature, or delivery to the pericardial space or into or onto the myocardium. The phrase "pharmaceutically acceptable carrier" means a non-toxic solid, semi-solid or liquid filler, diluent, encapsulating material or formulation auxiliary of any type. The term "parenteral," as used herein, refers to all modes of administration other than oral, which include intravenous, intraarterial, intramuscular, intraperitoneal, intrasternal, subcutaneous and intraarticular injection, infusion, transdermal, and placement, such as, for example, in the vasculature.

Pharmaceutical compositions of this invention for parenteral injection comprise pharmaceutically acceptable sterile aqueous or nonaqueous solutions, dispersions, suspensions, nanoparticulate suspensions, or emulsions as well as sterile powders for reconstitution into sterile injectable solutions or dispersions just prior to use. Examples of suitable aqueous and nonaqueous carriers, diluents, solvents or vehicles include water, ethanol, polyols (including glycerol, propylene glycol, polyethylene glycol, and the like), carboxymethylcellulose and suitable mixtures thereof, vegetable oils (including olive oil), and injectable organic esters including ethyl oleate. Proper fluidity can be maintained, for example, by the use of coating materials including lecithin, by the maintenance of the required particle size in the case of dispersions, and by the use of surfactants.

These compositions may also include adjuvants including preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents including sugars, sodium chloride, and the like. Prolonged absorption of the injectable pharmaceutical form may be brought about by the inclusion of agents that delay absorption including aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers including polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier including sodium citrate or dicalcium phosphate and/or (a) fillers or extenders including starches, lactose, sucrose, glucose, mannitol, and silicic acid, (b) binders such as, for example, carboxymethylcellulose, alginates, gelatin, polyvinylpyrrolidone, sucrose, and acacia, (c) humectants including glycerol, (d) disintegrating agents including agar-agar, calcium carbonate, potato or tapioca starch, alginic acid, certain silicates, and sodium carbonate, (e) solution retarding agents including paraffin, (f) absorption accelerators including quaternary ammonium compounds, (g) wetting agents such as, for example, cetyl alcohol and glycerol monostearate, (h) absorbents including kaolin and bentonite clay, and (i) lubricants including talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft, semi-solid and hard-filled gelatin capsules or liquid-filled capsules using such excipients as lactose or milk sugar as well as high molecular weight polyethylene glycols and the like.

The solid dosage forms of tablets, dragees, capsules, pills, and granules can be prepared with coatings and shells including enteric coatings and other coatings well known in the pharmaceutical formulating art. They may optionally include opacifying agents and can also be of a composition that they release the active ingredient(s) only, or in a certain part of the intestinal tract, optionally, in a delayed manner. Examples of embedding compositions that can be used include polymeric substances and waxes. Those embedding compositions including a drug can be placed on medical devices, including, but not limited to, stents, grafts, catheters, and balloons.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may include inert diluents commonly used in the art such as, for example, water or other solvents, solubilizing agents and emulsifiers including ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants including wetting agents, emulsifying and suspending agents, sweetening, flavoring, and perfuming agents.

Suspensions, in addition to the active compounds, may include suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically acceptable inert carrier comprising particles having a size, for example, of up to 100 micrometers in diameter. Suitable inert carriers include sugars including lactose. Desirably, at least 95% by weight of the particles of the active ingredient have an effective particle size in the range of 0.01 to 10 micrometers. Compositions for topical use on the skin also include ointments, creams, lotions, and gels.

Alternatively, the composition may be pressurized and include a compressed gas, including nitrogen or a liquefied gas propellant. The liquefied propellant medium and indeed the total composition is such that the active ingredient does not dissolve therein to any substantial extent, in embodiments of the invention. The pressurized composition may also include a surface active agent. The surface active agent may be a liquid or solid non-ionic surface active agent or may be a solid anionic surface active agent. In other embodiments, the use of the solid anionic surface active agent is in the form of a sodium salt.

A further form of topical administration is to the eye, as for the treatment of immune-mediated conditions of the eye including autoimmune diseases, allergic or inflammatory conditions, and corneal transplants. The compound of the invention is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/cilary, lens, choroid/retina and sclera. The pharmaceutically acceptable ophthalmic vehicle may, for example, be an ointment, vegetable oil or an encapsulating material.

In embodiments, compositions for rectal or vaginal administration include suppositories or retention enemas which can be prepared by mixing the compounds of this invention with suitable non-irritating excipients or carriers including cocoa butter, polyethylene glycol or a suppository wax which are solid at room temperature but liquid at body temperature and therefore melt in the rectum or vaginal cavity and release the active compound.

Compounds of embodiments of the invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. Compositions in embodiments of the invention are in liposome form and can include, in addition to a compound of the invention, stabilizers, preservatives, excipients, and the like. Lipids in embodiments of the invention are the phospholipids and the phosphatidyl cholines (lecithins), both natural and synthetic. Methods to form liposomes are known in the art. See, for example, (Prescott, 1976).

Compounds in embodiments of the invention may also be coadministered with one or more immunosuppressant agents. The immunosuppressant agents within the scope of this invention include, but are not limited to, IMURAN® azathioprine sodium, brequinar sodium, SPANIDIN® gusperimus trihydrochloride (also known as deoxyspergualin), mizoribine (also known as bredinin), CELLCEPT® mycophenolate mofetil, NEORAL® Cylosporin A (also marketed as different formulation of Cyclosporin A under the trademark SANDIMMUNE®), PROGRAF® tacrolimus (also known as FK-506), sirolimus and RAPAMUNE®, everolimus, leflunomide (also known as HWA-486), glucocorticoids, including prednisolone and its derivatives, antibody therapies including orthoclone (OKT3) and Zenapax®, and antithymyocyte globulins, including thymoglobulins.

Paclitaxel and Zotarolimus Co-administration Using a Stent

When paclitaxel is co-administered with zotarolimus using a stent implanted in a vessel, the ratio, r, of zotarolimus:paclitaxel by weight is such that the activity of one drug does not attenuate the activity of the other (i.e., interfere), and the overall effect of the co-administration is additive, and sometimes synergistic. Examples of useful ratios of zotarolimus:paclitaxel in embodiments of the invention are greater than approximately 10:7, approximately $10:7 \leq r \leq 10:0.01$, approximately $10:7 \leq r \leq 10:0.1$, and approximately r=10:1.

When applied on an implantable medical device, including a stent for blood vessel implantation, typical dosage of a therapeutic substance is 0.01 µg/mm to 100 1µg/mm. Typically, a practical maximum is dictated by the polymers, the drug, and the methods of making the device. While other dosages are effective and useful, when zotarolimus or paclitaxel are applied to the stent, typical dosages of each component in embodiments of the invention include, but are not limited to, 0.01 µg/mm to 50 µg/mm, 0.1 µg/mm to 30 µg/mm, and 1 µg/mm to 10 1µg/mm. However, any dosing regime can be used as long as the ratio of zotarolimus:paclitaxel is kept within approximately $10:7 \leq r \leq 10:0.01$, approximately $10:7 \leq r \leq 10:0.1$, and r=10:1 and biological safety is not significantly compromised. Examples of useful stents using zotarolimus and paclitaxel ratios include a 10:7 (zotarolimus:paclitaxel) stent including, but not limited to, 10 µg/mm of zotarolimus and 7 µg/mm of paclitaxel; and a 10:1 stent, wherein 10 µg/mm of zotarolimus is applied, and 1 µg/mm of paclitaxel is applied.

Popover Layers and Therapeutic Substances on Medical Devices

There is much flexibility in providing suitable drug-loaded polymer layers. For example, within therapeutic window parameters (generally levels between therapeutically effective and toxicity) associated with the drugs of interest, ratios of the drugs used in combination can be varied relative to each other. For example, an embodiment has a 90:10 total drug:polymer ratio with where the ratio of drugs in the combination can be 1:1. Thus, a stent delivering a zotarolimus/paclitaxel combination can include 10 µg/mm zotarolimus and 10 µg/mm paclitaxel in a PC polymer layer with a 5 µg/mm PC topcoat. Total drug:polymer ratio can be lower, however, e.g., 40:60 or less. Upper limits on the total amount of drug will depend on several factors, including miscibility of the selected drugs in the selected polymer, the stability of the drug/polymer mixture, e.g., compatibility with sterilization, and the physical properties of the mixture, e.g., flowability/processability, elasticity, brittleness, viscosity (does not web or bridge between stent struts), coating thickness that adds substantially to the stent profile or causes delamination or cracking or is difficult to crimp. Embodiments of the invention include stent struts spaced about 60-80 microns apart, suggesting an upper limit in thickness of the drug/polymer/polymer overcoat is about 30 microns; however, any stent size, strut size and spatial spacing, and/or stent construction can be utilized for drug delivery as described therein.

Overcoat thickness (if an overcoat is used) desirably should not excessively impede release kinetics of the drugs.

Generally speaking, drugs useful in combinations for embodiments of the invention will not adversely affect the desired activity of the other drug in the combination. Thus, one drug in the proposed combination will not inhibit the desired activity, e.g., anti-proliferative activity, of the other drug. Nor will either drug cause or enhance the degradation of the other drug. However, a drug that might otherwise appear to be unsuitable because, for example, it degrades during sterilization; can in fact be useful because it is stabilized by interaction of another drug.

Testing for Safety and Efficacy After Stent Implantation

This model can be used to predict treatment for restenosis in human vasculature. The test exploits the art-accepted porcine coronary overstretch model (Schwartz, 1992) and is usually conducted for approximately 2-8 weeks. Typically, experimental construction includes at least a stent control that resembles the experimental stent in every way except for the change of a single variable, including a therapeutic substance or polymer.

In one example, two major coronary arteries are implanted with one test stent each, and the third major coronary artery is implanted with a control stent in each pig. Stents should be the same dimensions, or as close as possible.

Stents are implanted using standard techniques. At the conclusion of the study, animals are euthanized, and the hearts are removed, washed and fixed using standard histological preservation techniques (including formalin, formaldehyde, etc). Stented vessels are excised, then infiltrated and embedded in a suitable medium for sectioning, including methylmethacrylate (MMA), paraffin, or cryomedia. All blocks including stented vessels are sectioned so that informative sections are obtained; for example, three, in-stent sections and two control sections. Ser. thin sections (approximately 5 µm) are usually taken at each level and stained to visualize the cells and tissues (e.g., hematoxylin and eosin (HE) and Masson's Verhoeff Elastin (MVE)). Sections are evaluated and scored using an image analysis system or other art accepted methods of morphological data collection and quantification. The data are scored for neointimal area, neointimal thickness, and percent-area stenosis.

EXAMPLE 3

The purpose of this example was to determine the effects of a rapamycin analog on neointimal formation in porcine coronary arteries including stents. This example illustrates that the rapamycin analog zotarolimus, when compounded and delivered from the Biocompatibles BiodiviYsio PC Coronary stent favorably affects neointimal hyperplasia and lumen size in porcine coronary arteries. This finding suggests that a combination from a drug-eluting stent including zotarolimus may be of substantial clinical benefit if properly applied in humans by limiting neointimal hyperplasia.

The agent zotarolimus is a rapamycin analog. The study set forth in this example was designed to assess the ability of the rapamycin analog zotarolimus to reduce neointimal hyperplasia in a porcine coronary stent model. Efficacy of zotarolimus in this model would suggest its clinical potential for the limitation and treatment of coronary restenosis in stents following percutaneous revascularization. The domestic swine was used because this model appears to yield results comparable to other investigations seeking to limit neointimal hyperplasia in human subjects.

The example tested zotarolimus eluted from coronary stents placed in juvenile farm pigs, and compared these results with control stents. The control stents are polymer-coated without drugs. This is important, for the polymer itself must not stimulate neointimal hyperplasia to a substantial degree. As the eluted drug disappears, an inflammatory response to the polymer could conceivably result in a late "catch-up phenomenon" where the restenosis process is not stopped, but instead slowed. This phenomenon could result in restenosis at late dates in human subjects.

Stents were implanted in two blood vessels in each pig. Pigs used in this model were generally 2-4 months old and weighed 30-40 Kg. Two coronary stents were thus implanted in each pig by visually assessing a normal stent:artery ratio of 1.1-1.2.

Beginning on the day of the procedure, pigs were given oral aspirin (325 mg daily) and continued for the remainder of their course. General anesthesia was achieved by means of intramuscular injection followed by intravenous ketamine (30 mg/kg) and xylazine (3 mg/kg). Additional medication at the time of induction included atropine (1 mg) and flocillin (1 g) administered intramuscularly. During the stenting procedure, an intraarterial bolus of 10,000 units of heparin was administered.

Arterial access was obtained by cutdown on the right external carotid and placement of an 8F sheath. After the procedure, the animals were maintained on a normal diet without cholesterol or other special supplementation.

Figure 2:
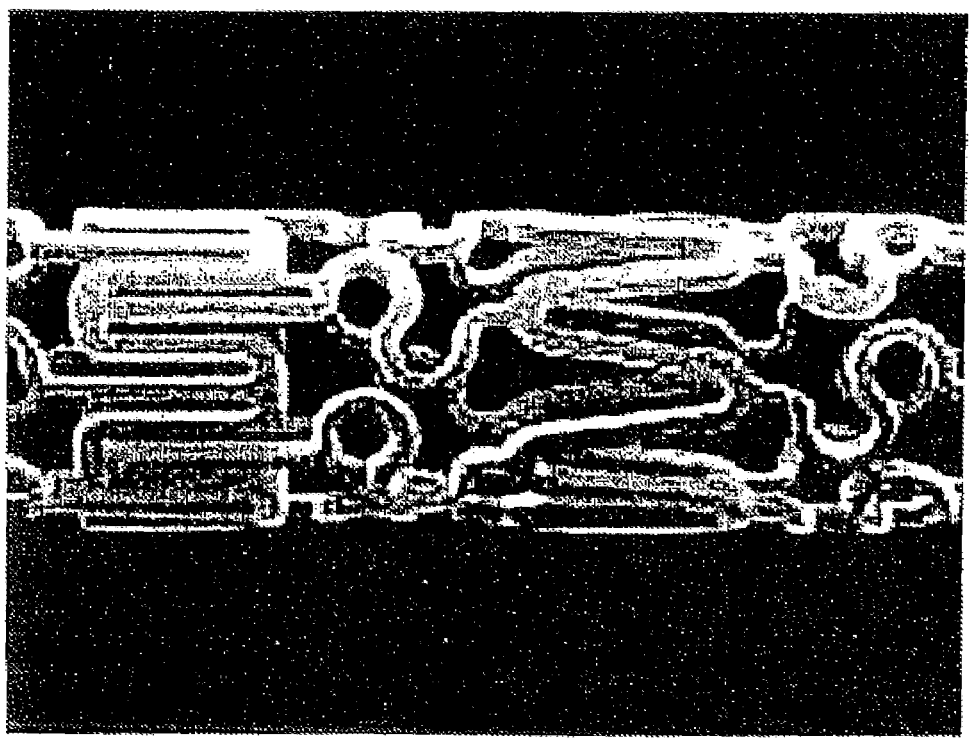
FIG. 2 is a side view in elevation showing a stent suitable for use in this invention.

The BiodivYsio stent was used with nominal vessel target size of 3.0 mm. See FIG. 2. Two coronary arteries per pig were assigned at random to deployment of the stents. The stent was either a drug eluting stent (polymer plus drug stent) or a stent coated with a polymer only (polymer only stent). The stents were delivered by means of standard guide catheters and wires. The stent balloons were inflated to appropriate sizes for less than 30 seconds.

Each pig had one polymer only stent and one polymer plus drug stent placed in separate coronary arteries, so that each pig would have one stent for drug and one for control.

A sample size of 20 pigs total was chosen to detect a projected difference in neointimal thickness of 0.12 mm with a standard deviation of 0.15 mm, at a power of 0.95 and alpha 0.05.

Animals were euthanized at 28 days for histopathologic examination and quantification. Following removal of the heart from the perfusion pump system, the left atrial appendage was removed for access to the proximal coronary arteries. Coronary arterial segments with injuries were dissected free of the epicardium. Segments including lesions were isolated, thereby allowing sufficient tissue to include uninvolved blood vessel at either end. The foregoing segments, each roughly 2.5 cm in length, were embedded and processed by means of standard plastic embedding techniques. The tissues were subsequently processed and stained with hematoxylin-eosin and elastic-van Gieson techniques.

Low and high power light microscopy were used to make length measurements in the plane of microscopic view by means of a calibrated reticle and a digital microscopy system connected to a computer employing calibrated analysis software.

The severity of vessel injury and the neointimal response were measured by calibrated digital microscopy. The importance of the integrity of the internal elastic lamina is well-known to those skilled in the art. A histopathologic injury score in stented blood vessels has been validated as being closely related to neointimal thickness. This score is related to depth of injury and is as follows:

| Score | Description of Injury |
|---|---|
| 0 | Internal elastic lamina intact; endotheium typically denuded, media compressed but not lacerated. |
| 1 | Internal elastic lamina lacerated; media typically compressed but not lacerated. |
| 2 | Internal elastic lacerated; media visibly lacerated; external elastic lamina intact but compressed. |
| 3 | External elastic lamina lacerated; typically large lacerations of media extending through the external elastic lamina; coil wires sometimes residing in adventitia. |

This quantitative measurement of injury was assessed for all stent struts of each stent section. The calibrated digital image was also used to measure at each stent struts site the neointimal thickness. Lumen area, area included with the internal elastic lamina, and area within the external elastic lamina were also measured.

The neointimal thickness measured for each strut in a given section then averaged to determine the neointimal thickness for the section.

The mid-stent segment was used for measurement, analysis, and comparison. Data were also recorded (and included in the data section of this report) for proximal and distal segments.

The data analysis methods for this study did not need to take into account variable arterial injury across treatment/control groups, because mild to moderate injury is sensitive enough to detect treatment differences. Paired t-testing was performed to compare variables across the polymer only stents (control group) and polymer plus drug stents (treatment group). No animal died in this study before scheduled timepoints.

Table 3 shows the pigs and arteries used. In Table 3, LCX means the circumflex branch of the left coronary artery, LAD means the left anterior descending coronary artery, and RCA means the right coronary artery.

TABLE 3

Pigs and Vessels Used

| | | |
|---|---|---|
| 1 | 2000-G-693 | RCA - Control |
| | 2000-G-693 | LCX - Test |
| 2 | 2000-G-698 | RCA - Test |
| | 2000-G-698 | LAD - Control |
| 3 | 2000-G-702 | RCA - Test |
| | 2000-G-702 | LAD - Control |
| 4 | 2000-G-709 | RCA - Control |
| | 2000-G-709 | LAD - Test |
| 5 | 2000-G-306 | RCA - Control |
| | 2000-G-306 | LAD - Test |
| | 2000-G-306 | *LCX - Test |
| 6 | 2000-G-672 | RCA - Test |
| | 2000-G-672 | LAD - Control |
| 7 | 2000-G-712 | RCA - Control |
| | 2000-G-712 | LCX - Test |
| 8 | 2000-G-735 | RCA - Control |
| | 2000-G-735 | LAD - Test |
| 9 | 2000-G-736 | RCA - Control |
| | 2000-G-736 | LCX - Test |
| 10 | 2000-G-740 | RCA - Test |
| 11 | 2000-G-742 | LAD - Test |
| | 2000-G-742 | OM (LCX) - Control |
| 12 | 2000-G-744 | RCA - Test |
| | 2000-G-744 | LAD - Control |
| 13 | 2000-G-748 | RCA - Test |
| | 2000-G-748 | LAD - Control |
| 14 | 2000-G-749 | RCA - Control |
| | 2000-G-749 | LCX - Test |
| 15 | 2000-G-753 | RCA - Control |
| | 2000-G-753 | LAD - Test |
| 16 | 2000-G-754 | RCA - Test |
| | 2000-G-754 | LCX - Control |
| 17 | 2000-G-755 | RCA - Control |
| | 2000-G-755 | LAD - Test |
| 18 | 2000-G-756 | RCA - Test |
| | 2000-G-756 | LAD - Control |
| 19 | 2000-G-757 | LAD - Control |
| | 2000-G-757 | LCX - Test |
| 20 | 2000-G-760 | LAD - Test |
| | 2000-G-760 | LCX - Control |

Table 4 shows the summary results for all data for mean injury and neointimal thicknesss for each stent, including proximal, mid, and distal segments. Table 4 also shows lumen size, percent stenosis, and artery size as measured by the internal elastic laminae (IEL) external elastic laminae (EEL).

TABLE 4

Summary: All Measures (Distal, Mid, Proximal)

| ID | prox ref | dist ref | lumen | IEL | EEL | mean injury | % stenosis | Neointimal area | NIT |
|---|---|---|---|---|---|---|---|---|---|
| Control Distal | | | | | | | | | |
| Mean | 4.46 | 3.96 | 4.88 | 7.66 | 9.00 | 0.22 | 36.10 | 2.79 | 0.41 |
| SD | 1.20 | 1.16 | 1.30 | 1.15 | 1.10 | 0.26 | 15.41 | 1.29 | 0.17 |
| Control Mid | | | | | | | | | |
| Mean | 4.46 | 3.96 | 4.94 | 7.71 | 9.08 | 0.08 | 36.23 | 2.77 | 0.38 |
| SD | 1.20 | 1.16 | 1.44 | 1.07 | 1.15 | 0.14 | 14.93 | 1.20 | 0.16 |
| Control Proximal | | | | | | | | | |
| Mean | 4.46 | 3.96 | 5.11 | 7.89 | 9.30 | 0.15 | 35.35 | 2.78 | 0.38 |
| SD | 1.20 | 1.16 | 1.38 | 1.33 | 1.42 | 0.22 | 11.94 | 1.04 | 0.12 |
| Test Distal | | | | | | | | | |
| Mean | 4.26 | 3.41 | 6.04 | 7.70 | 9.01 | 0.26 | 22.35 | 1.66 | 0.25 |
| SD | 1.26 | 0.96 | 1.55 | 1.49 | 1.47 | 0.43 | 8.58 | 0.58 | 0.06 |
| Test Mid | | | | | | | | | |
| Mean | 4.26 | 3.41 | 6.35 | 7.75 | 8.98 | 0.04 | 18.71 | 1.41 | 0.22 |
| SD | 1.26 | 0.96 | 1.29 | 1.18 | 1.31 | 0.07 | 5.68 | 0.33 | 0.05 |
| Test Proximal | | | | | | | | | |
| Mean | 2.56 | 2.15 | 3.31 | 4.06 | 4.66 | 0.19 | 16.79 | 1.29 | 0.18 |
| SD | 1.66 | 1.37 | 2.39 | 3.48 | 4.15 | 0.13 | 9.97 | 0.80 | 0.12 |

There was no statistically significant difference for neointimal area or thickness across proximal, mid, or distal segments within the test group (polymer plus drug stents) or control groups (polymer only stents). This observation is quite consistent with prior studies, and thus allows use of only the mid segment for statistical comparison of test devices (polymer plus drug stents) vs. control devices (polymer only stents).

Table 5 shows the statistical t-test comparisons across test groups and control groups. There was a statistically significant difference in neointimal thickness, neointimal area, lumen size, and percent lumen stenosis, the drug eluting stent being clearly favored. Conversely, there were no statistically significant differences between the test group (polymer plus drug stents) and the control group (polymer only stents) for mean injury score, external elastic laminae, or internal elastic laminae areas.

TABLE 5

Statistical Comparison of Test vs. Control Parameters: Mid-Section Data (t-test Statistics)

| Parameter | Difference | t-test | DF | Std Error | Lower 95% | Upper 95% | p |
|---|---|---|---|---|---|---|---|
| Lumen | −1.17 | −2.28 | 38 | 0.52 | −2.21 | −0.13 | 0.029 |
| IEL | 0.03 | 0.088 | 38 | 0.36 | −0.71 | 0.78 | 0.93 |
| EEL | 0.2 | 0.499 | 38 | 0.39 | −0.599 | 0.99 | 0.62 |
| NI Thickness | 0.18 | 5.153 | 38 | 0.034 | 0.106 | 0.244 | <.0001 |
| NI Area | 1.21 | 3.62 | 38 | 0.33 | 0.53 | 1.88 | 0.0008 |
| Mean Injury | 0.038 | 1.137 | 38 | 0.033 | −0.02 | 0.106 | 0.26 |
| % Stenosis | 14.54 | 2.97 | 38 | 4.9 | 4.61 | 24.47 | 0.005 |

Figure 3A:
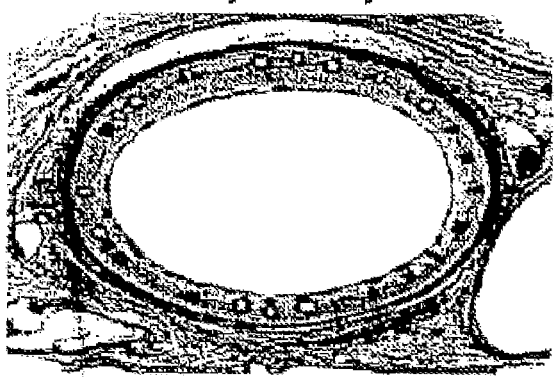
FIG. 3A is a cross-sectional view of a vessel segment in which was placed a stent coated with a polymer only.
Figure 3B:
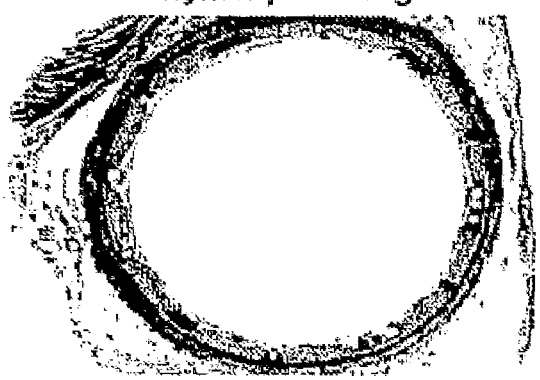
FIG. 3B is a cross-sectional view of a vessel segment in which was placed a stent coated with a polymer plus drug.

The reference arteries proximal and distal to the stented segments were observed, and quantitated. These vessels appeared normal in all cases, uninjured in both the control group (polymer only stents) and the test group (polymer plus drug stents). See FIGS. 3A and 3B. The data below show there were no statistically significant differences in size between the stents in the control group and the stents in the test group.

|  | Proximal Reference Diameter (mm) | Distal Reference Diameter (mm) |
|---|---|---|
| Control (mean ± SD) | 4.46 ± 1.20 | 3.96 ± 1.16 |
| Test (mean ± SD) | 4.26 ± 1.26 | 3.41 ± 0.96 |

The data demonstrates that statistically significant differences exist, favoring the stent that elutes zotarolimus. The stent of this invention results in lower neointimal area, lower neointimal thickness, and greater lumen area. There were no significant differences within the test group (polymer plus drug stents) and the control group (polymer only stents) for inflammation or injury parameters. There were no significant differences in artery sizes (including the stent) for the control group compared to the test group. These latter findings suggest no significant difference in the arterial remodeling characteristics of the polymeric coating including the drug.

At most, mild inflammation was found on both the polymer plus drug stent and the polymer only stent. This finding suggests that the polymer exhibits satisfactory biocompatibility, even without drug loading. Other studies show that when drug has completely gone from the polymer, the polymer itself creates enough inflammation to cause neointima. This phenomenon may be responsible for the late catch-up phenomenon of clinical late restenosis. Because the polymer in this example did not cause inflammation in the coronary arteries, late problems related to the polymer after the drug is exhausted are unlikely.

In conclusion, a stent eluting the compound zotarolimus from a polymer coating showed a reduction in neointimal hyperplasia in the porcine model when placed in a coronary artery.

EXAMPLE 4

The purpose of this example is to determine the rate of release of the zotarolimus drug from 316L Electropolished Stainless Steel Coupons coated with a biocompatible polymer including phosphorylcholine side groups.

Rubber septa from lids from HPLC vials were removed from the vials and placed into glass vials so that the "Teflon" side faced up. These septa served as supports for the test samples. The test samples were 316L stainless steel coupons that had been previously coated with a biocompatible polymer including phosphorylcholine side groups (PC polymer). Coronary stents are commonly made of 316L stainless steel and can be coated with the PC polymer to provide a depot site for loading drugs. The coated coupons, which serve to simulate stents, were placed onto the septa. By using a glass Hamilton Syringe, a solution of zotarolimus and ethanol (10 $\mu$l) was applied to the surface of each coupon. The solution included zotarolimus (30.6 mg) dissolved in 100% ethanol (3.0 ml). The syringe was cleaned with ethanol between each application. The cap to the glass vial was placed on the vial loosely, thereby assuring proper ventilation. The coupon was allowed to dry for a minimum of 1.5 hours. Twelve (12) coupons were loaded in this way—six being used to determine the average amount of drug loaded onto the device and six being used to measure the time needed to release the drug from the devices.

To determine the total amount of zotarolimus loaded onto a coupon, a coupon was removed from the vial and placed into 50/50 acetonitrile/0.01 M phosphate buffer (pH 6.0, 5.0 ml). The coupon was placed onto a 5210 Branson soricator for one hour. The coupon was then removed from the solution, and the solution was assayed by HPLC.

The time release studies were performed by immersing and removing the individual coupons from fresh aliquots (10.0 ml) of 0.01 M phosphate buffer at a pH of 6.0 at each of the following time intervals—5, 15, 30 and 60 minutes. For the remaining time points of 120, 180, 240, 300, 360 minutes, volumes of 5.0 ml of buffer were used. To facilitate mixing during the drug release phase, the samples were placed onto an Eberbach shaker set at low speed. All solution aliquots were assayed by HPLC after the testing of the last sample was completed.

The HPLC analysis was performed with a Hewlett Packard series 1100 instrument having the following settings:

| | |
|---|---|
| Injection Volume = | 100 µl |
| Acquisition Time = | 40 minutes |
| Flow Rate = | 1.0 ml/min |
| Column Temperature = | 40 °C |
| Wavelength = | 278 nm |
| Mobile Phase = | 65% Acetonitrile/35% $H_2O$ |
| Column = | YMC ODS-A S5 µm, 4.6 × 250 mm Part No. A12052546WT |

The results from the above experiment showed the following release data (Table 6):

TABLE 6

| Time (min.) | Percent Release | Standard Deviation |
|---|---|---|
| 0.00 | 0.00 | 0.00 |
| 5.00 | 1.87 | 1.12 |
| 15.00 | 2.97 | 1.47 |
| 30.00 | 3.24 | 1.28 |
| 60.00 | 3.29 | 1.29 |
| 120.00 | 3.92 | 1.28 |
| 180.00 | 4.36 | 1.33 |
| 240.00 | 4.37 | 1.35 |
| 300.00 | 6.34 | 2.07 |
| 360.00 | 7.88 | 1.01 |

EXAMPLE 5

The purpose of this example was to determine the loading and release of zotarolimus from 15 mm BiodivYsio drug delivery stents.

To load the stents with drug, a solution of zotarolimus in ethanol at a concentration of 50 mg/ml was prepared and dispensed into twelve vials. Twelve individual polymer-coated stents were placed on fixtures designed to hold the stent in a vertical position and the stents were immersed vertically in the drug solution for five minutes. The stents and fixtures were removed from the vials and excess drug solution was blotted away by contacting the stents with an absorbent material. The stents were then allowed to dry in air for 30 minutes in an inverted vertical position.

The stents were removed from the fixtures, and each stent was placed into 50/50 acetonitrile/phosphate buffer (pH 5.1, 2.0 ml) and sonicated for one hour. The stents were removed from the solution and solutions were assayed for concentration of drug, which allowed calculation of the amount of drug originally on the stents. This method was independently shown to remove at least 95% of the drug from the stent coating. On average, the stents included 120±9 micrograms of drug.

The drug-loaded stents were placed on the fixtures and placed into 0.01 M phosphate buffer (pH=6.0, 1.9 ml) in individual vials. These samples were placed onto a Eberbach shaker set at low speed to provide back-and-forth agitation. To avoid approaching drug saturation in the buffer, the stents were transferred periodically to fresh buffer vials at the following points: 15, 30, 45, 60, 120, 135, 150, 165, 180, 240, 390 minutes. The dissolution buffer vials were assayed by HPLC for the drug concentration at the end of the drug release period studied. The data, represented as % cumulative release of the drug as a function of time, is shown in tabular form below (Table 7):

TABLE 7

| Time (min) | % Cumulative Release of Drug |
|---|---|
| 15 | 0.3 |
| 30 | 1.1 |
| 45 | 2.1 |
| 60 | 3.2 |
| 120 | 4.3 |
| 135 | 5.9 |
| 150 | 6.3 |
| 165 | 6.8 |
| 180 | 7.4 |
| 240 | 10.8 |
| 390 | 13.2 |

EXAMPLE 6

Zotarolimus, a tetrazole analog of rapamycin, has been shown to possess anti-restenosis activity in swine coronary stent-induced injury Schwartz, R. S. Efficacy Evaluation of a Rapamycin Analog (A-179578) Delivered from the Biocompatibles BiodivYsio PC Coronary Stents in Porcine Coronary Arteries, Technical Report, Mayo Clinic and Foundation, Rochester, Minn. The objective of this example was to assess the safety and pharmacokinetics (PK) of escalating single intravenous (IV) doses of zotarolimus in healthy males.

In the present, first-time-in-man study, the safety and pharmacokinetics of zotarolimus were investigated following intravenous bolus administration of zotarolimus over a 100 to 900 µg dose range. The intravenous bolus dose administration would mimic the most rapid unexpected release of zotarolimus from drug-coated stents in vivo.

This was a Phase 1, single escalating dose, double-blind, randomized, placebo-controlled, single-center study. Sixty (60) adult healthy males were divided into 5 IV dose groups of 100, 300, 500, 700, and 900 µg. Demographic information for the subjects is summarized in Table 9.

TABLE 9

Demographic Summary for All Subjects

| | Mean ± SD (N = 60) | Min-Max |
|---|---|---|
| Age (years) | 32.6 ± 7.1 | 19-44 |
| Weight (kg) | 80.0 ± 10.6 | 62-104 |
| Height (cm) | 180.5 ± 7.2 | 160-195 |
| Race | 60 Caucasians (100%) | |

Subjects were randomly assigned to receive a single intravenous dose of zotarolimus or a matching intravenous placebo under fasting conditions, as shown in the dosing scheme shown in Table 10.

TABLE 10

| Treatment Group | Double-blind Treatment | Number of Subjects |
|---|---|---|
| I | 100 µg zotarolimus/Placebo | 8/4 |
| II | 300 µg zotarolimus/Placebo | 8/4 |
| III | 500 µg zotarolimus/Placebo | 8/4 |
| IV | 700 µg zotarolimus/Placebo | 8/4 |
| V | 900 µg zotarolimus/Placebo | 8/4 |

Higher doses were administered after evaluating the safety data from the preceding lower dose groups. The treatment groups were separated by at least 7 days. For safety reasons, each treatment group was divided into two cohorts of six subjects and the doses of the two cohorts of a group were separated by at least 1 day.

Doses were administered as IV bolus over 3 minutes, with 8 subjects. Four subjects received zotarolimus and 4 subjects received placebo in each dose group. Blood concentrations of zotarolimus were sampled for 168 hours and measured using LC-MS/MS with a LOQ of 0.20 ng/mL Seven (7)-mL blood samples were collected by venipuncture into evacuated collection tubes including edetic acid (EDTA) prior to dosing (0 hour) and at 0.083 (5 min), 0.25, 0.5, 1, 2, 4, 8, 12, 16, 24, 36, 48, 72, 96, 120, 144, and 168 hours after dosing on Study Day 1.

Blood concentrations of zotarolimus were determined using a validated liquid/liquid extraction HPLC tandem mass spectrometric method (LC-MS/MS) (Ji et al., 2004). The lower limit of quantification of zotarolimus was 0.20 ng/mL using 0.3 mL blood sample. All calibration curves had coefficient of determination ($r^2$) values greater than or equal to 0.9923.

Safety was evaluated based on adverse event, physical examination, vital signs, ECG, injection site and laboratory tests assessments.

Pharmacokinetic parameter values of zotarolimus were estimated using noncompartmental methods. These parameters included: concentration at 5-minutes zotarolimus post-dose ($C_5$), dose-normalized $C_5$, elimination rate constant ($\beta$), half-life ($t_{1/2}$), the area under the blood concentration vs. time curve from time 0 to time of the last measurable concentration ($AUC_{0\text{-}last}$), dose-normalized $AUC_{0\text{-}last}$, the area under the blood concentration vs. time curve extrapolated to infinite time ($AUC_{0\text{-}inf}$), dose-normalized $AUC_{0\text{-}inf}$, total clearance (CL), and volume of distribution ($Vd_\beta$).

Figure 4:
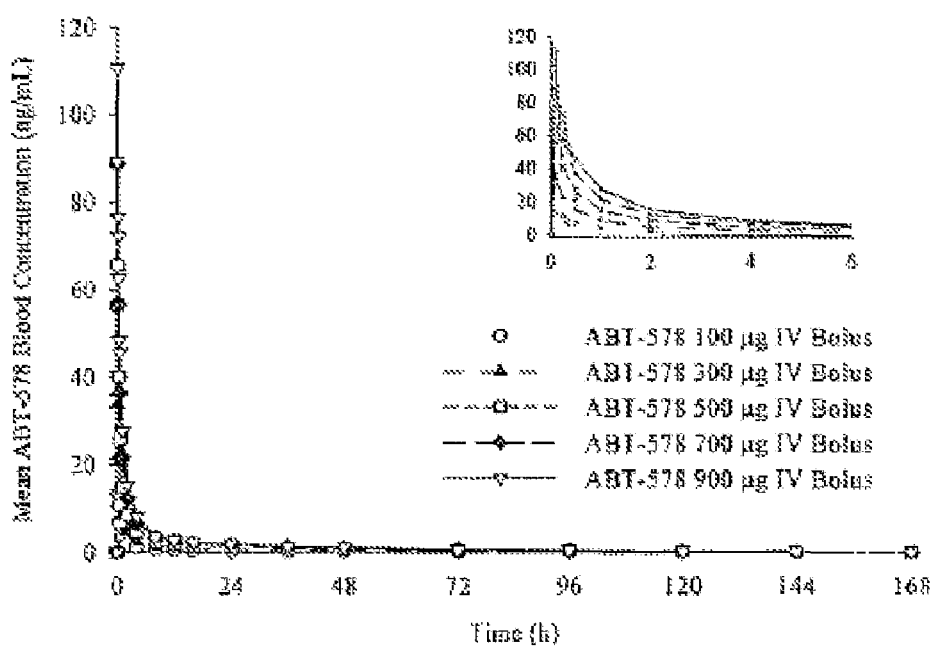
FIG. 4 shows on a linear scale mean blood-concentration—time plot for single escalating intravenous doses of zotarolimus in humans.
Figure 5:
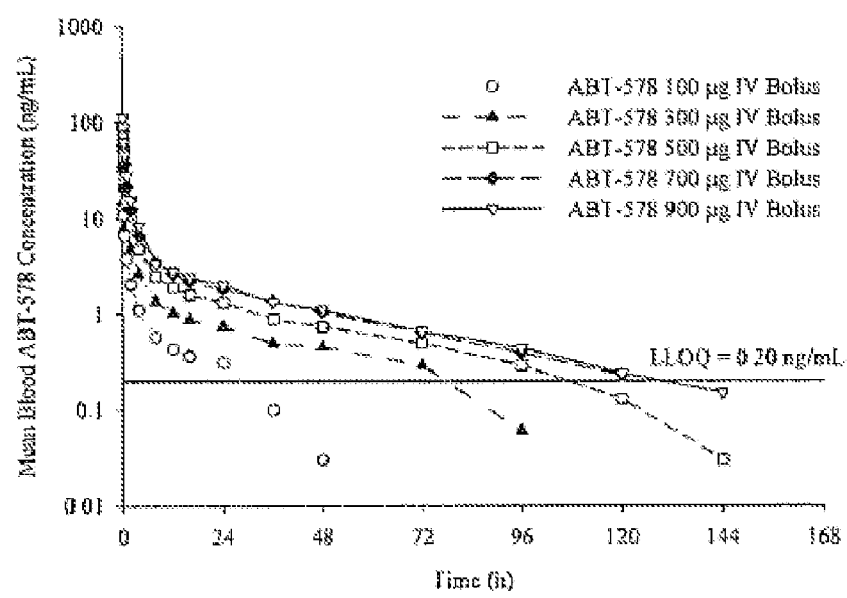
FIG. 5 shows on a log-linear scale mean blood concentration-time plots, following single escalating intravenous doses of zotarolimus in humans.

Mean blood concentration-time plots, following intravenous doses of zotarolimus are presented in FIGS. 4 and 5 on linear scale and log-linear scale, respectively.

Mean±SD pharmacokinetic parameters of zotarolimus after administration of each of the two regimens are shown in Table 11.

TABLE 11

Mean ± SD Pharmacokinetic Parameters of zotarolimus

| Pharmacokinetic Parameters | Dose of zotarolimus | | | | |
|---|---|---|---|---|---|
| | 100 µg (N = 8) | 300 µg (N = 8) | 500 µg (N = 8) | 700 µg (N = 8) | 900 µg (N = 8) |
| $C_5$ (ng/mL) | 13.48 ± 2.87 | 36.71 ± 9.82* | 56.50 ± 27.54* | 88.73 ± 5.00 | 110.78 ± 15.91* |
| $C_5$/Dose (ng/mL/µg) | 0.13 ± 0.03 | 0.12 ± 0.03 | 0.11 ± 0.05 | 0.13 ± 0.01 | 0.12 ± 0.02 |
| $AUC_{0\text{-}last}$ (ng · h/mL) | 24.57 ± 5.89 | 77.79 ± 13.70 | 146.04 ± 32.39 | 207.92 ± 19.44 | 240.80 ± 19.19 |
| $AUC_{0\text{-}last}$/Dose (ng · h/mL/µg) | 0.25 ± 0.06 | 0.26 ± 0.05 | 0.29 ± 0.06 | 0.30 ± 0.03 | 0.27 ± 0.02 |
| $AUC_{0\text{-}inf}$ (ng · h/mL) | 35.28 ± 6.15 | 91.17 ± 14.68 | 162.44 ± 29.58 | 221.77 ± 19.60 | 254.47 ± 17.60 |
| $AUC_{0\text{-}inf}$/Dose (ng · h/mL/µg)# | 0.35 ± 0.06 | 0.30 ± 0.05 | 0.32 ± 0.06 | 0.32 ± 0.03 | 0.28 ± 0.02 |
| $\beta$ (1/h)# | 0.027 ± 0.006 | 0.019 ± 0.002 | 0.017 ± 0.003 | 0.020 ± 0.001 | 0.018 ± 0.002 |
| $t_{1/2}$ (h)$ | 26.0 ± 6.0 | 35.9 ± 4.6 | 40.2 ± 7.8 | 35.0 ± 2.4 | 39.0 ± 3.9 |
| CL (L/h) | 2.90 ± 0.44 | 3.36 ± 0.50 | 3.17 ± 0.58 | 3.18 ± 0.28 | 3.55 ± 0.24 |
| $Vd_\beta$ (L)# | 113 ± 23 | 175 ± 23 | 190 ± 49 | 161 ± 15 | 202 ± 29 |

Figure 6:
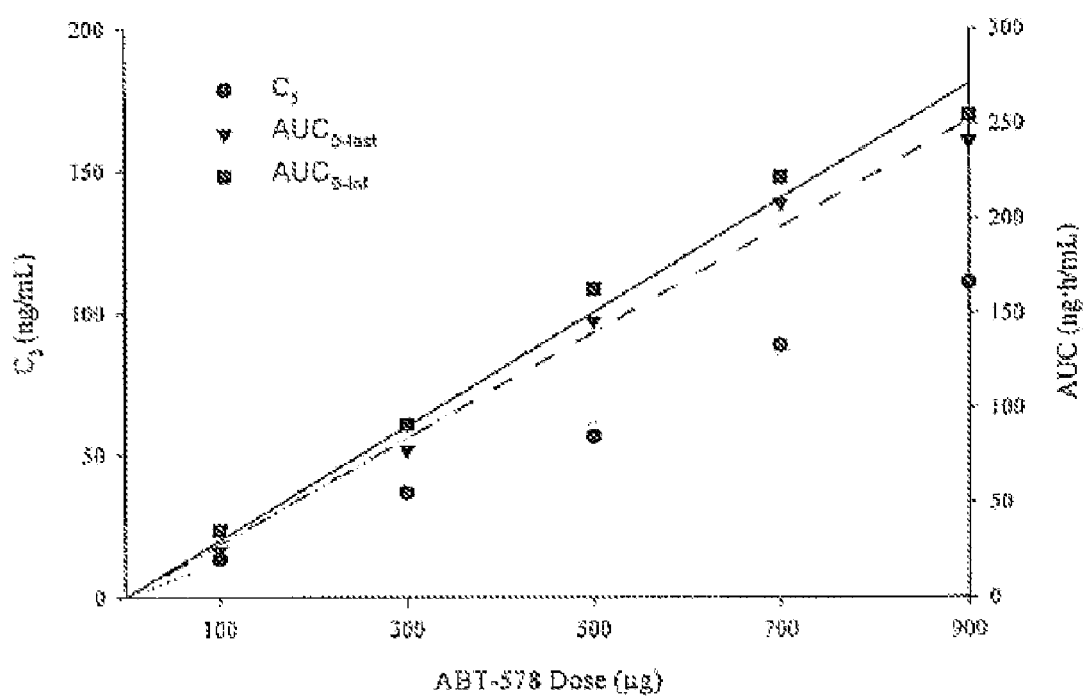
FIG. 6 shows dose proportionality of zotarolimus $C_{max}$ and AUC parameters following single escalating intravenous doses in humans.

$Harmonic mean ± pseudo-standard deviation; evaluations of $t_{1/2}$ were based on statistical tests for $\beta$; A >10% sampling time deviation occurred for the 5-minutes sample for Subjects 201, 304, and 512; $C_5$ concentrations for these subjects were not calculated. (N = 7);
Statistically significant monotonic trend with dose To investigate the questions of dose proportionality and linear pharmacokinetics, an analysis of covariance (ANCOVA) was performed. Subjects were classified by dose level, and body weight was a covariate. The variables analyzed included $\beta$, $Vd_\beta$, dose-normalized $C_5$, and logarithms of dose-normalized $AUC_{0\text{-}last}$ and dose-normalized $AUC_{0\text{-}inf}$. The primary test of the hypothesis of invariance with dose was a test on dose-level effects with good power for a monotonic function of dose. In addition, the highest and lowest dose levels were compared within the framework of the ANCOVA FIG. 6 depicts the dose proportionality of zotarolimus $C_{max}$, $AUC_{0\text{-}last}$, and $AUC_{0\text{-}inf}$. As can be seen in this Figure, no statistically significant monotonic trend was observed with dose normalized $C_{max}$, and $AUC_{0\text{-}last}$ suggesting a dose proportional increase in these parameters. A statistically significant monotonic trend with dose was observed for the dose-normalized $AUC_{0\text{-}inf}$ of zotarolimus (p=0.0152). However, a pairwise comparison of dose-normalized $AUC_{0\text{-}inf}$ across all groups showed that only 100 µg dose-normalized $AUC_{0\text{-}inf}$ was statistically significant different from that of 900 µg and 300 µg (p=0.0032 and p=0.0316, respectively). A statistically significant monotonic trend was also observed with $\beta$. This departure could be due to slight overestimation of $\beta$ with the 100 µg dose group. The mean zotarolimus $C_5$ (concentration at 5 minutes) and $AUC_{0\text{-}inf}$ increased proportionally with dose, as shown in Table 12.

TABLE 12

| Pharmacokinetic Parameters | Dose (µg) (N = 8) | | | | |
|---|---|---|---|---|---|
| | 100 | 300 | 500 | 700 | 900 |
| $C_5$ (ng/mL) | 13.48 ± 2.87 | 36.71 ± 9.82 | 56.50 ± 27.54 | 88.73 ± 5.00 | 110.78 ± 15.91 |
| $AUC_{0\text{-}inf}$ (ng · h/mL) | 35.28 ± 6.15 | 91.17 ± 14.68 | 162.44 ± 9.58 | 221.77 ± 19.60 | 254.47 ± 17.60 |
| CL (L/h) | 2.90 ± 0.44 | 3.36 ± 0.50 | 3.17 ± 0.58 | 3.18 ± 0.28 | 3.55 ± 0.24 |

The mean half-life ranged between 26.0-40.2 h over the studied doses and was not significantly different over the 300-900 µg dose range. Zotarolimus was well tolerated at all doses and no clinically significant physical examination results, vital signs or laboratory measurements were observed.

Safety

The most common treatment-emergent adverse events (reported by two or more subjects in any one treatment group) associated with zotarolimus were injection site reaction and pain.

The majority of the adverse events was mild in severity and resolved spontaneously.

There were no serious adverse events reported in this study.

There were no clinically significant changes in physical examination findings, vital signs, clinical laboratory or ECG parameters during the study.

Conclusion

The pharmacokinetics of IV zotarolimus are dose-proportional over the 100-900 µg dose range with respect to $C_5$ and $AUC_{0\text{-}inf}$. Overall, the pharmacokinetics of zotarolimus were essentially linear across the 100 µg to 900 µg dose range as illustrated by the dose proportional increases in $C_5$, $AUC_{0\text{-}last}$, and $AUC_{0\text{-}inf}$. Single IV bolus doses up to 900 µg were administered without safety concerns.

Mean elimination half-life of zotarolimus ranged from 26.0 to 40.2 hours over the studied dose range. The mean clearance and volume of distribution ranged from 2.90 to 3.55 L/h and 113 to 202 L, respectively. The observed departure from linear kinetics for β and, to a significant extent, for $Vd_\beta$ was due to an overestimation of β for the 100 µg dose group.

Zotarolimus in single doses of 100 to 900 µg were generally well tolerated by the subjects.

EXAMPLE 7

The present study was designed to evaluate the pharmacokinetics of zotarolimus following multiple dosing and to assess its safety while maximizing systemic exposure of healthy subjects. The primary goal was to achieve a total exposure of zotarolimus significantly above the anticipated levels of the drug eluted from coated stents. The study investigated pharmacokinetics and safety of zotarolimus in a Phase 1, multiple dose-escalation study following multiple intravenous infusions of 200, 400 and 800 µg doses, every day for fourteen consecutive days in healthy subjects.

Methods

Phase 1, multiple-escalating dose, double-blind, placebo-controlled, randomized study. Seventy-two subjects equally divided in 3 once-daily (QD) regimens (200, 400 or 800 µg QD with 16 active and 8 placebo per regimen) were administered a 60-minute QD IV infusion of zotarolimus for 14 consecutive days. Blood samples were collected over 24 hours following the first dose, before dosing on days 10, 11, 12, 13, and for 168 hours following Day 14 dose. Urine samples were collected over 24 hours on days 1, 14, 16, 18 and 20. Blood and urine zotarolimus concentrations were determined using a validated LC/MS/MS method. Pharmacokinetic parameters were determined by compartmental analysis. All Day-$AUC_{0\text{-}\infty}$ (area under blood concentration-time curve from time 0 to infinity including all 14 doses) was calculated. Dose and time-linearity and achievement of steady-state were evaluated. Fraction of drug eliminated in urine was determined.

Seventy-two (72) male and female subjects in general good health were enrolled in this study. Demographic information is summarized in Table 13.

TABLE 13

Demographic Summary for All Randomized Group I, Group II and Group III Subjects

| | Mean ± SD (N = 72) | Min-Max |
|---|---|---|
| Age (years) | 36.9 ± 7.8 | 19-59 |
| Weight (kg) | 78.0 ± 8.2 | 61-97 |
| Height (cm) | 178.5 ± 6.3 | 163-193 |
| Sex | 70 Males (97%), 2 Females (3%) | |
| Race | 71 White (99%), 1 Black (1%) | |

Subjects were randomized at two different sites to three groups (Groups I, II and III) as shown in Table 14. Within each group, subjects were equally divided at the two study sites with each enrolling 12 subjects (zotarolimus, eight subjects; placebo four subjects). The dosing scheme within each dose group is presented below:

TABLE 14

Dosing Scheme

| Group | Number of Subjects | Double-Blind IV Treatment |
|---|---|---|
| I | 16[+] | 200 µg zotarolimus over 60 min QD for 14 days |
| | 8 | Placebo over 60 min QD for 14 days |
| II | 16 | 400 µg zotarolimus over 60 min QD for 14 days |
| | 8 | Placebo over 60 min QD for 14 days |
| III | 16 | 800 µg zotarolimus over 60 min QD for 14 days |
| | 8 | Placebo over 60 min QD for 14 days |

[+]Subject 2112 prematurely discontinued the study; subject withdrew consent on Study Day 19.

Subjects received, under fasting conditions, a single 60-minute daily (QD) intravenous infusion of 200, 400, or 800 µg of zotarolimus or a matching intravenous infusion of placebo for Groups I, II and III, respectively on Study Days 1 through 14. The drug was administered Pia a syringe pump connected to a y-site device, which also infused 125-150 mL of 5% aqueous dextrose solution (D5W) over 60 minutes. The groups were dosed sequentially with at least 7 days separating the last dose of the previous group and the first dose of the next group during which time safety data from the previous group was analyzed. Dose escalation was dependent on the safety analysis of the lower dose group.

Five (5)-mL blood samples were collected in potassium EDTA including tubes to evaluate zotarolimus concentrations prior to dosing (0 hour), and at 0.25, 0.5, 1.0, 1 hour 5 min, 1.25, 1.5, 2, 3, 4, 8, 12, 18 and 24 hours after starting infusion on Study Days 1 and 14. Additional samples were collected at 36, 48, 72, 96, 120, 144 and 168 hours after starting infusion on Study Day 14 and before dosing on Days 10, 11, 12 and 13. Urine was collected in containers without preservatives over the following intervals: 0 to 6, 6 to 12, 12 to 18 and 18 to 24 hours after starting the infusion on Study Days 1, 14, 16, 18 and 20.

Blood and urine concentrations of zotarolimus were determined using a validated liquid/liquid extraction HPLC tandem mass spectrometric method (LC-MS/MS).[5] The lower limit of quantification of zotarolimus was 0.20 ng/mL using 0.3 mL blood sample and 0.50 ng/mL using 0.3 mL urine sample.

Safety was evaluated based on adverse event, physical examination, vital signs, ECG, injection site and laboratory tests assessments Results Zotarolimus blood concentration-time data for all subjects were described by a three compartment open model with first order elimination. Over the studied regimens, the range of mean compartmental pharmacokinetic parameters were: CL 4.0-4.6 L/h; $V_1$ 11.3-13.1 L; $V_{SS}$ 92.5-118.0 L, and terminal elimination $t_{1/2}$ 24.7-31.0 h. Zotarolimus pharmacokinetics were consistent with dose linearity over the studied regimens, on days 1 and 14. The pharmacokinetic model simultaneously fit data for days 1 and 14, indicating time-linear pharmacokinetics. All Day-$AUC_{0-\infty}$ for the studied regimens ranged from 677-2395 ng·hr/mL. On average, 0.1% of zotarolimus dose was recovered in the urine within a 24-hour period post-dose.

Pharmacokinetic and Statistical Analysis

The pharmacokinetic parameter values of zotarolimus were estimated for individual subjects using compartmental analysis. Data from the first dose on Study Day 1, the last dose on Study Day 14 and the trough concentrations on Study Days 10, 11, 12 and 13 were simultaneously modeled for each individual subject. Parameters determined were: volume of the central compartment ($V_1$), terminal elimination rate constant (gamma), clearance (CL), volume of distribution at steady state ($V_{SS}$), half-life ($t_{1/2}$), maximum concentration ($C_{max}$), time of maximum concentration ($T_{max}$) area under the blood concentration versus time curve for Day 14 ($AUC_\tau$) and corresponding dose normalized $C_{max}$ and $AUC_\tau$. The optimal model for each individual was used to predict the individual's concentration-time profile over a 14-day period to estimate the chronic exposure over the study duration, i.e., $C_{max}$ and All Day-$AUC_{0-\infty}$ (Area under the predicted blood concentration-time profile from time 0 to infinity taking into account all 14 doses in the study).

To assess dose proportionality for the Study Day 14 dose an analysis of covariance (ANCOVA) for the logarithm of dose-normalized $C_{max}$, dose-normalized AUC, and terminal elimination rate constant was performed. The center and the dose were factors and body weight was a covariate. To address the question of whether steady state was reached, a repeated measures analysis, with center and dose level as factors, was performed on the dose-normalized pre-dose concentrations of Study Days 10-14.

Pharmacokinetics

Figure 7:
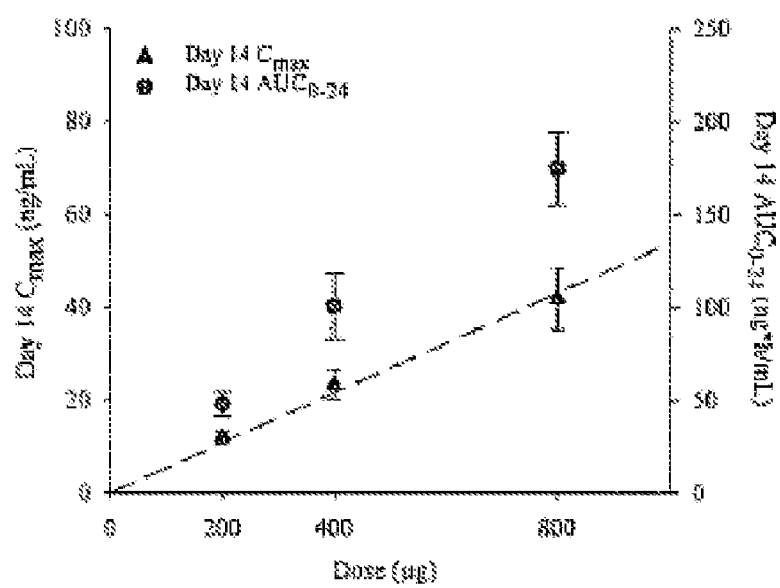
FIG. 7 shows mean blood concentration-time plots of zotarolimus following multiple intravenous doses in humans.

Zotarolimus blood concentration-time data for all subjects were described by a three compartment open model with first order elimination. The mean blood concentrations for zotarolimus for Day 1, Day 14 and Days 1 through 14 are presented in FIG. 7. The mean±SD of pharmacokinetic parameters of zotarolimus are presented in Table 15.

TABLE 15

Mean ± SD Compartmental Pharmacokinetic Parameters of zotarolimus

| Pharmacokinetic Parameters (units) | | Dose Groups | | |
|---|---|---|---|---|
| | | 200 µg QD (N = 15) | 400 µg QD (N = 16) | 800 µg QD (N = 16) |
| $V_1$ | (L) | 11.4 ± 1.7 | 11.3 ± 1.0 | 13.1 ± 3.2 |
| Gamma | (h−1) | 0.028 ± 0.005 | 0.022 ± 0.003 | 0.023 ± 0.003 |
| $C_{max}$* | (ng/mL) | 11.2 ± 1.1 | 21.4 ± 2.4 | 38.7 ± 6.3 |
| $C_{max}$/Dose* | (ng/mL/µg) | 0.056 ± 0.006 | 0.053 ± 0.006 | 0.048 ± 0.008 |
| $AUC_\tau$* | (ng · h/mL) | 49.0 ± 6.2 | 104.2 ± 19.0 | 179.5 ± 17.4 |
| $AUC_\tau$/Dose* | (ng · h/mL/µg) | 0.245 ± 0.031 | 0.260 ± 0.047 | 0.224 ± 0.022 |
| $t_{1/2}$$* | (h) | 24.7 ± 4.6 | 31.0 ± 4.6 | 30.0 ± 4.1 |
| CL* | (L/h) | 4.2 ± 0.6 | 4.0 ± 0.9 | 4.6 ± 0.4 |
| $V_{ss}$* | (L) | 92.5 ± 13.0 | 111.5 ± 21.1 | 118.0 ± 18.7 |

$Harmonic mean ± pseudo-standard deviation
*Secondary predicted parameters

As no bias in the observed versus predicted diagnostic plots over the studied regimens was observed, the ranges of the compartmental pharmacokinetic parameters over the studied dose regimens were very narrow and no meaningful trend over the studied dose regimens in the secondary parameters was observed; dose linearity was inferred for zotarolimus over the studied dose regimens.

Figure 8A:
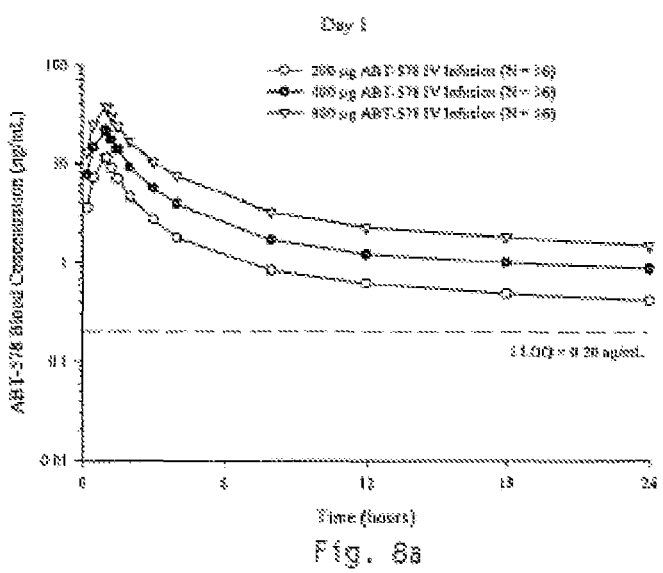
FIGS. 8a-c shows mean zotarolimus blood concentration-time profiles for 200, 400 and 800 µg QD (daily) dose groups on Day 1 (FIG. 8a), Day 14 (FIG. 8b), and Days 1-14 (FIG. 8c).
Figure 8B:
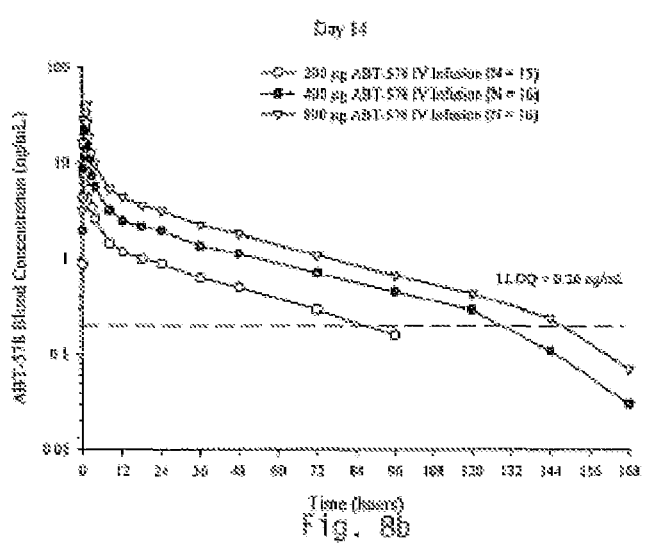
Figure 8C:
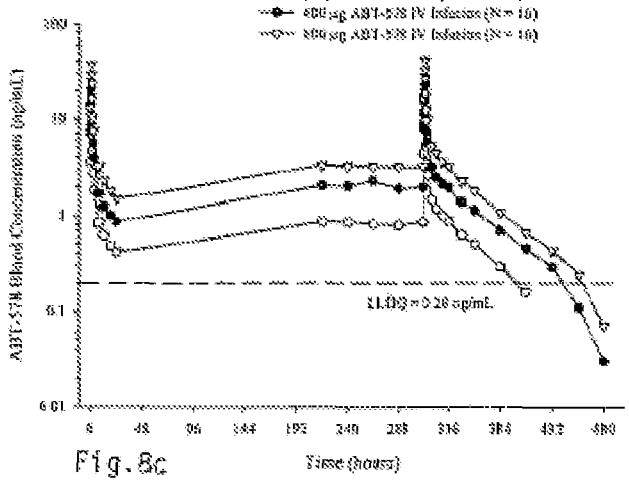

The following figure depicts the dose proportionality in zotarolimus Day 14 $C_{max}$ and $AUC_{0-24h}$ FIGS. 8a, 8b and 8c show mean zotarolimus blood concentration-time profiles for the 200, 400 and 800 µg QD dose groups on Day 1, Day 14 and Days 1-14, respectively. For each dose group, the model adequately described the data on Day 1 as well as Day 14 and in between as exemplified in FIG. 9 (example of mean observed and predicted blood concentration versus time plots upon fitting 800 µg QD dose group data). The excellent fit of the observed zotarolimus concentration-time data over Days 1 through 14 by a 3-compartment model that assumes linear kinetics indicates that zotarolimus exhibits time invariant clearance.

Figure 9:
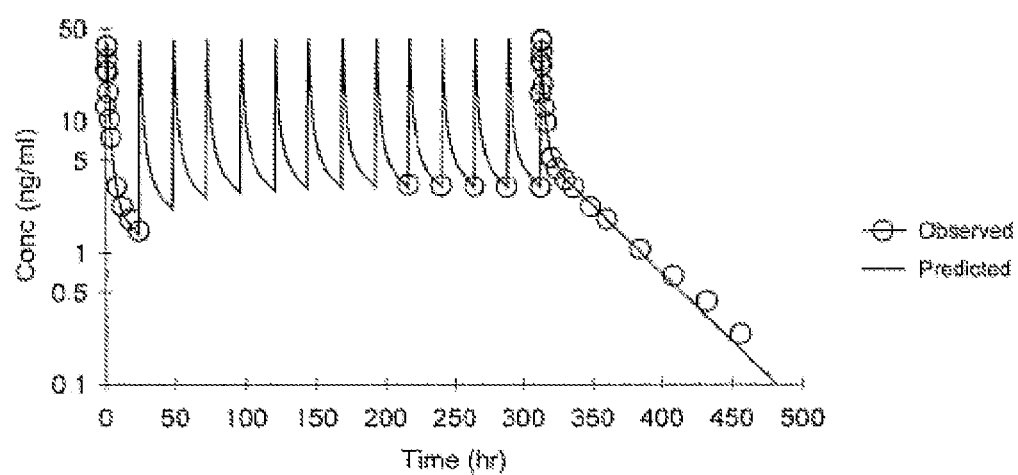
FIG. 9 shows observed zotarolimus concentration-time data over days 1 through 14 for 800 µg QD dose group.

As shown in FIG. 9, no statistical differences were observed in the dose-normalized pre-dose concentrations of Study Days 10-14.

The median $C_{max}$ for the 200, 400 and 800 µg QD dose groups was 11.4, 22.1 and 38.9 ng/mL, respectively. The corresponding median All Day—$AUC_{0-\infty}$ was 677, 1438, and 2395 ng·h/mL, respectively.

The fraction of the zotarolimus dose eliminated in the urine was calculated for the 800 µg QD dose group. On average, approximately 0.1% of zotarolimus was recovered in the urine within a 24-hour period on Day 1 and Day 14.

Safety

The most common treatment-emergent adverse events associated with zotarolimus were pain, headache, injection site reaction, dry skin, abdominal pain, diarrhea and rash. The majority of the adverse events were mild in severity and resolved spontaneously. There were no serious adverse events reported in this study. Specifically, no subject displayed any clinical or biochemical evidence of immunosuppression, QTc prolongation or clinically significant adverse events.

CONCLUSIONS

Zotarolimus pharmacokinetics were dose proportional and time invariant when administered intravenously for 14 consecutive days, over the studied dose regimens.

Steady state for QD dosing of zotarolimus was reached by Day 10, the day on which the first trough samples were measured.

Renal excretion is not a major route of elimination for zotarolimus as approximately 0.1% of the dose was excreted as unchanged drug in the urine per day.

Zotarolimus is generally well tolerated when given in multiple doses of 200, 400, and 800 µg for 14 consecutive days.

EXAMPLE 8

Anti-proliferative Activity of Zotarolimus and Paclitaxel

Experiments were performed to investigate interactions between zotarolimus (ABT-578) and paclitaxel when administered in combination. The effects of paclitaxel and zotarolimus on the anti-proliferative activity of human coronary artery smooth muscle (hCaSMC) and endothelial cells (hCaEC) were determined using an in vitro proliferation assay. The proliferation and migration of vascular smooth muscle cells into the vascular neointima is a characteristic pathologic response seen in restenotic lesions (Lafont and Libby, 1998). As a result, in vitro assays which specifically measure the anti-proliferative activity of candidate anti-restenotic compounds on human coronary artery smooth muscle and endothelial cells predict potential anti-restenotic activity in vivo.

Figure 10A:
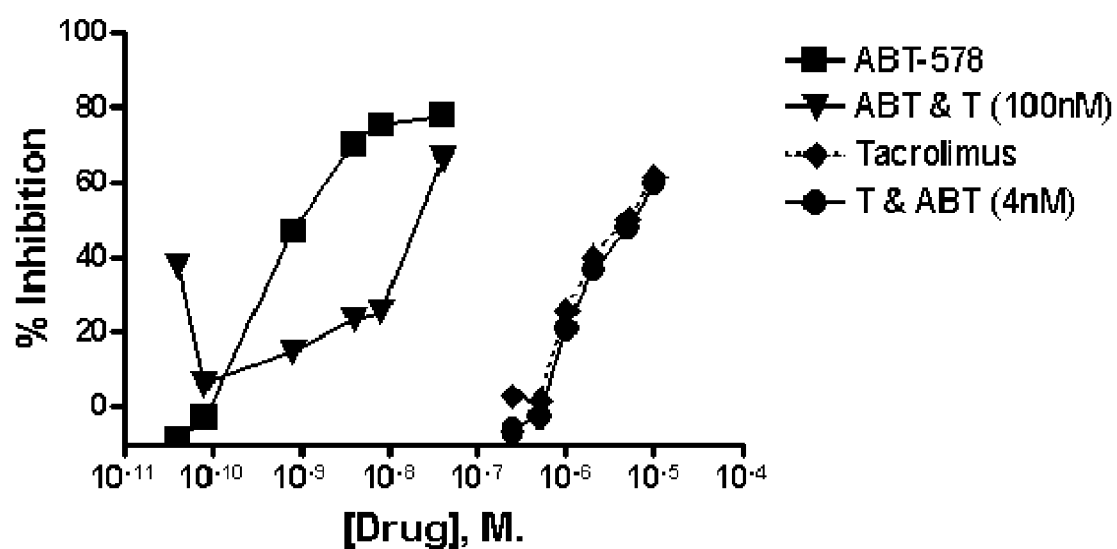

Compounds or combinations of compounds which attenuate growth factor-mediated human coronary artery smooth muscle cell (hCaSMC) proliferation, as measured by the tritium incorporation assay in vitro, are candidate anti-restenotic agents. The tritium incorporation assay is an accurate and sensitive method to determine cell number and proliferation. This assay was employed to determine if agents which demonstrate anti-proliferative activity alone also demonstrate similar activity in combination. Furthermore, agents which demonstrate lower potency anti-proliferative activity may block the activity of more potent anti-proliferative agents when administered in combination. The attenuation of zotarolimus's anti-proliferative activity by tacrolimus is a clear example of this effect (FIG. 10A). To determine the potential anti-restenotic activity of combinations of zotarolimus and paclitaxel, the proliferation of hCaSMC was measured in the presence of each compound and in combination.

Paclitaxel interferes with microtubule de-polymerization, blocking cell progression at the S phase (Schiff and Horwitz, 1980). Zotarolimus, like rapamycin, blocks cyclin-dependent kinase via mTOR inhibition and inhibits cell cycle progression at the G1-S phase (Marx et al., 1995; Sehgal, 1998; Sehgal, 2003).

To determine if paclitaxel attenuated or augmented the activity of zotarolimus the effect of paclitaxel and zotarolimus alone and in combination on growth-factor induced proliferation was determined. Data were analyzed for additivity using an isobologram approach and a combination index analysis. An isobologram is a Cartesian plot of pairs of doses that, in combination, yield a specified level of effect. It is a convenient way of graphically displaying results of drug-combination and similar studies, because paired values of experimental points that fall below or above the line connecting the axial points indicate synergistic and non-synergistic interactions, respectively.

Proliferation Assay Methods $^3$H-thymidine Uptake

Cell proliferation was monitored by following incorporation of $^3$H-thymidine into newly synthesized DNA of cells stimulated by serum and growth factors. Exponentially growing hCaSMCs were seeded into 96-well flat bottom tissue culture plates at 5,000 cells/well (10,000 cells/well for hCaECs). The cells were allowed to attach overnight. The growth medium was removed the following day, and cells were washed twice with un-supplemented (basal) medium to remove traces of serum and growth factors. Basal medium (200 µl) was added to each well and the cells incubated in medium lacking growth factors and serum to starve and synchronize them in the G0 state. After starvation (48 hours for hCaSMCs and 39 hours for hCaECs) in medium lacking serum and growth factors, the cells were replenished with 200 µl supplemented medium in the absence or presence of drugs. Dimethylsulfoxide (DMSO) was maintained at a final concentration of 0.1% in all wells. After a 72-hour incubation period, 25 µl (1 µCi/well) of $^3$H-thymidine (Amersham Biosciences; Piscataway, N.J.) were added to each well. The cells were incubated at 37° C. for 16-18 hours, and the cells harvested onto 96-well plates including bonded glass fiber filters using a cell harvester (Harvester 9600, TOMTEC; Hamden, Conn.). The filter plates were air dried overnight and MicroScint-20 (25 µl; PerkinElmer; Wellesley; Mass.) was added to each filter well and the plates were counted using a TopCount microplate scintillation counter (PerkinElmer). Controls included medium only, starved cells and cells in complete medium. Drug activity was established by determining the inhibition of $^3$H-thymidine incorporation into newly synthesized DNA relative to cells grown in complete medium.

The data are presented as percent inhibition of $^3$H-thymidine incorporation relative to vehicle-treated controls and are given as the mean±SEM of 3-4 experiments. A semi-log plot of the average values of inhibition from each experiment versus drug concentration was generated, and the IC$_{50}$ (Median Inhibition Concentration (concentration that reduces cell proliferation by 50%) for each experiment was determined by extrapolation of the 50% inhibition level relative to cells incubated in complete medium in the absence of drugs. The final IC$_{50}$'s are means of the 3-4 experiments.

In these experiments, the x-axis represents the concentration of the drug being varied. Each graph includes a zotarolimus- and paclitaxel-alone curve. The set of curves in each graph was generated by adding paclitaxel at a fixed concentration to the indicated concentrations of zotarolimus. Each curve represents the dose-response of zotarolimus (concentration given on the x-axis) in the presence of the indicated fixed concentration of paclitaxel.

Two methods were used to analyze the combined effects of zotarolimus and paclitaxel on proliferation. Isobolograms were generated at several effect levels (Tallarida et al., 1989). The concentration response curves were fit by non-linear regression (Prism, GraphPad Software; San Diego, Calif.) to obtain EC50 and hill slope values. The concentration eliciting a specific anti-proliferative effect was determined using a four-parameter equation (equation 1):

$$Y = \text{Bottom} + (\text{Top} - \text{Bottom})/(1 + 10^{\wedge}((\text{LogEC50} - X) * \text{HillSlope}))$$

X is the logarithm of concentration. Y is the response
Alternately:

$$Y = \text{Bottom} + \frac{(\text{Top} - \text{Bottom})}{1 + \frac{EC_{50}^{Hillslope}}{[X]^{Hillslope}}} \quad [1]$$

Where X=log concentration of drug yielding Y response and top and bottom values are constrained to 100 and 0, respectively. In addition to isobolograms, the data were analyzed for synergism using the method of Chou and Talalay (Chou and Talalay, 1984) with the following exception. The regression model generated for each curve was used in place of median-effect data (log-logit plot) because the non-linear four-parameter equation more accurately models the concentration-response curve. The median-effect plot is heavily influenced by values of fractional occupancy below 0.2 and greater than 0.8. The combination indices (CI) for several drug combinations yielding 25%, 50%, 60% and 75% were calculated according to equation 2.

$$(D)1/(Dx)1 + (D)2/(Dx)2 + ((D)1(D)2)/(Dx)1(Dx)2 = CI \quad [2]$$

Where at a specified effect level (D)1 and (D)2 are the concentrations of drug 1 and drug 2 in the combination and (Dx)1 and (Dx)2 are the concentrations of drug 1 alone and drug 2 alone. CI values reflect the summation of effects of the combinations assuming each drug was acting in accordance with its own potency. Equation 2 describes predicted effects for the combination of two mutually nonexclusive compounds. If each drug contributes to the combined effect in accordance to its own dose-dependent fractional occupancy then the CI is equal to 1. Values of CI below one are considered synergistic and values significantly over one are considered sub-additive. Since the relationship between CI, and synergism, additivity or attenuation can be effect-level dependent, CI was determined at several effect levels using multiple drug combinations. CI values were plotted as a function of the effect level (or fa) at which they were calculated. CI values, similar to the isobologram analysis are effect level dependent and vary as the level of effect changes therefore it is important to consider effect level in comparing CI values. The accuracy of CI values are, in turn dependent on the accuracy of the concentration values used in their calculation. In this study an accurate method (iterative curve fitting by GraphPad software) was used to calculate drug concentrations from each cumulative dose-response curve at several effect levels. Dose-response curves can be fit to data which may demonstrate little dose-dependent activity. This is particularly apparent when analyzing dose-response curves generated in the presence of a high concentration of one of the test agents. Errors in determination of drug concentrations from the dose-response curves under these conditions may result in high CI values at low effect levels (fa). Therefore, CI values generated from well defined dose-response curves near or above half-maximal effects (i.e., fa~0.5) are the most accurate predictors of the activity of drug combinations. Under these conditions values of CI below one are considered supra-additive and values significantly over one are considered sub-additive. Values near one are considered additive.

Results

This study addressed the activity of agents on two cell types implicated in restenosis, human coronary artery smooth muscle (hCaSMC) and endothelial cells (hCaEC). The results are given in FIG. 10 and Table 16. FIG. 10 shows that tacrolimus blocks the anti-proliferative activity of zotarolimus in smooth muscle cells in vitro (FIG. 10A). The anti-proliferative activity of zotarolimus, paclitaxel (P) and combinations in smooth muscle cells (FIG. 10B) and endothelial cells (FIG. 10C) in vitro are also shown. FIGS. 10D-G show isobologram analyses of combination anti-proliferative activity in smooth muscle cells. The concentrations producing the specified level of anti-proliferative activity were determined from the dose-response curves generated by non-linear curve fitting of the data means. FIGS. 10G-K show isobologram analyses of the anti-proliferative activity of the combination of zotarolimus and paclitaxel in endothelial cells. The concentrations of compounds producing the specified levels of activity were determined from the mean data. FIGS. 10L-M shows a combination index (CI) analysis of the anti-proliferative activity of combinations of ABT-578 and paclitaxel in hCaSMC and hCaEC. CI levels were determined from the mean data using the method of Chou and Talalay (Chou and Talalay, 1984).

The data from each individual agent alone show that both zotarolimus and paclitaxel dose-dependently inhibit proliferation in each cell type. FIG. 10B shows that the inhibition of proliferation by zotarolimus is not blocked by paclitaxel. Increasing concentrations of both paclitaxel and zotarolimus almost completely inhibit hCaEC and hCaSMC proliferation. These data show that at low effect levels (i.e., ≦50% inhibition of proliferation) the effects of combining paclitaxel and zotarolimus are predicted by the sum of their individual activity. This relationship holds at most levels of inhibition except at high levels of inhibition. At high levels of inhibition, the anti-proliferative activity slightly exceeds that predicted by the activity of each agent alone. Both the isobologram and CI analyses of the hCaSMC data show that the combination including paclitaxel (2.5 nM) and zotarolimus demonstrate potential supra-additive anti-proliferative activity at high effect levels (60 and 75%).

TABLE 16

Inhibition of hCaSMC and hCaEC Cell Proliferation by zotarolimus, paclitaxel and Combinations

| Drug | hCaSMC IC$_{50}$ (nM) Mean ± SEM | Drug | hCaEC IC$_{50}$ (nM) Mean ± SEM |
|---|---|---|---|
| ABT-578 | 4.2 ± 1.7 | ABT-578 | 3.6 ± 0.2 |
| PAC | 3.0 ± 0.5 | PAC | 4.6 ± 0.3 |
| ABT-578 + 0.1 nM PAC | 5.0 ± 0.7 | ABT-578 + 1 nM PAC | 3.6 ± 0.3 |

TABLE 16-continued

Inhibition of hCaSMC and hCaEC Cell Proliferation by zotarolimus, paclitaxel and Combinations

| Drug | hCaSMC IC$_{50}$ (nM) Mean ± SEM | Drug | hCaEC IC$_{50}$ (nM) Mean ± SEM |
|---|---|---|---|
| ABT-578 + 1 nM PAC | 4.0 ± 1.4 | ABT-578 + 2.5 nM PAC | 2.1 (n = 2) |
| ABT-578 + 5 nM PAC | N.D.* | ABT-578 + 5 nM PAC | N.D.* |
| ABT-578 + 10 nM PAC | N.D.* | ABT-578 + 10 nM PAC | N.D.* |

N.D.* Concentrations of paclitaxel alone at or above 5 nM inhibit proliferation by greater than 50% preventing calculation of ABT-578 IC$_{50}$'s in these experiments.

These data show that paclitaxel does not block the antiproliferative activity of zotarolimus. Furthermore, high concentrations of zotarolimus and paclitaxel show anti-proliferative activity that appears synergistic.

EXAMPLE 9

Elution Experiments of Beneficial Agents

Coating the Stents with PC1036

Prior to any experimentation, coated stents were prepared. These were 3.0 mm×15 mm 316 L electropolished stainless steel stents. Each stent was spray-coated using a filtered 20 mg/mL solution of phosphorylcholine polymer PC1036 (Biocompatibles Ltd.; Farnham, Surrey, UK) in ethanol (EtOH). The stents were initially air-dried and then cured at 70° C. for 16 hours. They were then sent for gamma irradiation at $\leq$25KGy.

Loading the Stent with Therapeutic Substances

In these experiments, agents were loaded onto stents and elution profiles examined. In general, the procedure was as follows. Multiple PC-coated stents were loaded with each drug combination solution. The solutions of the drugs were usually in the range of 2-20 mg/mL of zotarolimus and 1.0-7.0 mg/mL paclitaxel in 100% ethanol, with ~10% PC1036 added to the solution to enhance film formation. The loading of dual drug and single drug stents was accomplished by spray loading appropriate drugs onto a stent in a single pass spray system within an isolator unit. All DES stents were made from Abbott Laboratories TriMaxx N5 design 15 mm×3.0 mm stents, and all catheters were Medtronic (Minneapolis, Minn.) OTW, 15 mm×3.0. The numbers manufactured for each combination included units for accelerated elution, drug load content, impurity profile, and animal efficacy testing. The stents were weighed before loading with the drug solution. All stents were spray loaded to their targeted drug contents from solutions including the appropriate drug(s) and PC1036 in ethanol in a 91:9 ratio. For paclitaxel:zotarolimus combinations, stents were prepared a; 7 μg/mm of paclitaxel with 10 μg/mm of zotarolimus, 3.5 μg/mm of paclitaxel with 5 μg/mm of zotarolimus, 1 μg/mm of paclitaxel with 10 μg/mm of zotarolimus, 7 μg/mm of paclitaxel alone, and 10 μg/mm of zotarolimus alone. Once loaded, all stents were dried in open vials for 30 minutes in an oven set at 40° C. and weighed to determine drug loads. The drug-loaded stents were then over-coated with 5 μg/mm of PC1036 by spraying with a 10 mg/ml polymer solution in ethanol.

After over-coating, the stents were cured in an oven at 70° C. for two hours before weighing to determine overcoat weight. After drug loading, the stents were assembled onto catheters, crimped onto the balloon. The stents were then visually inspected for coating and physical defects. The stent/catheters were inserted into a packaging hoop and the stent/catheter was placed in a Tyvek pouch. The pouch was sealed with a Vertrod (San Rafael, Calif.) Impulse Heat sealer. A stent identification label was placed in the bottom corner on the front side of the pouch, outside of the sealed area including the product. The product was then placed in white boxes labeled with the product details and shipped for EtO sterilization. On return from sterilization, the product was packaged in foil pouches including sachets of oxygen scavenger and desiccant. The pouches were labeled with the stent identification number and product details. The pouches were sealed while flushing with nitrogen.

Extracting Drugs from the Stent

For each drug, three stents were used to evaluate the total amount of drug loaded. The stents were immersed in 6 mL of 50% acetonitrile, 50% water solution and sonicated for 20 minutes. The concentration of the each drug in the extraction solution was analyzed by high-pressure liquid chromatography (HPLC).

At the end of the elution experiments discussed below, the stents were removed from the elution media and immersed in 6 mL of 50% acetonitrile, 50% water solution and sonicated for 20 minutes. The concentration of each drug in these vials indicated the amount of the drug remaining on the stents at the end of the elution experiments.

Elution Process

For assessment of in vitro drug elution, stents (n=3 for each group) were expanded and then placed in a solution of 10 mM acetate buffer (pH=4.0) with 1% Solutol HS 15 (BASF; Florham Park, N.Y.) heated to 37° C. in a USP Type II dissolution apparatus. A solubilizing agent was needed because the drugs have very low water solubility. The dissolution medium was buffered to minimize the degradation of 'olimus drugs that occurs at pH's above 6. Buffering at pH 4 solves this problem. Since these drugs have minimum dissociation at these pH ranges, pH should have little impact on elution rate. Samples were pulled from the dissolution bath at selected time intervals using a syringe sampler fitted with only Teflon, stainless steel or glass surfaces. Aliquots were collected after 15 min, 30 min, 1 hr, 2 hr, 4 hr, 6 hr, 8 hr, 12 hr and 24 hr. The samples are assayed for zotarolimus and paclitaxel concentration via HPLC. Data are expressed as drug-eluted in micrograms and mean-percent eluted.

In the HPLC method, it is necessary to use column-switching to minimize Solutol contamination of the analytical column and to allow rinsing of the guard column; otherwise, the system becomes coated with the Solutol and the chromatographic retention changes dramatically. The sample was first injected onto a guard column. Once the analyte peak eluted from the guard column and passed onto the analytical column, the guard column was switched out of the analytical path. The guard column was then washed to remove the Solutol prior to the next injection.

Results

Figure 11:
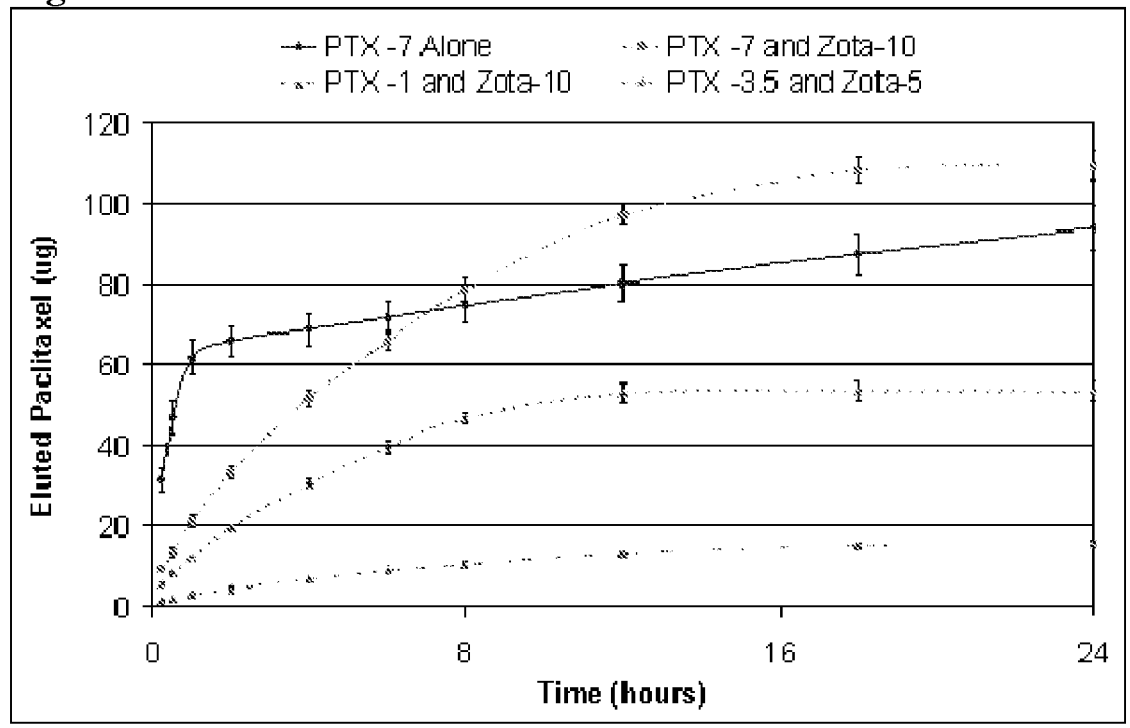
FIG. 11 shows paclitaxel release from stents loaded with paclitaxel (7 μg/mm) alone, paclitaxel (7 μg/mm) and zotarolimus (10 μg/mm); paclitaxel (3.5 μg/mm) and zotarolimus (5 μg/mm); or paclitaxel (1 μg/mm) and zotarolimus (10 μg/mm).
Figure 12:
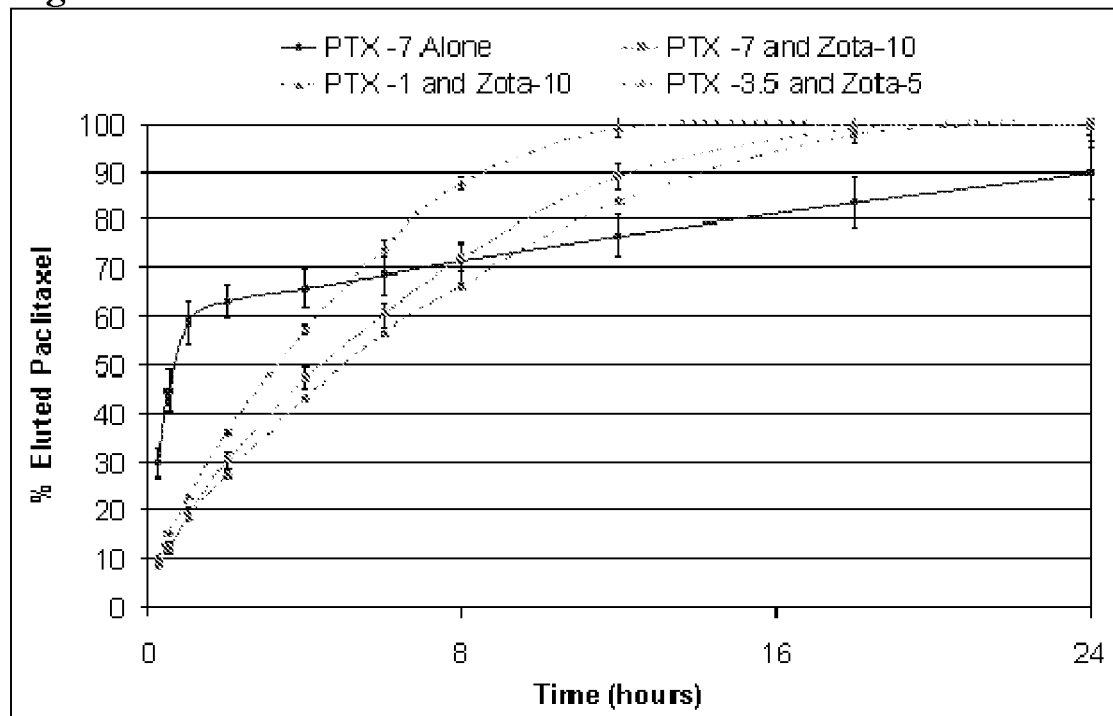
FIG. 12 shows percent paclitaxel release from stents loaded with paclitaxel (7 μg/mm) alone, paclitaxel (7 μg/mm) and zotarolimus (10 μg/mm); paclitaxel (3.5 μg/mm) and zotarolimus (5 μg/mm); or paclitaxel (1 μg/mm) and zotarolimus (10 1μg/mm).
Figure 13:
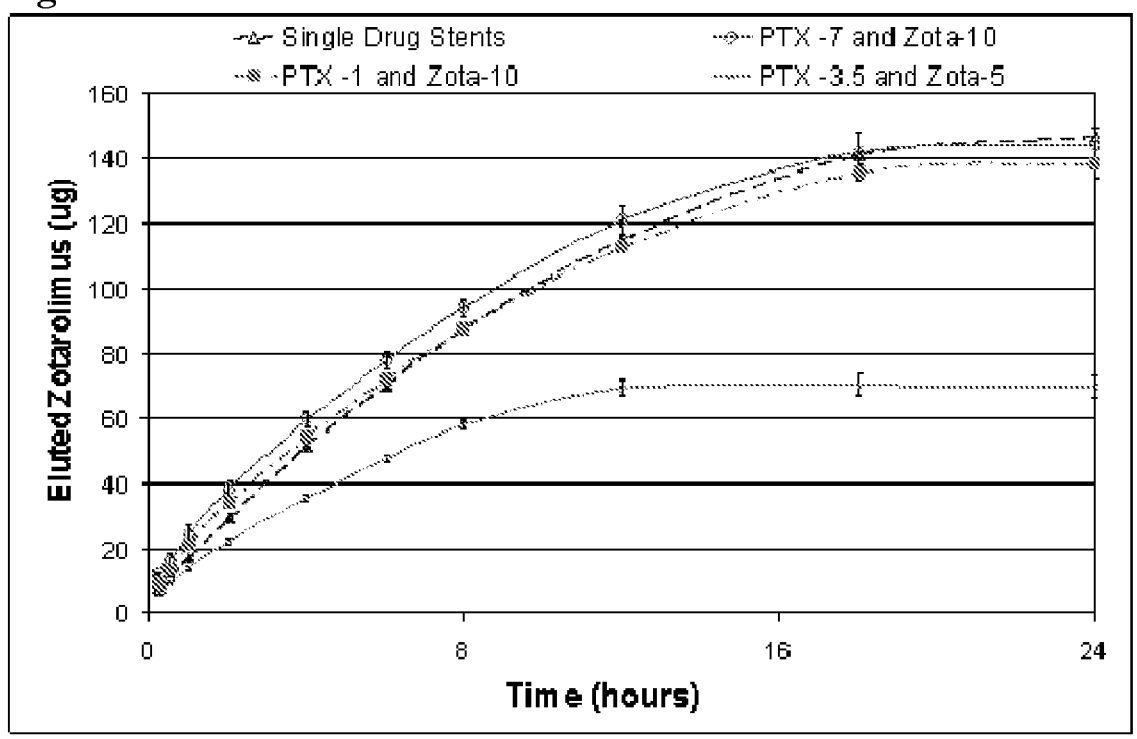
FIG. 13 shows zotarolimus release from stents loaded with zotarolimus (10 μg/mm) alone, paclitaxel (7 μg/mm) and zotarolimus (10 μg/mm); paclitaxel (3.5 μg/mm) and zotarolimus (5 μg/mm); or paclitaxel (1 μg/mm) and zotarolimus (10 μg/mm).

FIGS. 11-13 illustrate the accelerated elution rate of stents loaded with zotarolimus and paclitaxel at: 7 µg/mm of paclitaxel with 10 µg/mm of zotarolimus, 3.5 µg/mm of paclitaxel with 5 µg/mm of zotarolimus, 1 µg/mm of paclitaxel with 10 µg/mm of zotarolimus, 7 µg/mm of paclitaxel alone, and 10 µg/mm of zotarolimus alone onto stents with a 5 µg/mm topcoat of the polymer PC1036 as detailed above.

In FIG. 11, the 24-hour elution profile shown is where one beneficial agent is paclitaxel and the second beneficial agent is zotarolimus. Elution was carried out as described above. The paclitaxel single drug stent showed a combination of two release profiles, an initially large burst release (~60%) followed by a slower, zero-order release rate, whereas dual drug stents that include both paclitaxel and zotarolimus do not have a burst release.

FIG. 12 presents the same data as FIG. 11, but has been normalized by the total drug determined on the stent after final stent extract. As can be seen, 100% of both drugs are recovered from the stent coatings, and the total drug recovered is in excellent agreement with the drug load predicted by stent weight uptake during the drug loading process. These data, along with drug potency and related substances testing on stents from the same batch, indicate that the drugs were stable in the polymer coating when manufactured as described. The small standard deviations show that the dual drug elution stents can be manufactured with reproducible elution kinetics.

In FIG. 13, the four curves are the elution profiles (in micrograms release versus time) for zotarolimus, alone and in the presence of paclitaxel, respectively, under the same conditions. As can be seen, the three curves that belong to stents with 10 µg/mm of zotarolimus alone or in combination with paclitaxel are very similar. This suggests that paclitaxel has little effect on the elution profile of zotarolimus. The fourth curve (PTX 3.5 and Zota 5) was expected to elute half of the drug as the other stents—as it does.

EXAMPLE 10

Neointimal Formation In Vivo After Stent Implantation

A porcine coronary overstretch model study (Schwartz, 1992) was conducted to examine neointimal formation for 28 days following stent implantation. The study evaluated a number of drug-eluting stents randomized is. control zotarolimus-loaded (10 µg/mm; ZoMaxx™) stents. Unexpectedly, the combination of zotarolimus and paclitaxel delivered from a stent is highly efficacious, offering improved reductions in neointimal hyperplasia in the widely utilized porcine coronary overstretch model.

Experimental Design and Methods

In each pig, two major coronary arteries were implanted with one test stent each, and the third major coronary artery was implanted with one zotarolimus (10 µg/mm or 1.69 µg/mm$^2$) coated ZoMaxx™ stent. Additionally, three pigs were implanted with three non-drug including TriMaxx™ stents (Abbott Laboratories; Abbott Park, Ill.) each (9 total stents) for comparison. The stents that were compared included ZoMaxx™ stents (3.0×15 mm), commercially available sirolimus (8.5 µg/mm or 1.40 µg/mm$^2$)-polymer coated Cypher® stents (3.0×13 mm; Cordis Corp.; Miami, Fla.) and paclitaxel-(6.8 µg/mm or 1.0 µg/mm$^2$) polymer coated Taxus® stents (3.0×16 mm; Boston Scientific; Natick, Mass.) stents. The remaining groups of stents were 3.0×15 mm. A paclitaxel stent with the same drug loading as Taxus (7 µg/mm), but loaded with PC-1036 as the delivery vehicle, was included in the study (PTX-7). In addition, three sets of combination stents were coated that varied in the amounts of zotarolimus and paclitaxel loaded as shown in Table 17.

TABLE 17

Combination drug-eluting stents used in Example 10

| Stent | zotarolimus (µg/mm) | paclitaxel (µg/mm) |
|---|---|---|
| 1 | 10 | 7 |
| 2 | 5 | 3.5 |
| 3 | 10 | 1 |

Finally, non-drug eluting TriMaxx stents were included to identify a baseline for neointimal formation.

Stents were implanted with a balloon/artery ratio of 1.30 as determined by quantitative coronary angiography. There were no cardiac- or stent-related mortalities in the study. After 28 days, animals were euthanized, and the hearts were removed and perfusion fixed at ~100 mm Hg with lactated Ringer's solution until cleared of blood, followed by 10% neutral buffered formalin. Stented vessels were excised, then infiltrated and embedded in methylmethacrylate (MMA). All blocks including stented vessels were sectioned so that three, in-stent sections and two control sections were taken. Two serial thin sections (approximately 5 µm) were taken at each level and stained with hematoxylin and eosin (HE) and Masson's Verhoeff Elastin (MVE). Sections were evaluated and scored using the BIOQUANT TCW98 image analysis system (Bioquant; Nashville, Tenn.).

Results

Figure 14:
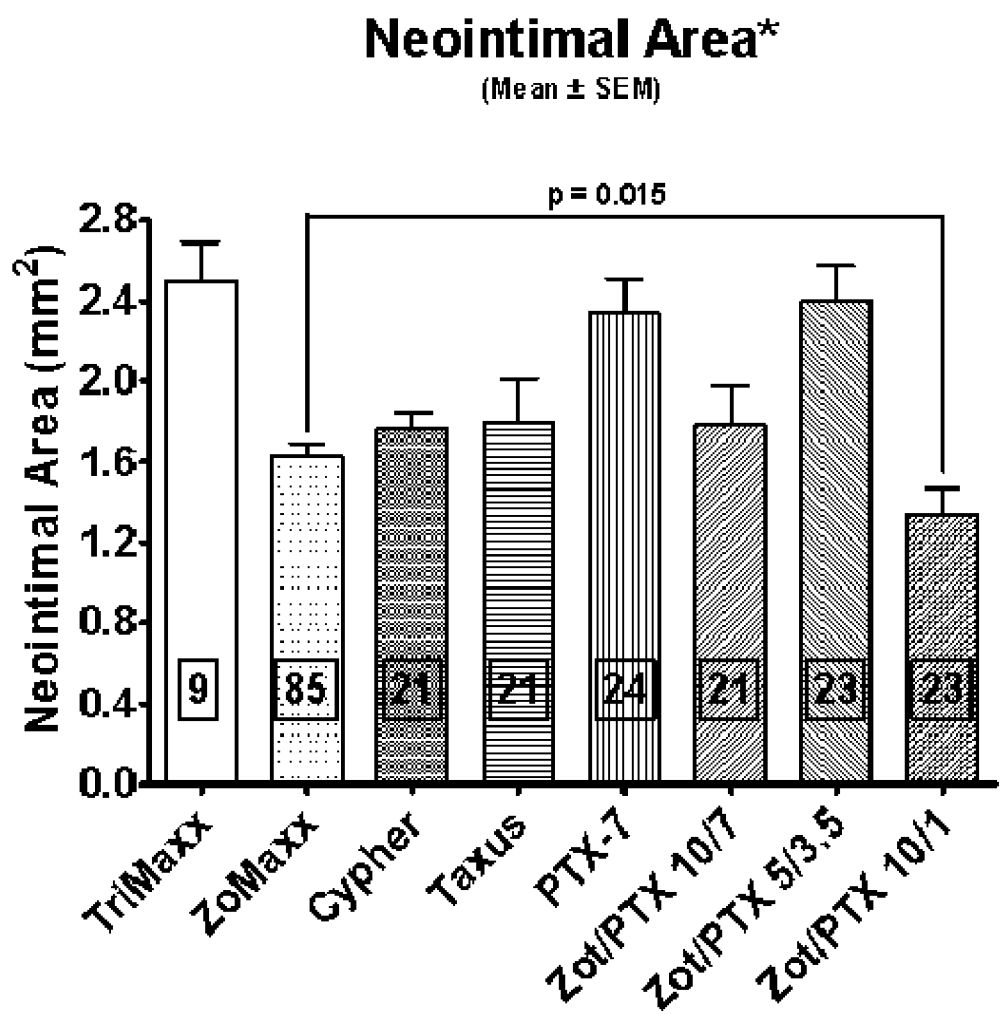
FIG. 14 shows the neointimal areas (30% overstretch) after 28 days of implantation in swine blood vessels of drug-eluting (single and multiple) and non-drug-eluting stents; boxed numbers indicate the number of stents per group.
Figure 15:
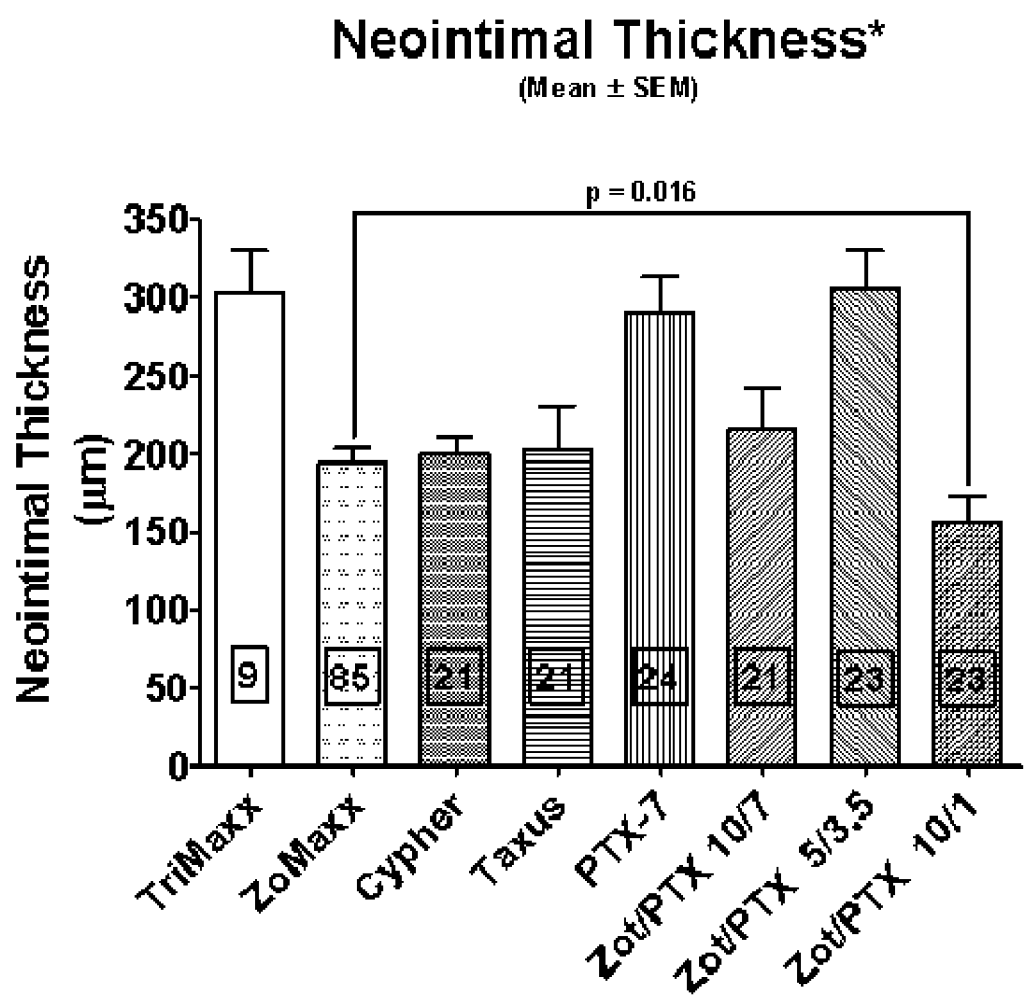
FIG. 15 shows neointimal thicknesses (30% overstretch) after 28 days of implantation in swine blood vessels of drug-eluting (single and multiple) and non-drug-eluting stents; boxed numbers indicate the number of stents per group.
Figure 16:
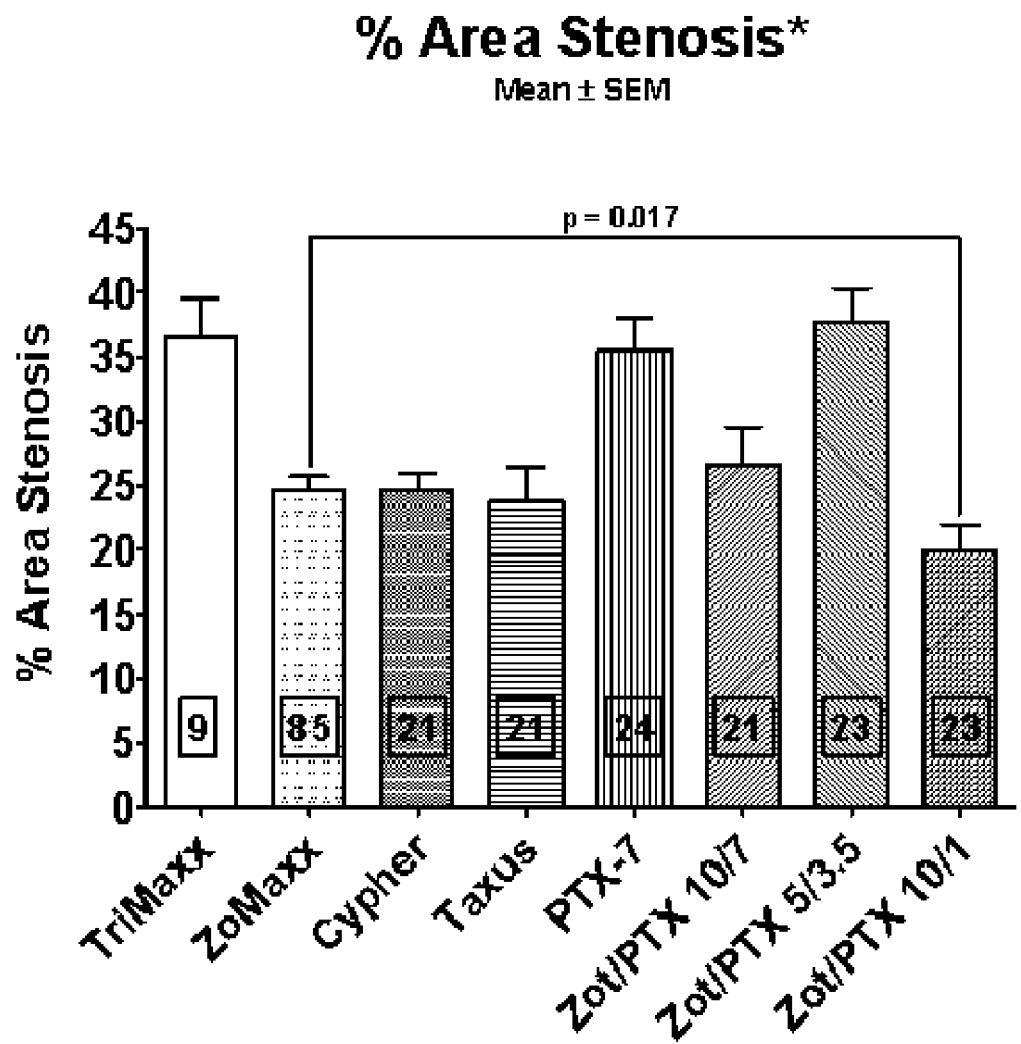
FIG. 16 shows percent area stenosis (30% overstretch) after 28 days of implantation in swine blood vessels of drug-eluting (single and multiple) and non-drug-eluting stents; boxed numbers indicate the number of stents per group.
Figure 17:
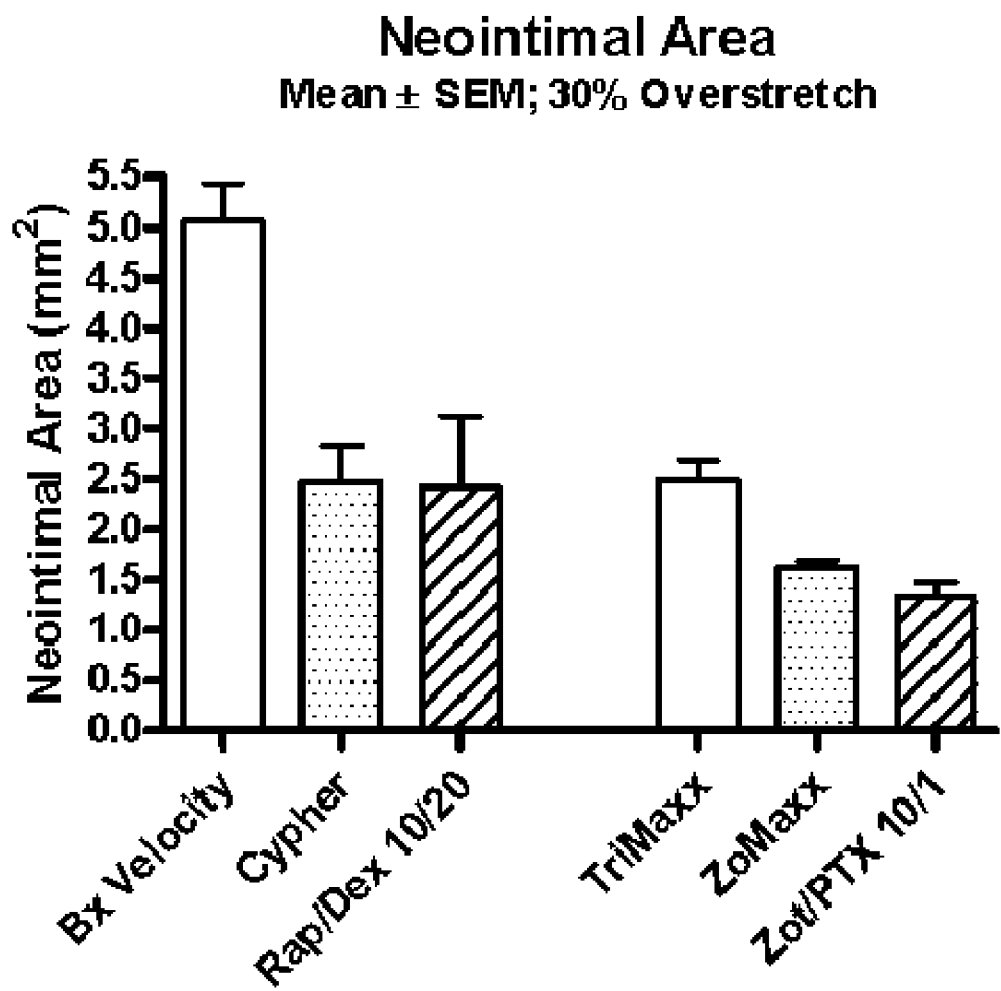
FIG. 17 shows a comparison of neointimal area measurements (30% overstretch) for combination stents from a 28-day swine study.
Figure 18:
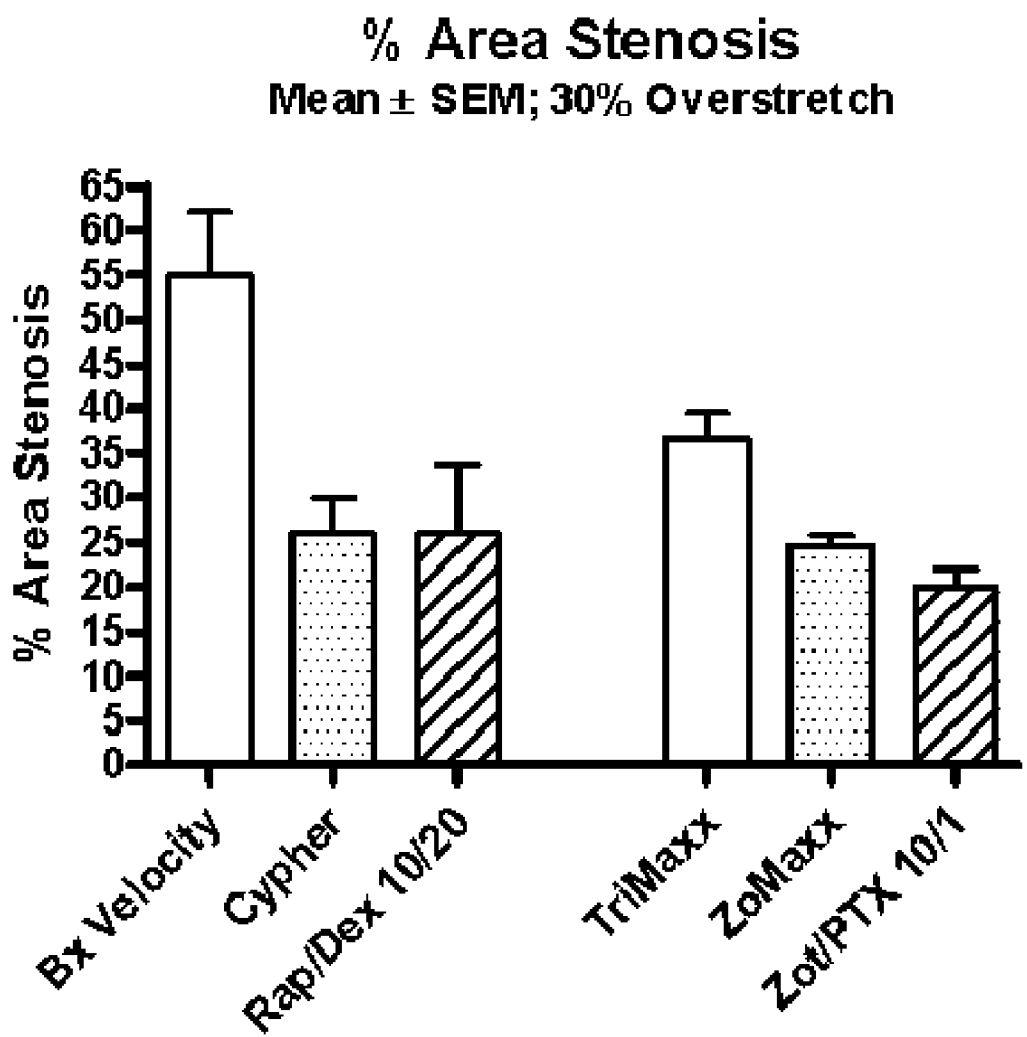
FIG. 18 shows a comparison of percent area stenosis measurements (30% overstretch) for combination stents from a 28-day swine study.
Figure 19:
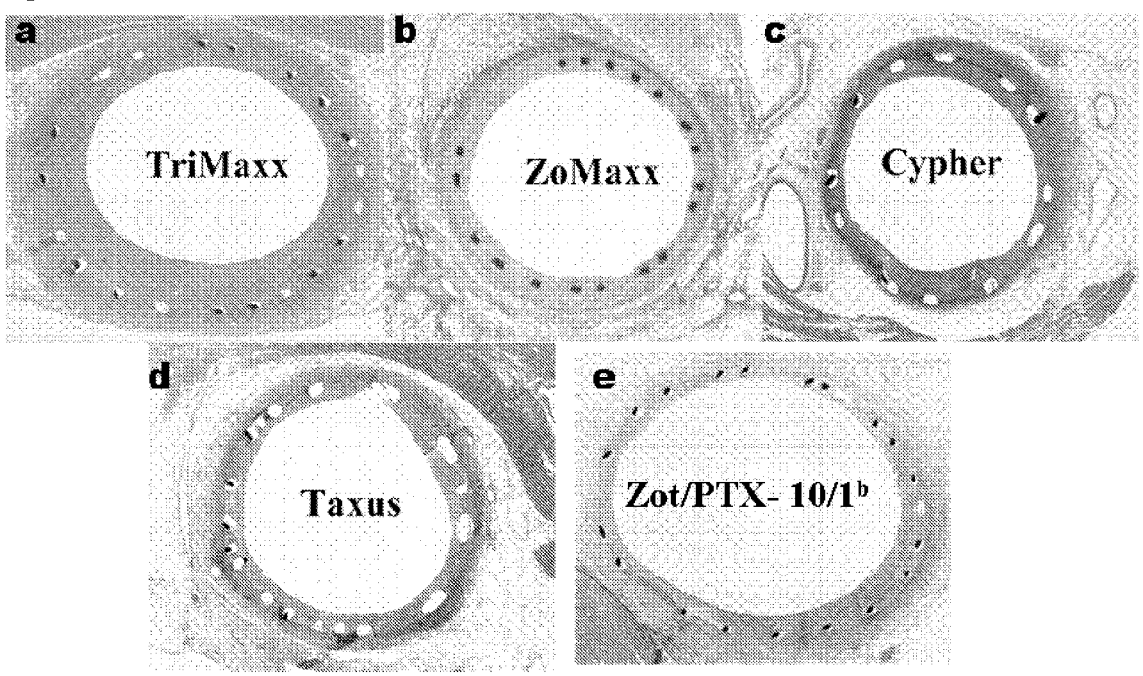
FIGS. 19*a-e* show micrographs of cross-sections of representative blood vessels from a swine study, representing average neointimal areas for each group.

Average values for all stents within the eight groups for neointimal area, neointimal thickness, and percent-area stenosis are shown in FIGS. 14-16, respectively (represented as means±s.e.m.; p values were calculated versus TriMaxx; boxed numbers indicate the number of stents/group). ZoMaxx™, Cypher®, and Taxus® stents had statistically equivalent reductions in formation of neointima as represented by morphometric measurements compared to TriMaxx™ stents. The combination stent including 10 µg/mm of zotarolimus and 1 µg/mm paclitaxel (Zot/PTX 10/1) showed a significant reduction in neointimal hyperplasia versus TriMaxx™ stents. In addition, the Zot/PTX 10/1 combination stents also showed a further improvement in reduction in neointima versus ZoMaxx™, Cypher®, and Taxus® stents. Table 18 summarizes the improvements obtained with ZoMaxx™ and the Zot/PTX 10/1 combination drug stents versus TriMaxx™; the comparisons are graphically presented in FIGS. 17 (Neointimal Area) and 18 (Percent Area Stenosis).

Each of the state-of-the-art, single drug stents, ZoMaxx™, Cypher™, and Taxus® showed dramatic reductions in neointimal formation versus TriMaxx™ controls. For example the average reduction in neointima for ZoMaxx™ stents was 34.5% versus controls. The Zot/PTX 10/1 combination stents yielded further improvement in the reduction of neointimal observed with the best single drug stents available commercially and in clinical trials. The Zot/PTX 10/1 combination drug-eluting stents had an average reduction in neointimal hyperplasia of 46.8% when compared to TriMaxx™ non-drug eluting stents. Compared with ZoMaxx™, Cypher®, and Taxus® the additional dramatic reduction in formation of neointima was 18.8, 21.7, and 21.5%, respectively (Table 19). Pictorial representations are shown in FIGS. 19a-19e, which show micrographs that represent average neointimal areas for each group.

TABLE 18

Improvements in morphometric measurements vs. TriMaxx ™ non-drug eluting stents

| Stent | Neointimal Area (mm²) | Neointimal Thickness (µm) | % Area Stenosis | Average |
|---|---|---|---|---|
| ZoMaxx ™ | 34.7% | 36.0% | 32.7% | 34.5% |
| Zot/PTX 10/1 | 46.3% | 48.5% | 45.5% | 46.8% |

TABLE 19

Improvements in neointimal hyperplasia for zotarolimus (10 µg/mm) and paclitaxel (1 µg/mm) combination drug-eluting stents compared with ZoMaxx ™, Cypher ®, and Taxus ®

| Comparator | Neointimal Area | Neointimal Thickness | % Area Stenosis | Average |
|---|---|---|---|---|
| ZoMaxx ™ | 17.8% | 19.6% | 19.1% | 18.8% |
| Cypher ® | 24.1% | 21.9% | 19.2% | 21.7% |
| Taxus ® | 25.2% | 23.2% | 16.1% | 21.5% |

The stents coated with 10 µg/mm of zotarolimus and 7 µg/mm paclitaxel (Zot/PTX 10/7) had statistically equivalent reductions in formation of neointima to ZoMaxx stents (FIGS. 14-16). Embodiments of ideal ratio of 'olimus drug to paclitaxel derivative include between 10:7 and 10:0.01 by weight, 10:0.1, and with a ratio equal to 10:1. Reduction in the total drug dose to 5 µg/mm of zotarolimus and 3.5 µg/mm paclitaxel (Zot/PTX 5/3.5) resulted in suboptimal performance equivalent to non-drug eluting TriMaxx stents (FIGS. 14-16). Consequently, the optimum total dose of 'olimus and paclitaxel derivative should not fall below about 150 µg on a 15 mm stent as the ratio of 'olimus to paclitaxel approaches 10:7.

Based on previously published data from the (Falotico, 2003; Suzuki et al., 2001), one would conclude that combining 'olimus drugs with a second drug would offer no advantage. The observations from these experiments are surprising and unexpected, showing that appropriate combinations of zotarolimus and paclitaxel is highly efficacious, offering increased reduction in neointimal hyperplasia in the art-accepted porcine coronary overstretch model. FIGS. 15 and 16 demonstrate the remarkable difference between the observed results with zotarolimus and paclitaxel (Zot/PTX 10/1) and previously published results with sirolimus and dexamethasone (Falotico, 2003; Suzuki et al., 2001). The previously published experiments showed no benefit between the combination stent and the single drug-eluting stent. Even with the dramatic improvement in control TriMaxx™ versus BX Velocity®, in the porcine model with the same overstretch ratio, the combination product in this example was both substantially better than controls and substantially and statistically significantly better than the single drug eluting stent, ZoMaxx™.

EXAMPLE 11

(Prophetic) Clinical Application

The introduction and subsequent widespread use of stents that deliver single anti-proliferative agents has reduced the restenosis rate to less than 10% in the general clinical population. However, a clear rationale exists for the delivery of appropriate drug combinations from stents to treat patients both in the general clinical population and from a variety of cardiovascular disease subsets to reduce restenosis rates and adverse clinical events still further. For example, it is well accepted that the rate of restenosis is significantly increased in stented diabetic patients when compared to those without the disease, and that an inflammatory response to stenting exists in both diabetic and non-diabetic patients (Aggarwal et al., 2003). In addition, inflammation is a hallmark in patients with acute coronary syndrome (ACS), a term which defines a range of acute myocardial ischemic conditions, including unstable angina, non-ST segment elevation myocardial infarction, as well as infarction associated with persistent ST-segment elevation. These patients are often prime candidates for stent deployment, and relative to the general patient population undergoing percutaneous intervention (PCI), have significantly higher rates of recurrent ischemia, reinfarction and subsequent need for repeat PCI procedures. Finally, obesity is often associated with a pro-inflammatory state and endothelial dysfunction. Both conditions are known to be independent predictors of early restenosis after coronary stent placement. In fact, a case has been made for an association between obesity, interleukin-6 (IL-6) production by adipocytes and coronary artery disease, suggesting a link between elevations of this inflammatory cytokine and the development of CAD in this sub-set of patients (Yudkin et al., 2000).

Diabetic patients exhibit higher levels of the inflammatory marker, c-reactive protein (CRP) than non-diabetic patients (Aggarwal et al., 2003; Dandona and Aljada, 2002). This protein has been clearly identified as a key inflammatory mediator in patients with coronary artery disease and is a predictor of adverse events in patients with severe unstable angina (Biondi-Zoccai et al., 2003). CRP stimulates the production of monocyte chemo-attractant protein (MCP-1) by human endothelial cells. The release of this mediator is accompanied by the influx of monocytes, resulting in a marked inflammatory state as these cells are activated and move into the sub-endothelial space, where they form foam cells including oxidized low-density lipoprotein (LDL). Plasma IL-6 and tumor necrosis factor-α (TNF-α) are inflammatory cytokines that are also elevated in the obese patient, and in type 2 diabetics. In fact, elevation of high-sensitivity CRP, IL-6 or serum vascular cell adhesion molecule-1 (VCAM-1) have been associated with increased mortality in patients with coronary artery diseases (Roffi and Topol, 2004). Since it has been shown that neointimal formation, a hallmark of the restenotic process, is accentuated by inflammation, the use of stents which deliver a combination of agents with anti-inflammatory and anti-proliferative activities including zotarolimus and paclitaxel to the local vessel environment would be expected to have clear utility in diabetic patients.

Disruption of an atheromatous plaque is central to the initiation of an acute coronary syndrome (Grech and Ramsdale, 2003). Plaque rupture may be induced by increased concentrations of matrix metalloproteinases secreted by foam cells, leading to plaque instability and ultimate rupture of the thin fibrous cap which overlies the developing lesion. In addition, tissue factor, which is expressed on the surface of foam cells, activates coagulation factor VII, which leads to the formation of thrombin. Generation of this protein leads to platelet activation and aggregation, as well as the conversion of fibrinogen to fibrin, and the clear formation of thrombus. Initial concern regarding the deployment of stents in this setting appears unfounded, since improvements in stent deployment and technique have shown that stented patients have less recurrent ischemia, similar reinfarction rates, and reduced need for repeat angioplasty (Grech and Ramsdale, 2003). The close relationship between inflammation and the development of coronary artery lesions makes the use of stents that deliver a combination of agents with anti-inflammatory and anti-proliferative activities including zotarolimus and paclitaxel to the local vessel environment an attractive approach to treating such patients.

The stents described herein will be deployed in patients who are diagnosed with ischemic heart disease due to stenotic lesions in coronary arteries and in subsets of the clinical population at higher risk for recurrent coronary disease and other adverse clinical events. Other targets for intervention include peripheral vascular diseases including stenosis in the superficial femoral arteries, renal arteries, iliacs, and vessels below the knee. Target vessels for interventional procedures will be reached using percutaneous vascular access via either the femoral or radial artery, and a guiding catheter wilt be inserted into the vessel. The target lesion wilt then be crossed with a guide wire, and the balloon catheter will be inserted either over the wire or using a rapid exchange system. The physician will determine the appropriate size of the stent to be implanted by online quantitative coronary angiography (QCA) or by visual estimate. The stent will be deployed using appropriate pressure as indicated by the compliance of the stent, and a post-procedure angiogram can then be obtained. When the procedure is completed, the patient will be regularly monitored for angina status and for the existence of any adverse events. The need for repeat procedures will also be assessed.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

REFERENCES

Aggarwal, A., D. J. Schneider, B. E. Sobel, and H. L. Dauerman. 2003. Comparison of inflammatory markers in patients with diabetes mellitus versus those without before and after coronary arterial stenting. *Am J Cardiol.* 92:924-9.

Baker, H., A. Sidorowicz, S. N. Sehgal, and C. Vezina. 1978. Rapamycin (AY-22,989), a new antifungal antibiotic. III. In vitro and in vivo evaluation. *J Antibiot (Tokyo).* 31:539-45.

Bierer, B. E., S. L. Schreiber, and S. J. Burakoff. 1991. The effect of the immunosuppressant FK-506 on alternate pathways of T cell activation. *Eur j Immunol.* 21:439-45.

Biondi-Zoccai, G. G., A. Abbate, G. Liuzzo, and L. M. Biasucci. 2003. Atherothrombosis, inflammation, and diabetes. *J Am Coll Cardiol.* 41:1071-7.

Brown, E. J., M. W. Albers, T. B. Shin, K. Ichikawa, C. T. keith, W. S. Lane, and S. L. Schreiber. 1994. A mammalian protein targeted by G1-arresting rapamycin-receptor complex. *Nature.* 369:756-8.

Bunchman, T. E., and C. A. Brookshire. 1991. Smooth muscle cell proliferation by conditioned media from cyclosporine-treated endothelial cells: a role of endothelin. *Transplant Proc.* 23:967-8.

Caufield. U.S. Pat. No. 5,023,262. 1991. Hydrogenated Rapamycin Derivatives.

Caufield. WO 92/05179. 1992. Carboxylic Acid Esters of Rapamycin.

Chou, T. C., and P. Talalay. 1984. Quantitative analysis of dose-effect relationships: the combined effects of multiple drugs or enzyme inhibitors. *Adv Enzyme Regul.* 22:27-55.

Dandona, P., and A. Aljada. 2002. A rational approach to pathogenesis and treatment of type 2 diabetes mellitus, insulin resistance, inflammation, and atherosclerosis. *Am J Cardiol.* 90:27G-33G.

Dumont, F. J., M. R. Melino, M. J. Staruch, S. L. Koprak, P. A. Fischer, and N. H. Sigal. 1990. The immunosuppressive macrolides FK-506 and rapamycin act as reciprocal antagonists in murine T cells. *J Immunol.* 144:1418-24.

Eng. U.S. Pat. No. 4,401,653. 1983. Combination of Rapamycin and Picibanil for the Treatment of Tumors.

Failli. EPO 467606. 1992a. Rapamycin Derivatives.

Failli. U.S. Pat. No. 5,120,842. 1992b. Silyl Ethers of Rapamycin.

Failli. U.S. Pat. No. 5,177,203. 1993. Rapamycin 42-Sulfonates and 42-(N-Carboalkoxy) Sulfamates Useful as Imunosuppressie Agents.

Falotico, R. Publication No. US 2003/0216699. 2003. Coated medical devices for the prevention and treatment of vascular disease.

Fretz, H., M. Albers, A. Gala, R. Standaert, W. Lane, S. Burakoff, B. Bierer, and S. Schreiber. 1991. Rapamycin and FK506 binding proteins (immunophilins). *J. Am. Chem. Soc.* 113:1409-1411.

Grech, E. D., and D. R. Ramsdale. 2003. Acute coronary syndrome: unstable angina and non-ST segment elevation myocardial infarction. *Bmj.* 326:1259-61.

Harding, M. W., A. Galat, D. E. Uehling, and S. L. Schreiber. 1989. A receptor for the immunosuppressant FK506 is a cis-trans peptidyl-prolyl isomerase. *Nature.* 341:758-60.

Hayward, C., D. Yohannes, and S. Danishefsky. 1993. Total synthesis of rapamycin via a novel titanium-mediated aldol macrocyclization reaction. *J. Am. Chem. Soc.* 115: 9345-9346.

Higuchi, T., and V. Stella. 1987. Pro-drugs as Novel Delivery systems.

Igaki, K. U.S. Pat. No. 6,413,272. 2002. Stent for vessel.

Ji, Q., M. Reimer, and T. El-Shourbagy. 2004. 96-Well liquid-liquid extraction liquid chromatography-tandem mass spectrometry method for the quantitative determination of ABT-578 in human blood samples. *Journal of Chromatography B.* 805:67-75.

Kao. U.S. Pat. No. 5,120,725. 1992a. Bicyclic Rapamycins.

Kao. U.S. Pat. No. 5,120,727. 1992b. Rapamycin Dimers.

Kino, T., N. Inamura, F. Sakai, K. Nakahara, T. Goto, M. Okuhara, M. Kohsaka, H. Aoki, and T. Ochiai. 1987. Effect of FK-506 on human mixed lymphocyte reaction in vitro. *Tranplant Proc.* 19:36-9.

Lafont, A., and P. Libby. 1998. The smooth muscle cell: sinner or saint in restenosis and the acute coronary syndromes? *J Am Coll Cardiol.* 32:283-5.

Luly. 1995. Macrocyclic Immunomodulators.

Martel, R. R., J. Klicius, and S. Galet. 1977. Inhibition of the immune response by rapamycin, a new antifungal antibiotic. *Can J Physiol Pharmacol.* 55:48-51.

Marx, S. O., T. Jayaraman, L. O. Go, and A. R. Marks. 1995. Rapamycin-FKBP inhibits cell cycle regulators of proliferation in vascular smooth muscle cells. *Circ Res.* 76:412-7.

Miller, M. L., and I. Ojima. 2001. Chemistry and chemical biology of taxane anticancer agents. *Chem Rec.* 1:195-211.

Morris, R. 1992. Rapamycins: antifungal, antitumor, antiproliferative, and immunosuppressive macrolides. *Transplant. Rev.* 6:39-87.

Morris, R., and B. Meiser. 1989. Identification of a new pharmacologic action for an old compound. *Med. Sci. Res.* 17:609.

Nicolaou, K., T. Chakraborty, A. Piscopio, N. Minowa, and P. Bertinato. 1993. Total synthesis of rapamycin. *J. Am. Chem. Soc.* 115:4419-4420.

Okuhara, M., T. Hirokazu, G. Toshio, K. Tohru, and H. Hiroshi. EP Patent No. 0184162. 1986. Tricyclo compounds, a process for their production and a pharmaceutical composition containing the same.

Or, Y., J. Luly, and R. Wagner. U.S. Pat. No. 5,527,907. 1996. Macrolide immunomodulators.

Paiva, N. L., A. L. Demain, and M. F. Roberts. 1991. Incorporation of acetate, propionate, and methionine into rapamycin by Streptomyces hygroscopicus. *J Nat Prod.* 54:167-77.

Prescott, D. M.e. 1976 In Methods in cell biology. Vol. XIV. Academic Press., San Diego [etc.]. 33 et seq.

Rakhit. U.S. Pat. No. 4,316,885. 1982. Acyl Derivatives of Rapamycin.

Roche, E. 1987. Bioreversible Carriers in Drug Design. American Pharmaceutical Association and Pergamon Press.

Roffi, M., and E. J. Topol. 2004. Percutaneous coronary intervention in diabetic patients with non-ST-segment elevation acute coronary syndromes. *Eur Heart J.* 25:190-8.

Romo, D., S. Meyer, D. Johsnon, and S. Schrieber. 1993. Total synthesis of (–)-rapamycin using an Evans-Tishchenko fragment coupling. *J. Am. Chem. Soc.* 115:7906-7907.

Sabatini, D. M., H. Erdjument-Bromage, M. Lui, P. Tempst, and S. H. Snyder. 1994. RAFT1: a mammalian protein that binds to FKBP12 in a rapamycin-dependent fashion and is homologous to yeast TORs. *Cell.* 78:35-43.

Schiff, P. B., and S. B. Horwitz. 1980. Taxol stabilizes microtubules in mouse fibroblast cells. *Proc Natl Acad Sci U S A.* 77:1561-5.

Schwartz, R. 1992. Restenosis and the proportional neointimal response to coronary artery injury: results in a porcine model. *J Am Coll Cardiol.* 19:267-274.

Sehgal, S. N. U.S. Pat. No. 3,929,992. 1975. Rapamycin and Process of Preparation.

Sehgal, S. N. U.S. Pat. No. 3,993,749. 1976. Rapamycin and Process of Preparation.

Sehgal, S. N. 1998. Rapamune (RAPA, rapamycin, sirolimus): mechanism of action immunosuppressive effect results from blockade of signal transduction and inhibition of cell cycle progression. *Clin Biochem.* 31:335-40.

Sehgal, S. N. 2003. Sirolimus: its discovery, biological properties, and mechanism of action. *Transplant Proc.* 35:7S-14S.

Sehgal, S. N., H. Baker, C. P. Eng, K. Singh, and C. Vezina. 1983. Demethoxyrapamycin (AY-24,668), a new antifungal antibiotic. *J Antibiot (Tokyo).* 36:351-4.

Sehgal, S. N., H. Baker, and C. Vezina. 1975. Rapamycin (AY-22,989), a new antifungal antibiotic. II. Fermentation, isolation and characterization. *J Antibiot (Tokyo).* 28:727-32.

Shichiri, M., Y. Hirata, T. Nakajima, K. Ando, T. Imai, M. Yanagisawa, T. Masaki, and F. Marumo. 1991. Endothelin-1 is an autocrine/paracrine growth factor for human cancer cell lines. *J Clin Invest.* 87:1867-71.

Siekierka, J. J., S. H. Hung, M. Poe, C. S. Lin, and N. H. Sigal. 1989. A cytosolic binding protein for the immunosuppressant FK506 has peptidyl-prolyl isomerase activity but is distinct from cyclophilin. *Nature.* 341:755-7.

Stack, R., H. Clark, W. Wlaker, and J. McElhaney. U.S. Pat. No. 5,527,337. 1996. Bioabsorbable stent and method of making the same.

Stella. U.S. Pat. No. 4,650,803. 1987. Prodrugs of Rapamycin.

Surendra. U.S. Pat. No. 4,885,171. 1989. Use of Rapamycin in Treatment of Certain Tumors.

Suzuki, T., G. Kopia, S. Hayashi, L. R. Bailey, G. Llanos, R. Wilensky, B. D. Klugherz, G. Papandreou, P. Narayan, M. B. Leon, A. C. Yeung, F. Tio, P. S. Tsao, R. Falotico, and A. J. Carter. 2001. Stent-based delivery of sirolimus reduces neointimal formation in a porcine coronary model. *Circulation.* 104:1188-93.

Tallarida, R. J., F. Porreca, and A. Cowan. 1989. Statistical analysis of drug-drug and site-site interactions with isobolograms. *Life Sci.* 45:947-61.

Vezina, C., A. Kudelski, and S. N. Sehgal. 1975. Rapamycin (AY-22,989), a new antifungal antibiotic. I. Taxonomy of the producing *streptomycete* and isolation of the active principle. *J Antibiot (Tokyo).* 28:721-6.

Yamagishi, S., C. C. Hsu, K. Kobayashi, and H. Yamamoto. 1993. Endothelin 1 mediates endothelial cell-dependent proliferation of vascular pericytes. *Biochem Biophys Res Common.* 191:840-6.

Yudkin, J. S., M. Kumari, S. E. Humphries, and V. Mohamed-Ali. 2000. Inflammation, obesity, stress and coronary heart disease: is interleukin-6 the link? *Atherosclerosis.* 148:209-14.

What is claimed is:

1. A pharmaceutical composition, comprising paclitaxel or salts, prodrugs, or derivatives thereof; and zotarolimus or salts prodrugs thereof,
   wherein the ratio of zotarolimus:paclitaxel, r, is by weight $10:7 \leq r \leq 10:0.01$;
   wherein if the composition is administered to a subject in a blood vessel on a medical device, the formation of neointimal hyperplasia is reduced; and
   wherein the composition is formulated for local delivery to a subject.

2. The composition of claim 1, wherein r=10:1.

3. The composition of claim 1, wherein the formulation is associated with a medical device.

4. The composition of claim 3, wherein the medical device comprises a stent.

5. The composition of claim 4, wherein the stent comprises at least one coating on a surface, and wherein the coating is associated with the composition.

6. The composition of claim 5, wherein the concentration of zotarolimus is about 10 µg/mm of stent, and the concentration of paclitaxel is about 1 µg/mm of stent.

7. The composition of claim 1, wherein the subject is human.

8. The composition of claim 1, wherein the mode of administration of the therapeutically effective amount of the combination of drugs is one selected from the group consisting of orally, rectally, parenterally, intracisternally, intravaginally, intraperitoneally, topically, bucally, intravenously, intra-arterially, intramuscularly, subcutaneously, intra-articularly, transdermally, and interpericardially.

9. A composition comprising zotarolimus or salts prodrugs thereof; and paclitaxel or salts, prodrugs, or derivatives thereof;
   wherein the ratio of zotarolimus:paclitaxel, r, is by weight $10:7 \leq r \leq 10:0.01$, and
   wherein an effect of the zotarolimus complements activity of paclitaxel, and paclitaxel complements activity of zotarolimus when locally administered.

10. The composition of claim 9, wherein r=10:1.

11. The composition of claim 9, wherein the formulation is associated with a medical device.

12. The composition of claim 11, wherein the medical device comprises a stent.

13. The composition of claim 12, wherein the stent comprises at least one coating on a surface, and wherein the coating is associated with the composition.

14. The composition of claim 13, wherein the concentration of zotarolimus is about 10 μg/mm of stent, and the concentration of paclitaxel is about 1 μg/mm of stent.

15. The composition of claim 9, wherein the subject is human.

16. The composition of claim 9, wherein the mode of administration of the therapeutically effective amount of the combination of drugs is selected from the group consisting of orally, rectally, parenterally, intracisternally, intravaginally, intraperitoneally, topically, bucally, intravenously, intra-arterially, intramuscularly, subcutaneously, intra-articularly, transdermally, and interpericardially.

17. A kit, comprising the composition of claim 1.

18. A kit, comprising the composition of claim 9.

* * * * *

UNITED STATES PATENT AND TRADEMARK OFFICE
CERTIFICATE OF CORRECTION

PATENT NO. : 7,357,942 B2  Page 1 of 3
APPLICATION NO. : 11/464676
DATED : April 15, 2008
INVENTOR(S) : Sandra E. Burke et al.

It is certified that error appears in the above-identified patent and that said Letters Patent is hereby corrected as shown below:

At column 8, lines 50 – 65, delete:

"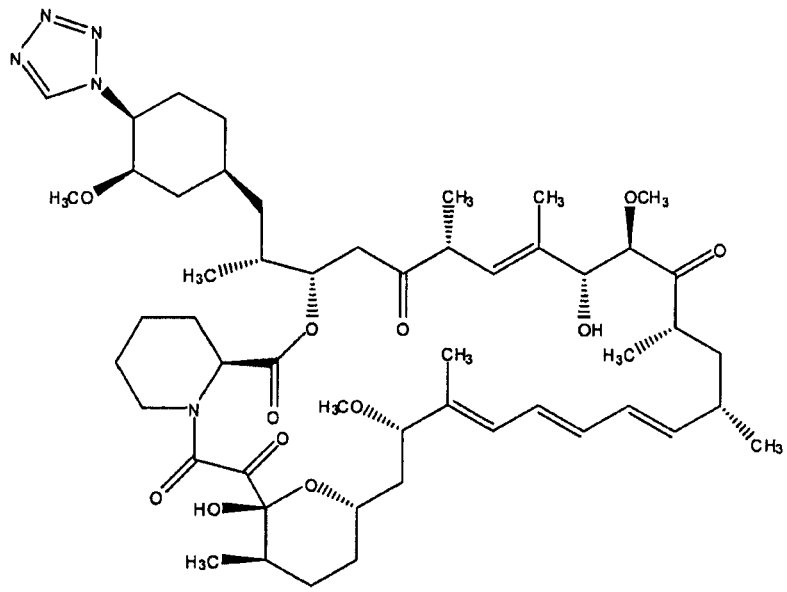"

Signed and Sealed this

Third Day of August, 2010

David J. Kappos
*Director of the United States Patent and Trademark Office*

And insert (At column 8, lines 50 – 65):
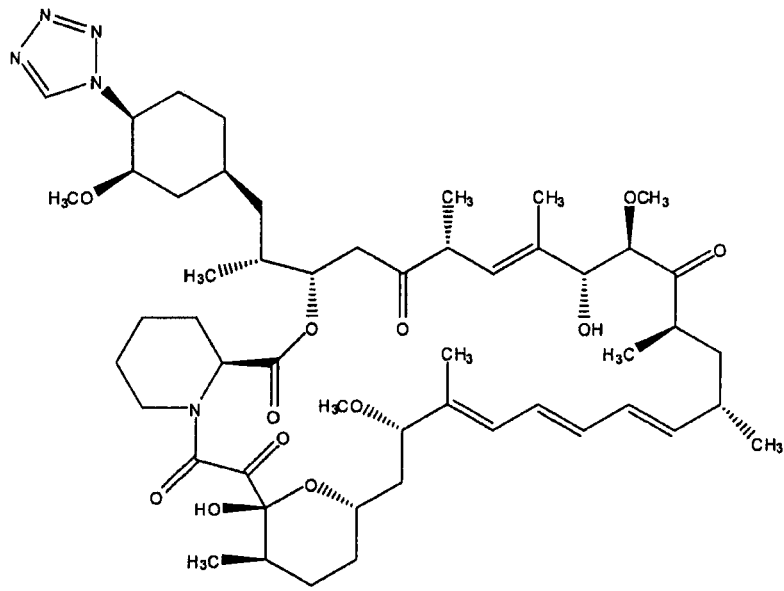
--                                                                                                      --
At column 9, lines 3 – 20, delete:
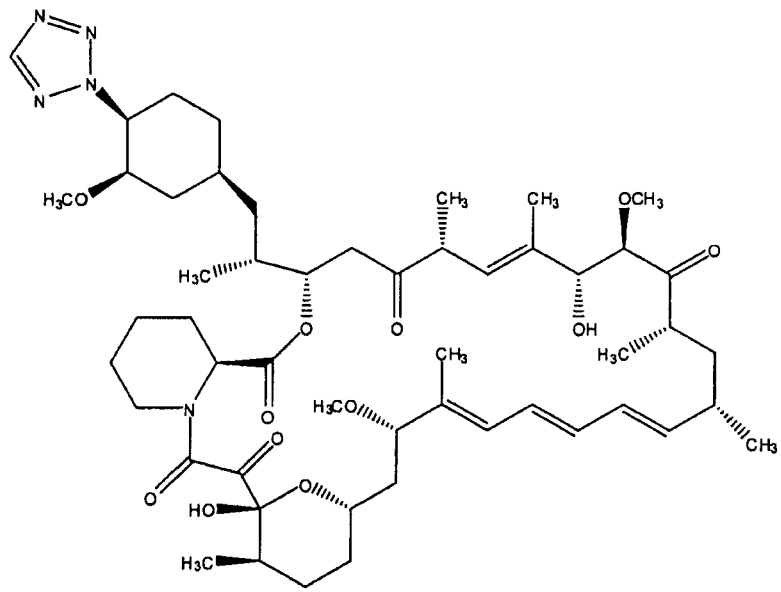
"                                                                                                       "

CERTIFICATE OF CORRECTION (continued)
U.S. Pat. No. 7,357,942 B2

And insert (At column 9, lines 3 – 20):

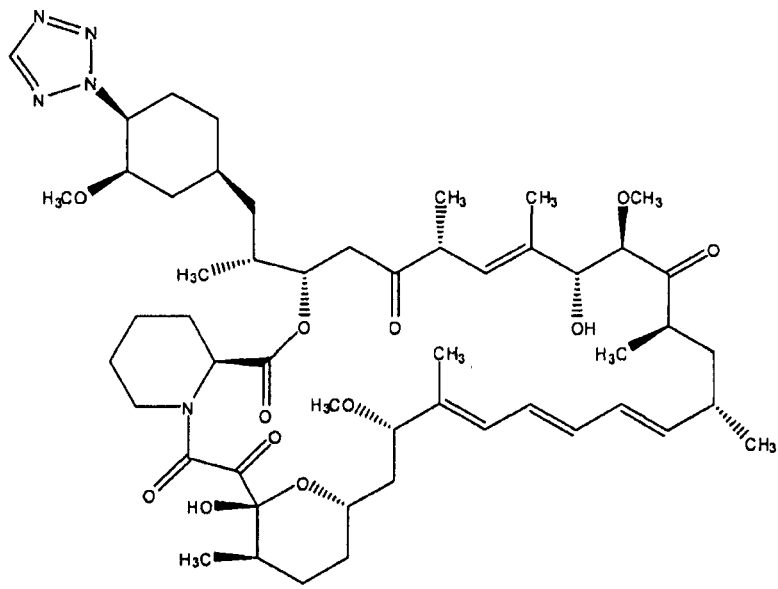

-- --